(12) United States Patent
Kasuya et al.

(10) Patent No.: US 7,811,556 B2
(45) Date of Patent: Oct. 12, 2010

(54) POLYMERIC MODIFIERS AND PHARMACEUTICAL COMPOSITIONS

(75) Inventors: Yuji Kasuya, Tokyo (JP); Masashi Honma, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 771 days.

(21) Appl. No.: 11/231,963

(22) Filed: Sep. 22, 2005

(65) Prior Publication Data

US 2006/0062754 A1 Mar. 23, 2006

Related U.S. Application Data

(63) Continuation of application No. PCT/JP2004/004134, filed on Mar. 24, 2004.

(30) Foreign Application Priority Data

| Mar. 24, 2003 | (JP) | ............................ 2003-080389 |
| Oct. 16, 2003 | (JP) | ............................ 2003-355853 |
| Dec. 24, 2003 | (JP) | ............................ 2003-426598 |

(51) Int. Cl.
*A61K 31/74* (2006.01)

(52) U.S. Cl. .................................. 424/78.17

(58) Field of Classification Search ........................ None
See application file for complete search history.

(56) References Cited

U.S. PATENT DOCUMENTS

| 1,217,005 | A | | 2/1917 | Johnson |
| 4,471,100 | A | * | 9/1984 | Tsubakimoto et al. ...... 525/367 |
| 5,282,905 | A | * | 2/1994 | Reichgott et al. ........... 148/247 |
| 5,358,984 | A | | 10/1994 | Hayes et al. |
| 6,004,583 | A | | 12/1999 | Platé et al. |
| 6,211,317 | B1 | * | 4/2001 | Albrecht et al. ............. 526/271 |
| 6,516,840 | B1 | * | 2/2003 | Klug et al. ..................... 149/2 |

FOREIGN PATENT DOCUMENTS

| JP | 2621308 | | 4/1997 |
| JP | 2701295 | | 10/1997 |
| JP | 2803265 | | 7/1998 |
| JP | 11-302199 | | 11/1999 |
| JP | 3035675 | | 2/2000 |
| JP | 3106265 | | 9/2000 |
| JP | 3271265 | | 1/2002 |
| JP | 2003-105003 | | 4/2003 |
| JP | 2003-105040 | | 4/2003 |
| WO | 97/23614 | A1 | 7/1997 |
| WO | 99/02131 | A2 | 1/1999 |
| WO | 00/40203 | A2 | 7/2000 |
| WO | WO 02/32169 | | 4/2002 |

OTHER PUBLICATIONS

Chapman, "PEGylated Antibodies and Antibody Fragments for Improved Therapy: a Review", *Advanced Drug Delivery Reviews*, 54:531-545 (2002).
Cowie, "Alternating Copolymerization", *Comprehensive Polymer Science* vol. 4, Chain Polymerization II, 377-422 (1989).
Davis, "The Origin of Pegnology", *Advanced Drug Delivery Reviews*, 54:457-458 (2002).
Hinds et al., "Effects of PEG Conjugation on Insulin Properties", *Advanced Drug Delivery Reviews*, 54:505-530 (2002).
International Search Report completed Jun. 24, 2004 in application PCT/JP2004/004134.
Kinstler et al., "Mono-N-Terminal Poly(ethylene Glycol)-Protein Conjugates", *Advanced Drug Delivery Reviews*, 54:477-485 (2002).
Reddy et al., "Use of Peginterferon Alfa-2a (40 KD) (Pegasys®) for the Treatment of Hepatitis C", *Advanced Drug Delivery Reviews*, 54:571-586 (2002).
Roberts et al., "Chemistry for Peptide and Protein PEGylation", *Advanced Drug Delivery Reviews*, 54:459-476 (2002).
Sato, "Enzymatic Procedure for Site-Specific Pegylation of Proteins", *Advanced Drug Delivery Reviews*, 54:487-504 (2002).
Veronese et al., "Introduction and Overview of Peptide and Protein Pegylation", *Advanced Drug delivery Reviews*, 54:453-456 (2002).
Veronese et al., "Polyethylene Glycol-Superoxide Dismutase, a Conjugate in Search of Exploitation", *Advanced Drug Delivery Reviews*, 54:587-606 (2002).
Wang et al., "Structural and Biological Characterization of Pegylated Recombinant Interferon Alpha-2b and Its Therapeutic Implications", *Advanced Drug Delivery Reviews*, 54:547-570 (2002).
Yoshimoto et al., "Polyethylene Glycol Derivative-Modified Cholesterol Oxidase Soluble and Active in Benzene", *Biochemical and Biophysical Research Communications*, 148(2):876-882 (1987).

* cited by examiner

*Primary Examiner*—Michael G Hartley
*Assistant Examiner*—Paul Dickinson
(74) *Attorney, Agent, or Firm*—Arnold & Porter LLP

(57) ABSTRACT

A copolymer or a pharmacologically acceptable salt thereof is provided, which contains, as constitutional units, (a) one or more structural units of formula (I): wherein m is an integer of from 3 to 100, Alk represents alkyline, and $R^1$ and $R^2$ are the same or different and each represents hydrogen or optionally substituted alkyl, and (b) one or more structural units of formula (II): wherein $R^3$ represents hydroxyl, optionally substituted alkoxy, optionally substituted aryloxy, or a group represented by the formula —$NR^4R^5$, wherein $R^4$ and $R^5$ are the same or different and each represents hydrogen or optionally substituted alkyl. There is further provided a pharmaceutical composition comprising said copolymer, a protein modifier comprising said copolymer, a complex of said copolymer with a protein, and method of preventing or treating diseases using said complex, use of said complex in the manufacture of a medicament for preventing or treating diseases and methods for the synthesis of said copolymers and said complexes.

53 Claims, 2 Drawing Sheets

SEQUENCE LISTING

```
<160> NUMBER OF SEQ ID NOS: 1

<210> SEQ ID NO 1
<211> LENGTH: 401
<212> TYPE: PRT
<213> ORGANISM: Homo sapiens
<220> FEATURE:
<221> NAME/KEY: SIGNAL
<222> LOCATION: (-21)..(-1)
<220> FEATURE:
<221> NAME/KEY: mat_peptide
<222> LOCATION: (+1)..(+380)

<400> SEQUENCE: 1

Met Asn Asn Leu Leu Cys Cys Ala Leu Val Phe Leu Asp Ile Ser Ile
    -20                 -15                 -10

Lys Trp Thr Thr Gln Glu Thr Phe Pro Pro Lys Tyr Leu His Tyr Asp
 -5              -1   1               5                  10

Glu Glu Thr Ser His Gln Leu Leu Cys Asp Lys Cys Pro Pro Gly Thr
                15                  20                  25

Tyr Leu Lys Gln His Cys Thr Ala Lys Trp Lys Thr Val Cys Ala Pro
        30                  35                  40
```

```
Cys Pro Asp His Tyr Tyr Thr Asp Ser Trp His Thr Ser Asp Glu Cys
 45                  50                  55

Leu Tyr Cys Ser Pro Val Cys Lys Glu Leu Gln Tyr Val Lys Gln Glu
 60                  65                  70                  75

Cys Asn Arg Thr His Asn Arg Val Cys Glu Cys Lys Glu Gly Arg Tyr
                 80                  85                  90

Leu Glu Ile Glu Phe Cys Leu Lys His Arg Ser Cys Pro Pro Gly Phe
             95                 100                 105

Gly Val Val Gln Ala Gly Thr Pro Glu Arg Asn Thr Val Cys Lys Arg
            110                 115                 120

Cys Pro Asp Gly Phe Phe Ser Asn Glu Thr Ser Ser Lys Ala Pro Cys
        125                 130                 135

Arg Lys His Thr Asn Cys Ser Val Phe Gly Leu Leu Thr Gln Lys
140                 145                 150                 155

Gly Asn Ala Thr His Asp Asn Ile Cys Ser Gly Asn Ser Glu Ser Thr
                160                 165                 170

Gln Lys Cys Gly Ile Asp Val Thr Leu Cys Glu Glu Ala Phe Phe Arg
            175                 180                 185

Phe Ala Val Pro Thr Lys Phe Thr Pro Asn Trp Leu Ser Val Leu Val
            190                 195                 200

Asp Asn Leu Pro Gly Thr Lys Val Asn Ala Glu Ser Val Glu Arg Ile
        205                 210                 215

Lys Arg Gln His Ser Ser Gln Glu Gln Thr Phe Gln Leu Leu Lys Leu
220                 225                 230                 235

Trp Lys His Gln Asn Lys Asp Gln Asp Ile Val Lys Lys Ile Ile Gln
                240                 245                 250

Asp Ile Asp Leu Cys Glu Asn Ser Val Gln Arg His Ile Gly His Ala
            255                 260                 265

Asn Leu Thr Phe Glu Gln Leu Arg Ser Leu Met Glu Ser Leu Pro Gly
            270                 275                 280

Lys Lys Val Gly Ala Glu Asp Ile Glu Lys Thr Ile Lys Ala Cys Lys
285                 290                 295

Pro Ser Asp Gln Ile Leu Lys Leu Leu Ser Leu Trp Arg Ile Lys Asn
300                 305                 310                 315

Gly Asp Gln Asp Thr Leu Lys Gly Leu Met His Ala Leu Lys His Ser
                320                 325                 330

Lys Thr Tyr His Phe Pro Lys Thr Val Thr Gln Ser Leu Lys Lys Thr
                335                 340                 345

Ile Arg Phe Leu His Ser Phe Thr Met Tyr Lys Leu Tyr Gln Lys Leu
            350                 355                 360

Phe Leu Glu Met Ile Gly Asn Gln Val Gln Ser Val Lys Ile Ser Cys
            365                 370                 375

Leu
380
```

POLYMERIC MODIFIERS AND PHARMACEUTICAL COMPOSITIONS

CROSS-REFERENCE TO RELATED APPLICATIONS

This application is a continuation of PCT/JP2004/004134, filed Mar. 24, 2004, which claims priority to Japanese Patent Application Nos. 2003-080389, filed Mar. 24, 2003, 2003-355853, filed Oct. 16, 2003, and 2003-426598, filed Dec. 24, 2003. The entire disclosures of the listed applications are hereby incorporated by reference in their entirety.

INCORPORATION OF SEQUENCE LISTING

A paper copy of the Sequence Listing and a computer readable form of the sequence listing on diskette, containing the file named Seqlist029.txt, which is four kilobytes in size (measured in MS-DOS), was recorded and filed on Sep. 22, 2005, and which is hereby incorporated by reference.

TECHNICAL FIELD

The present invention relates to a novel copolymer, a pharmaceutical composition comprising said copolymer, a protein modifier comprising said copolymer, a complex of said copolymer with a protein, a method of preventing or treating diseases using said complex, use of said complex in the manufacture of a medicament for preventing or treating diseases and methods for the synthesis of said copolymers and said complexes.

BACKGROUND OF THE INVENTION

The modification of proteins with additional agents such as polymers has commonly been employed for the purpose of providing improved pharmaceutical properties, e.g. improved stability and retention in the blood and reduced antigenicity [for example, see F. M. Veronese and J. M. Harris, "Peptide and Protein Pegylation", Advanced Drug Delivery Reviews 54(4), 2002].

When modifying proteins with a polymer, one technique employed in the past comprises binding the protein and the polymeric modifier via a covalent bond (e.g. see WO-A-97/23614). In other examples of the polymer modification of a protein, such as in the modification of a drug with a polymer, the drug has been modified via a non-covalent bond. One such example is provided in Japanese Patent Application (Kokai) No. Hei 11-302199, which discloses that a graft copolymer, which comprises a graft chain of a non-ionic polymer and a main chain of a negatively-charged polymer, forms an inclusion complex with a substance capable of being positively charged under physiological conditions, for example, a liposome or poly-L-lysine carrying positive charge, to improve the retention in blood. Another alternative is suggested in WO-A-99/02131 which discloses that a protein and a water-soluble polymer can be mixed under specific conditions in the presence of an organic solvent to provide controlled-release microparticles.

Unfortunately, few of these polymeric protein modifiers have been particularly successful for a variety of reasons. One recent example of a polymeric protein modifier that shows some improved properties comprises a polymaleic acid compound-based copolymer containing a polyoxyalkylene alkyl ether compound as a constituent unit [see, for example, Japanese Patent Nos. 3035675 and 3271265]. These polymeric modifiers certainly show improved binding to the target proteins. However, significant problems still exist with such copolymers. The maleic anhydride moiety thereof is found to bind to proteins non-specifically. This results in the obtained complexes of the copolymer and the protein showing non-uniform properties depending upon the conditions. Particularly, it is found that these polymeric modifiers tend to readily form disorganised cross-linked structures with the proteins thus forming bulky complexes that cause excessive modification of the protein structure and hence reduction of desired protein activity. Furthermore, complexes of these polymeric protein modifiers and a protein have been found to show unsatisfactory retention in the blood after administration.

There is, therefore, a need for a polymeric modifier capable of providing a complex having uniform properties, especially reduced production of disorganised cross-linked structures with the protein, better maintenance of protein activity and excellent retention of the protein in the blood after administration of said complex.

BRIEF SUMMARY OF THE INVENTION

It is, therefore, an object of the present invention to provide a polymeric modifier capable of providing a complex having uniform properties, especially reduced production of disorganised cross-linked structures with the protein, better maintenance of protein activity and excellent retention of the protein in the blood after administration of said complex.

The present inventors have made an extensive study of various protein modifiers, and as a result, have succeeded in obtaining novel copolymers that are capable of forming complexes with proteins that have uniform properties, and of markedly improving the retention in the blood of the proteins of said complexes, thus leading to the completion of the present invention.

Other objects and advantages of the present invention will become apparent as the description proceeds.

Thus, the present invention provides a copolymer or a pharmacologically acceptable salt thereof, which contains, as constitutional units, (a) one or more structural units which may be the same or different from each other and which are represented by the formula (I) below:

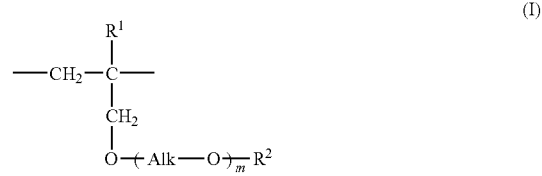

wherein:

m is an integer of from 3 to 100,

Alk represents an alkylene group having from 1 to 6 carbon atoms, and $R^1$ and $R^2$ are the same or different and each represents a hydrogen atom or an alkyl group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below, and (b) one or more structural units which may be the same or different from each other and which are represented by the formula (II):

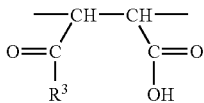

(II)

wherein:

R³ represents a hydroxyl group, an alkoxy group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below, an aryloxy group having from 6 to 14 carbon atoms that may optionally be substituted with from 1 to 5 substituents selected from Substituents A defined below, or a group represented by the formula —NR⁴R⁵, wherein R⁴ and R⁵ are the same or different from each other and each represents a hydrogen atom or an alkyl group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below;

Substituents A are selected from alkyl groups having from 1 to 6 carbon atoms, alkoxy groups having from 1 to 6 carbon atoms, halogen atoms, hydroxy groups, nitro groups and carboxy groups.

The present invention further provides a copolymer or a pharmacologically acceptable salt thereof obtainable by subjecting one or more carboxylic anhydride moieties of formula (III) in a copolymer which contains, as constitutional units, (a) one or more structural units which may be the same or different from each other and which are represented by the formula (I) below:

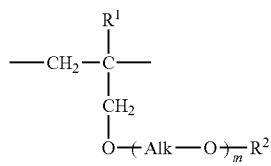

(I)

wherein:

m is an integer of from 3 to 100,

Alk represents an alkylene group having from 1 to 6 carbon atoms, and

R¹ and R² are the same or different and each represents a hydrogen atom or an alkyl group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below, and (b) said one or more carboxylic anhydride moieties of formula (III):

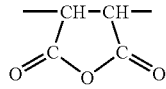

(III)

to one or more reactions selected from the group consisting of (i) hydrolysis, (ii) ammonolysis, (iii) aminolysis and (iv) alcoholysis;

Substituents A are selected from alkyl groups having from 1 to 6 carbon atoms, alkoxy groups having from 1 to 6 carbon atoms, halogen atoms, hydroxy groups, nitro groups and carboxy groups.

The present invention also provides a pharmaceutical composition comprising at least one copolymer or a pharmacologically acceptable salt thereof of the present invention as described above, particularly such a composition that also comprises at least one protein or an analogue or variant thereof.

The present invention also provides a modifier capable of modifying a protein or an analogue or variant thereof, said modifier comprising a copolymer or a pharmacologically acceptable salt thereof of the present invention as described above.

The present invention also provides a complex comprising at least one protein or an analogue or variant thereof which is bound to at least one copolymer or a pharmacologically acceptable salt thereof of the present invention as described above.

The present invention also provides a pharmaceutical composition comprising an effective amount of a pharmacologically active agent together with a carrier or diluent therefor, wherein said pharmacologically active agent is a complex comprising at least one protein or an analogue or variant thereof which is bound to at least one copolymer or a pharmacologically acceptable salt thereof of the present invention as described above.

The present invention also provides also provides a method for prolonging the time that a protein or an analogue or variant thereof is retained in the bloodstream after administration to a patient by complexing said protein or an analogue or variant thereof with at least one copolymer or a pharmacologically acceptable salt thereof of the present invention as described above.

The present invention also provides a method for the treatment or prophylaxis of a disease in a patient that is susceptible to a protein or an analogue or variant thereof comprising administering to said patient an effective amount of a complex comprising said protein or an analogue or variant thereof which is bound to at least one copolymer or a pharmacologically acceptable salt thereof of the present invention as described above.

The present invention also provides the use of a complex comprising a protein or an analogue or variant thereof which is bound to at least one copolymer or a pharmacologically acceptable salt thereof of the present invention as described above in the manufacture of a medicament for the prophylaxis or treatment of a disease susceptible to said protein or an analogue or variant thereof.

The present invention also provides a method for the preparation of a copolymer or a pharmacologically acceptable salt thereof containing, as constitutional units, (a) one or more structural units which may be the same or different from each other and which are represented by the formula (I) below:

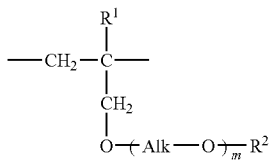

wherein:

m, Alk, $R^1$ and $R^2$ are as defined above, and (b) one or more structural units which may be the same or different from each other and which are represented by the formula (II):

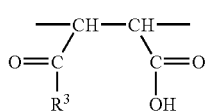

wherein:

$R^3$ is as defined above;

said method comprising subjecting one or more carboxylic anhydride moieties of formula (III) in a copolymer which contains, as constitutional units, (c) one or more structural units which may be the same or different from each other and which are represented by the formula (I) as defined above, and (d) said one or more carboxylic anhydride moieties of formula (III):

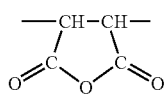

to one or more reactions selected from the group consisting of (i) hydrolysis, (ii) ammonolysis, (iii) aminolysis and (iv) alcoholysis.

The present invention also provides a method for the preparation of a complex comprising at least one protein or an analogue or variant thereof which is bound to at least one copolymer or a pharmacologically acceptable salt thereof as defined above, said method comprising reacting said copolymer or a pharmacologically acceptable salt thereof with said protein or an analogue or variant thereof under conditions favouring the formation of said complex.

(1) Molecular weight markers (2) Complex of poly(PEG$_{500}$-MA)a-Na (Compound No. 9)-OCIF [OCIF:polymeric modifier=1:1 (weight ratio)]

(3) Complex of poly(PEG$_{500}$-MA)a-Na (Compound No. 9)-OCIF [OCIF:polymeric modifier=1:2 (weight ratio)]

(4) Complex of poly(PEG$_{500}$-MA)a-Na (Compound No. 9)-OCIF [OCIF:polymeric modifier=1:3 (weight ratio)]

(5) Complex of poly(PEG$_{500}$-MA)a-Na (Compound No. 9)-OCIF [OCIF:polymeric modifier=1:4 (weight ratio)]

(6) Complex of poly(PEG$_{500}$-MA)a-Na (Compound No. 9)-OCIF [OCIF:polymeric modifier=1:5 (weight ratio)]

(7) Non-modified OCIF.

Figure 2:
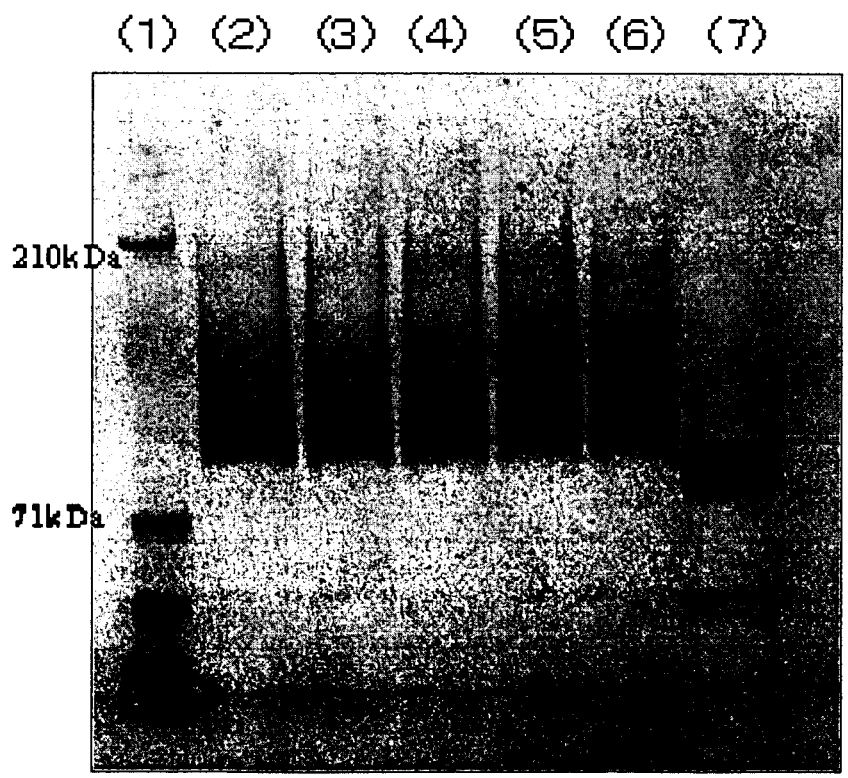

FIG. 2 shows further results of SDS polyacrylamide gel electrophoresis on complexes of the present invention of poly(PEG$_{500}$-MA)a-OCIF under non-reducing conditions as performed in Test Example 6 below:

(1) Molecular weight marker (2) Complex of poly(PEG$_{500}$-MA)a-Na (Compound No. 9)-OCIF [OCIF:polymeric modifier=1:1 (weight ratio), OCIF concentration during incubation: 3.5 mg/ml]

(3) Complex of poly(PEG$_{500}$-MA)a-Na (Compound No. 9)-OCIF [OCIF:polymeric modifier=1:1 (weight ratio), OCIF concentration during incubation: 1.75 mg/ml]

(4) Complex of poly(PEG$_{500}$-MA)a-Na (Compound No. 9)-OCIF [OCIF:polymeric modifier=1:1 (weight ratio), OCIF concentration during incubation: 0.875 mg/ml]

(5) Complex of poly(PEG$_{500}$-MA)a-Na (Compound No. 9)-OCIF [OCIF:polymeric modifier=1:2 (weight ratio), OCIF concentration during incubation: 1.75 mg/ml]

(6) Complex of poly(PEG$_{500}$-MA)a-Na (Compound No. 9)-OCIF [OCIF:polymeric modifier=1:4 (weight ratio), OCIF concentration during incubation: 0.875 mg/ml]

(7) Non-modified OCIF.

Figure 3:
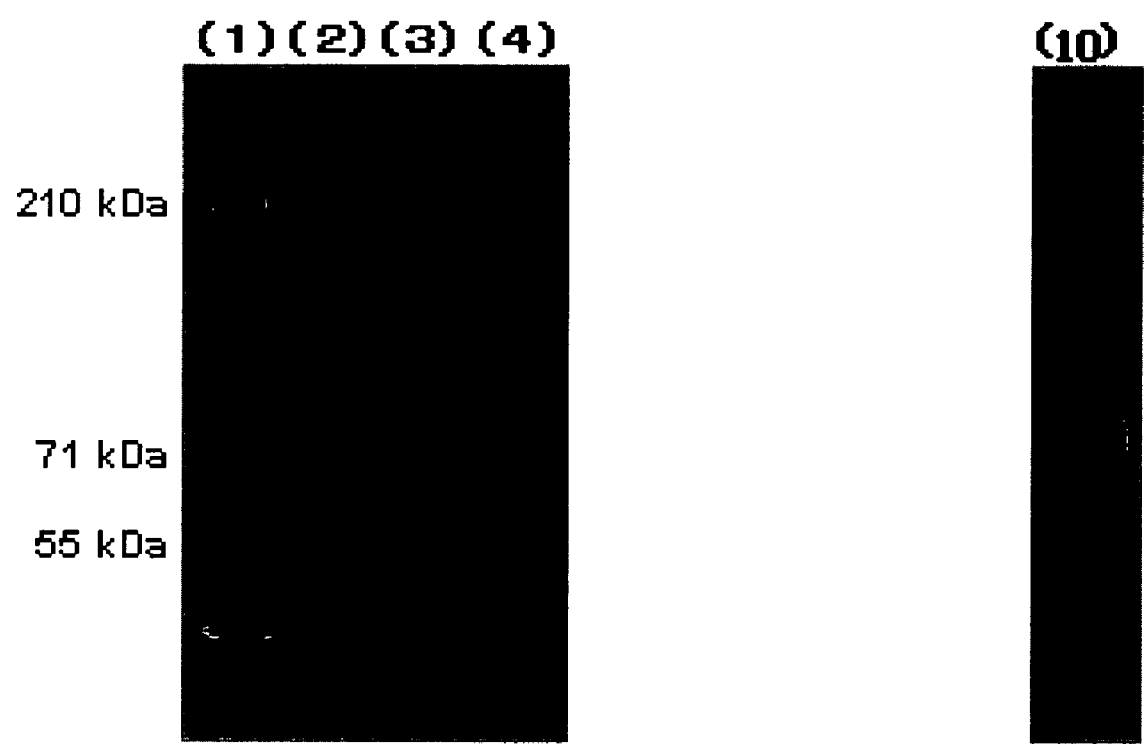

FIG. 3 shows the results of SDS polyacrylamide gel electrophoresis of prior art complexes of poly(PEG$_{500}$-MA)-OCIF under non-reducing conditions as performed in Test Example 6 below:

(1) Molecular weight marker (2) Complex of poly(PEG$_{500}$-MA) (AM-0530K)-OCIF [OCIF:polymeric modifier=1:10 (weight ratio)]

(3) Complex of poly(PEG$_{500}$-MA) (AM-0530K)-OCIF [OCIF:polymeric modifier=1:2.5 (weight ratio)]

(4) Complex of poly(PEG$_{500}$-MA) (AM-0530K)-OCIF [OCIF:polymeric modifier=1:1 (weight ratio)]

(10) Non-modified OCIF.

DETAILED DESCRIPTION OF THE INVENTION (1) As noted above, one aspect of the present invention provides a copolymer or a pharmacologically acceptable salt thereof, which contains, as constitutional units, (a) one or more structural units which may be the same or different from each other and which are represented by the formula (I) below:

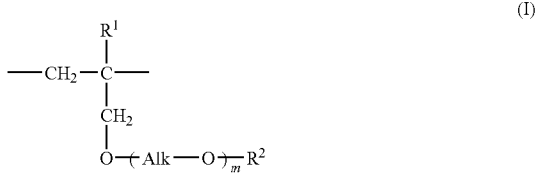

wherein:
m, Alk, $R^1$ and $R^2$ are as defined above, and (b) one or more structural units which may be the same or different from each other and which are represented by the formula (II):

wherein $R^3$ is as defined above. Of these copolymers and pharmacologically acceptable salts thereof, preferred ones include:

(2) a copolymer or a pharmacologically acceptable salt thereof according to (1), wherein the structural units represented by the formula (I) and the structural units represented by the formula (II) are arranged in an alternating head-to-head sequence, an alternating head-to-tail sequence or an alternating mixed sequence of head-to-head and head-to-tail;

(3) a copolymer or a pharmacologically acceptable salt thereof according to (1), wherein the structural units represented by the formula (I) and the structural units represented by the formula (II) are arranged in a random sequence;

(4) a copolymer or a pharmacologically acceptable salt thereof according to any one of (1) to (3), wherein Alk is an ethylene or trimethylene group;

(5) a copolymer or a pharmacologically acceptable salt thereof according to (4), wherein Alk is an ethylene group;

(6) a copolymer or a pharmacologically acceptable salt thereof according to any one of (1) to (5), wherein m is an integer of from 3 to 50;

(7) a copolymer or a pharmacologically acceptable salt thereof according to (6), wherein m is an integer of from 3 to 40;

(8) a copolymer or a pharmacologically acceptable salt thereof according to (7), wherein m is an integer of from 6 to 16 or 28 to 38;

(9) a copolymer or a pharmacologically acceptable salt thereof according to (8), wherein m is an integer of from 6 to 16;

(10) a copolymer or a pharmacologically acceptable salt thereof according to any one of (1) to (9), wherein $R^1$ is a hydrogen atom or a methyl group;

(11) a copolymer or a pharmacologically acceptable salt thereof according to (10), wherein $R^1$ is a hydrogen atom;

(12) a copolymer or a pharmacologically acceptable salt thereof according to any one of (1) to (11), wherein $R^2$ is a hydrogen atom or a methyl group;

(13) a copolymer or a pharmacologically acceptable salt thereof according to (12), wherein $R^2$ is a methyl group;

(14) a copolymer or a pharmacologically acceptable salt thereof according to any one of (1) to (13), wherein $R^3$ is a hydroxyl group, an alkoxy group having from 1 to 6 carbon atoms or a group represented by the formula —$NR^4R^5$, wherein $R^4$ and $R^5$ are the same or different and each represents a hydrogen atom or an alkyl group having from 1 to 6 carbon atoms;

(15) a copolymer or a pharmacologically acceptable salt thereof according to (14), wherein $R^3$ is a hydroxyl group or an alkoxy group having from 1 to 6 carbon atoms;

(16) a copolymer or a pharmacologically acceptable salt thereof according to (15), comprising at least one structural unit represented by the formula (II) in which $R^3$ is an alkoxy group having from 1 to 6 carbon atoms and optionally at least one structural unit represented by the formula (II) in which $R^3$ is a hydroxyl group, wherein the ratio between the structural units represented by the formula (II) in which $R^3$ is a hydroxy group and the structural units represented by the formula (II) in which $R^3$ is an alkoxy group having from 1 to 6 carbon atoms is in the range of from 4:6 to 0:10;

(17) a copolymer or a pharmacologically acceptable salt thereof according to (15) or (16), wherein $R^3$ is an alkoxy group having from 1 to 6 carbon atoms;

(18) a copolymer or a pharmacologically acceptable salt thereof according to any one of (15) to (17), wherein said alkoxy group having from 1 to 6 carbon atoms is an ethoxy group;

(19) a copolymer or a pharmacologically acceptable salt thereof according to (14), wherein $R^3$ is a hydroxyl group or a group represented by the formula —$NR^4R^5$, wherein $R^4$ and $R^5$ are the same or different and each represents a hydrogen atom or an alkyl group having from 1 to 6 carbon atoms;

(20) a copolymer or a pharmacologically acceptable salt thereof according to (19), comprising at least one structural unit represented by the formula (II) in which $R^3$ is a group represented by the formula —$NR^4R^5$, wherein $R^4$ and $R^5$ are the same or different and each represents a hydrogen atom or an alkyl group having from 1 to 6 carbon atoms and optionally at least one structural unit represented by the formula (II) in which $R^3$ is a hydroxyl group, wherein the ratio between the structural units represented by the formula (II) in which $R^3$ is a hydroxy group and the structural units represented by the formula (II) in which $R^3$ is a group represented by the formula —$NR^4R^5$ is in the range of from 5:5 to 0:10;

(21) a copolymer or a pharmacologically acceptable salt thereof according to (20), wherein the ratio between the structural units represented by the formula (II) in which $R^3$ is a hydroxy group and the structural units represented by the formula (II) in which $R^3$ is a group represented by the formula —$NR^4R^5$ is in the range of from 4:6 to 0:10;

(22) a copolymer or a pharmacologically acceptable salt thereof according to any one of (19) to (21), wherein $R^3$ is a group represented by the formula $-NR^4R^5$, wherein $R^4$ and $R^5$ are the same or different and each represents a hydrogen atom or an alkyl group having from 1 to 6 carbon atoms;

(23) a copolymer or a pharmacologically acceptable salt thereof according to any one of (19) to (22), wherein the group represented by the formula $-NR^4R^5$ is an amino group, a methylamino group or a dimethylamino group;

(24) a copolymer or a pharmacologically acceptable salt thereof according to (23), wherein the group represented by the formula $-NR^4R^5$ is an amino group;

(25) a copolymer or a pharmacologically acceptable salt thereof according to (23), wherein the group represented by the formula $-NR^4R^5$ is a dimethylamino group;

(26) a copolymer or a pharmacologically acceptable salt thereof according to (14), wherein $R^3$ is a hydroxyl group;

(27) a copolymer or a pharmacologically acceptable salt thereof according to (14), wherein $R^3$ is a 1-amino-2-propanol group;

(28) a copolymer or a pharmacologically acceptable salt thereof according to any one of (1) to (27), wherein the ratio between the structural unit represented by the formula (I) and the structural unit represented by the formula (II) is in the range of from 10:1 to 1:10;

(29) a copolymer or a pharmacologically acceptable salt thereof according to (28), wherein the ratio between the structural unit represented by the formula (I) and the structural unit represented by the formula (II) is in the range of from 3:1 to 1:8;

(30) a copolymer or a pharmacologically acceptable salt thereof according to (28), wherein the ratio between the structural unit represented by the formula (I) and the structural unit represented by the formula (II) is in the range of from 2:1 to 1:2 or 1:2 to 1:6;

(31) a copolymer or a pharmacologically acceptable salt thereof according to (28), wherein the ratio between the structural unit represented by the formula (I) and the structural unit represented by the formula (II) is 1:1 or in the range of from 1:2 to 1:4;

(32) a copolymer or a pharmacologically acceptable salt thereof according to any one of (1) to (31), wherein the average degree of polymerization is in the range of from 5 to 200;

(33) a copolymer or a pharmacologically acceptable salt thereof according to (32), wherein the average degree of polymerization is in the range of from 5 to 50;

(34) a copolymer or a pharmacologically acceptable salt thereof according to (33), wherein the average degree of polymerization is in the range of from 5 to 20;

(35) a copolymer or a pharmacologically acceptable salt thereof according to (32), wherein the average degree of polymerization is in the range of from 20 to 30;

(36) a copolymer or a pharmacologically acceptable salt thereof according to (32), wherein the average degree of polymerization is in the range of from 30 to 40;

(37) a copolymer or a pharmacologically acceptable salt thereof according to any one of (1) to (31), wherein the Stokes radius thereof is 9.3 nm or less;

(38) a copolymer or a pharmacologically acceptable salt thereof according to (37), wherein the Stokes radius thereof is 7.3 nm or less;

(39) a copolymer or a pharmacologically acceptable salt thereof according to (38), wherein the Stokes radius thereof is 6.2 nm or less;

(40) a copolymer or a pharmacologically acceptable salt thereof according to (39), wherein the Stokes radius thereof is 4.7 nm or less;

(41) a copolymer or a pharmacologically acceptable salt thereof according to (40), wherein the Stokes radius thereof is 3.1 nm or less;

(42) a copolymer or a pharmacologically acceptable salt thereof according to (37), wherein the Stokes radius thereof is in the range of from 1.5 nm to 4.7 nm;

(43) a copolymer or a pharmacologically acceptable salt thereof according to (37), wherein the Stokes radius thereof is in the range of from 3.1 nm to 6.2 nm; and

(44) a copolymer according or a pharmacologically acceptable salt thereof according to (1) wherein:

m is an integer of from 3 to 100,

Alk represents an alkylene group having from 1 to 6 carbon atoms, $R^1$ and $R^2$ are the same or different and each represents a hydrogen atom or an alkyl group having from 1 to 6 carbon atoms, and $R^3$ represents a hydroxyl group, an alkoxy group having from 1 to 6 carbon atoms that may optionally be substituted with one hydroxy group, or a group represented by the formula $-NR^4R^5$, wherein $R^4$ and $R^5$ are the same or different from each other and each represents a hydrogen atom or an alkyl group having from 1 to 6 carbon atoms that may optionally be substituted with one hydroxy group;

(45) a copolymer or a pharmacologically acceptable salt thereof according to (1), wherein Alk represents an ethylene group, $R^1$ represents a hydrogen atom, $R^2$ represents a methyl group and m, $R^3$, the ratio of the structural units of formulae (I) and (II) (the composition ratio) and, where relevant, the ratio between the units of formula (II) wherein $R^3$ represents a hydroxy group and the units of formula (II) wherein $R^3$ represents a group other than hydroxy (the hydrolysis ratio) are selected from the following:

(i) m is from 6 to 16, $R^3$ is a hydroxy group, the composition ratio is 1:1 and the average degree of polymerisation is from 30 to 40;

(ii) m is from 28 to 38, $R^3$ is a hydroxy group, the composition ratio is 1:1 and the average degree of polymerisation is from 10 to 15;

(iii) m is from 6 to 16, $R^3$ is an amino group, the composition ratio is 1:1 and the average degree of polymerisation is from 30 to 40;

(iv) m is from 6 to 16, $R^3$ is a dimethylamino group, the composition ratio is 1:1 and the average degree of polymerisation is from 30 to 40;

(v) m is from 6 to 16, $R^3$ is a 1-amino-2-propanol group, the composition ratio is 1:1 and the average degree of polymerisation is from 30 to 40;

(vi) m is from 6 to 16, $R^3$ is selected from ethoxy and hydroxy groups, the composition ratio is 1:1, the average degree of polymerisation is from 30 to 40 and the hydrolysis ratio is 4:6;

(vii) m is from 28 to 16, $R^3$ is selected from amino and hydroxy groups, the composition ratio is 1:1, the average degree of polymerisation is from 10 to 15 and the hydrolysis ratio is 4:6;

(viii) m is from 28 to 38, $R^3$ is a dimethylamino group, the composition ratio is 1:1 and the average degree of polymerisation is from 10 to 15;

(ix) m is from 6 to 16, $R^3$ is selected from amino and hydroxy groups, the composition ratio is 1:1, the average degree of polymerisation is from 30 to 40, the hydrolysis ratio is 3.1:6.9 and the copolymer is a sodium salt;

(x) m is from 6 to 16, $R^3$ is selected from amino and hydroxy groups, the composition ratio is 1:1, the average degree of polymerisation is from 30 to 40 and the hydrolysis ratio is 1.4:8.6;

(xi) m is from 6 to 16, $R^3$ is selected from dimethylamino and hydroxy groups, the composition ratio is 1:1, the average degree of polymerisation is from 30 to 40, the hydrolysis ratio is 2.9:7.1 and the copolymer is a sodium salt;

(xii) m is from 6 to 16, $R^3$ is an amino group, the composition ratio is 1:2.4 and the average degree of polymerisation is from 20 to 30;

(xiii) m is from 6 to 16, $R^3$ is selected from amino and hydroxy groups, the composition ratio is 1:2.4, the average degree of polymerisation is from 20 to 30 and the hydrolysis ratio is 0.4:9.6;

(xiv) m is from 6 to 16, $R^3$ is selected from amino and hydroxy groups, the composition ratio is 1:2.4, the average degree of polymerisation is from 20 to 30 and the hydrolysis ratio is 2.9:7.1;

(xv) m is from 6 to 16, $R^3$ is selected from amino and hydroxy groups, the composition ratio is 1:2.4, the average degree of polymerisation is from 20 to 30 and the hydrolysis ratio is 0.9:9.1;

(xvi) m is from 6 to 16, $R^3$ is selected from amino and hydroxy groups, the composition ratio is 1:2.4, the average degree of polymerisation is from 20 to 30 and the hydrolysis ratio is 0.5:9.5;

(xvii) m is from 6 to 16, $R^3$ is selected from amino and hydroxy groups, the composition ratio is 1:2.4, the average degree of polymerisation is from 20 to 30 and the hydrolysis ratio is 1.3:8.7;

(xviii) m is from 6 to 16, $R^3$ is selected from amino and hydroxy groups, the composition ratio is 1:2.4, the average degree of polymerisation is from 20 to 30 and the hydrolysis ratio is 1.9:8.1;

(xix) m is from 6 to 16, $R^3$ is selected from amino and hydroxy groups, the composition ratio is 1:2.4, the average degree of polymerisation is from 20 to 30 and the hydrolysis ratio is 1.0:9.0;

(xx) m is from 6 to 16, $R^3$ is selected from amino and hydroxy groups, the composition ratio is 1:2.4, the average degree of polymerisation is from 20 to 30 and the hydrolysis ratio is 0.8:9.2;

(xxi) m is from 6 to 16, $R^3$ is selected from amino and hydroxy groups, the composition ratio is 1:2.4, the average degree of polymerisation is from 20 to 30 and the hydrolysis ratio is 4.6:5.4;

(xxii) m is from 6 to 16, $R^3$ is selected from amino and hydroxy groups, the composition ratio is 1:2.4, the average degree of polymerisation is from 20 to 30 and the hydrolysis ratio is 1.2:8.8;

(xxiii) m is from 6 to 16, $R^3$ is selected from amino and hydroxy groups, the composition ratio is 1:2.4, the average degree of polymerisation is from 20 to 30 and the hydrolysis ratio is 2.0:8.0;

(xxiv) m is from 6 to 16, $R^3$ is selected from amino and hydroxy groups, the composition ratio is 1:2.4, the average degree of polymerisation is from 20 to 30 and the hydrolysis ratio is 1.1:8.9;

(xxv) m is from 6 to 16, $R^3$ is selected from amino and hydroxy groups, the composition ratio is 1:2.4, the average degree of polymerisation is from 20 to 30 and the hydrolysis ratio is 2.4:7.6;

(xxvi) m is from 6 to 16, $R^3$ is selected from amino and hydroxy groups, the composition ratio is 1:2.4, the average degree of polymerisation is from 20 to 30 and the hydrolysis ratio is 0.9:9.1;

(xxvii) m is from 6 to 16, $R^3$ is selected from amino and hydroxy groups, the composition ratio is 1:2.4, the average degree of polymerisation is from 20 to 30 and the hydrolysis ratio is 1.5:8.5;

(xxviii) m is from 6 to 16, $R^3$ is selected from amino and hydroxy groups, the composition ratio is 1:2.4, the average degree of polymerisation is from 20 to 30 and the hydrolysis ratio is 0.7:9.3;

(xxix) m is from 6 to 16, $R^3$ is selected from amino and hydroxy groups, the composition ratio is 1:2.4, the average degree of polymerisation is from 20 to 30 and the hydrolysis ratio is 4.5:5.5;

(xxx) m is from 6 to 16, $R^3$ is selected from amino and hydroxy groups, the composition ratio is 1:2.4, the average degree of polymerisation is from 20 to 30 and the hydrolysis ratio is 1.4:8.6;

(xxxi) m is from 6 to 16, $R^3$ is selected from amino and hydroxy groups, the composition ratio is 1:2.4, the average degree of polymerisation is from 20 to 30 and the hydrolysis ratio is 0.7:9.3;

(xxxii) m is from 6 to 16, $R^3$ is selected from amino and hydroxy groups, the composition ratio is 1:2.4, the average degree of polymerisation is from 20 to 30 and the hydrolysis ratio is 0.8:9.2;

(xxxiii) m is from 6 to 16, $R^3$ is selected from amino and hydroxy groups, the composition ratio is 1:2.4, the average degree of polymerisation is from 20 to 30 and the hydrolysis ratio is 1.4:8.6;

(xxxiv) m is from 6 to 16, $R^3$ is selected from amino and hydroxy groups, the composition ratio is 1:3.1, the average degree of polymerisation is from 20 to 30 and the hydrolysis ratio is 0.7:9.3;

(xxxv) m is from 6 to 16, $R^3$ is selected from amino and hydroxy groups, the composition ratio is 1:2.4, the average degree of polymerisation is from 20 to 30 and the hydrolysis ratio is 0.9:9.1;

(xxxvi) m is from 6 to 16, $R^3$ is selected from amino and hydroxy groups, the composition ratio is 1:2.4, the average degree of polymerisation is from 20 to 30 and the hydrolysis ratio is 1.9:8.1;

(xxxvii) m is from 6 to 16, $R^3$ is selected from ethoxy and hydroxy groups, the composition ratio is about 1:3, the average degree of polymerisation is from 20 to 30 and the hydrolysis ratio is 3.1:6.9;

(xxxviii) m is from 6 to 16, $R^3$ is selected from amino and hydroxy groups, the composition ratio is 1:1, the hydrolysis ratio is 1.4:8.6 and the Stokes radius is 9.3 nm or less;

(xxxix) m is from 6 to 16, $R^3$ is selected from amino and hydroxy groups, the composition ratio is 1:1, the hydrolysis ratio is 1.4:8.6 and the Stokes radius is in the range of from 3.1 to 6.2 nm;

(xl) m is from 6 to 16, $R^3$ is selected from amino and hydroxy groups, the composition ratio is 1:1, the hydrolysis ratio is 1.4:8.6 and the Stokes radius is in the range of from 1.5 to 4.7 nm;

(xli) m is from 6 to 16, $R^3$ is selected from amino and hydroxy groups, the composition ratio is 1:1, the hydrolysis ratio is 1.4:8.6 and the Stokes radius is 3.1 nm or less;

(xlii) m is from 6 to 16, $R^3$ is selected from amino and hydroxy groups, the composition ratio is 1:1, the hydrolysis ratio is 1.4:8.6 and the Stokes radius is 7.8 nm or less;

(xliii) m is from 6 to 16, $R^3$ is selected from amino and hydroxy groups, the composition ratio is 1:1, the hydrolysis ratio is 1.4:8.6 and the Stokes radius is 6.2 nm or less; and (xliv) m is from 6 to 16, $R^3$ is selected from amino and hydroxy groups, the composition ratio is 1:1, the hydrolysis ratio is 1.4:8.6 and the Stokes radius is 4.7 nm or less.

(46) As noted above, another aspect of the present invention provides a copolymer or a pharmacologically acceptable salt thereof obtainable by subjecting one or more carboxylic anhydride moieties of formula (III) in a copolymer which contains, as constitutional units, (a) one or more structural units which may be the same or different from each other and which are represented by the formula (I) below:

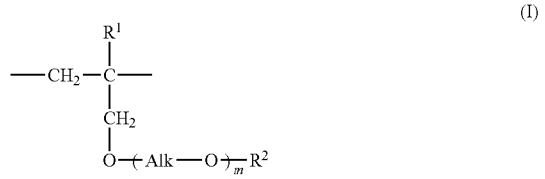

wherein:
m, Alk, $R^1$ and $R^2$ are as defined above, and (b) said structural unit comprising a carboxylic anhydride moiety of formula (III):

to one or more reactions selected from the group consisting of (i) hydrolysis, (ii) ammonolysis, (iii) aminolysis and (iv) alcoholysis.

Of these copolymers and pharmacologically acceptable salts thereof, preferred ones are:

(47) a copolymer or a pharmacologically acceptable salt thereof according to (46), wherein the structural unit represented by the formula (I) and the structural unit represented by the formula (III) in the copolymer are arranged in an alternating head-to-head sequence, an alternating head-to-tail sequence or an alternating mixed sequence of head-to-head and head-to-tail;

(48) a copolymer or a pharmacologically acceptable salt thereof according to according to (46), wherein the structural unit represented by the formula (I) and the structural unit represented by the formula (III) in the copolymer are arranged in random sequence;

(49) a copolymer or a pharmacologically acceptable salt thereof according to any one of (46) to (48), wherein Alk is an ethylene or trimethylene group;

(50) a copolymer or a pharmacologically acceptable salt thereof according to according to (49), wherein Alk is an ethylene group;

(51) a copolymer or a pharmacologically acceptable salt thereof according to any one of (46) to (50), wherein m is an integer of from 3 to 50;

(52) a copolymer or a pharmacologically acceptable salt thereof according to (51), wherein m is an integer of from 3 to 40;

(53) a copolymer or a pharmacologically acceptable salt thereof according to (52), wherein m is an integer of from 6 to 16 or 28 to 38;

(54) a copolymer or a pharmacologically acceptable salt thereof according to (53), wherein m is an integer of from 6 to 16;

(55) a copolymer or a pharmacologically acceptable salt thereof according to any one of (46) to (54), wherein $R^1$ is a hydrogen atom or a methyl group;

(56) a copolymer or a pharmacologically acceptable salt thereof according to (55), wherein $R^1$ is a hydrogen atom;

(57) a copolymer or a pharmacologically acceptable salt thereof according to any one of (46) to (56), wherein $R^2$ is a hydrogen atom or a methyl group;

(58) a copolymer or a pharmacologically acceptable salt thereof according to (57), wherein $R^2$ is a methyl group;

(59) a copolymer or a pharmacologically acceptable salt thereof according to any one of (46) to (58), wherein the ratio between the structural unit represented by the formula (I) and the structural unit obtained by subjecting one or more structural units of formula (III) to one or more reactions selected from the group consisting of (i) hydrolysis, (ii) ammonolysis, (iii) aminolysis and (iv) alcoholysis is in the range of from 10:1 to 1:10;

(60) a copolymer or a pharmacologically acceptable salt thereof according to (59), wherein the ratio between the structural unit represented by the formula (I) and the structural unit obtained by subjecting one or more structural units of formula (III) to one or more reactions selected from the group consisting of (i) hydrolysis, (ii) ammonolysis, (iii) aminolysis and (iv) alcoholysis is in the range of from 3:1 to 1:8;

(61) a copolymer or a pharmacologically acceptable salt thereof according to (59), wherein the ratio between the structural unit represented by the formula (I) and the structural unit obtained by subjecting one or more structural units of formula (III) to one or more reactions selected from the group consisting of (i) hydrolysis, (ii) ammonolysis, (iii) aminolysis and (iv) alcoholysis is in the range of from 2:1 to 1:2 or 1:2 to 1:6;

(62) a copolymer or a pharmacologically acceptable salt thereof according to (59), wherein the ratio between the structural unit represented by the formula (I) and the structural unit obtained by subjecting one or more structural units of formula (III) to one or more reactions selected from the group consisting of (i) hydrolysis, (ii) ammonolysis, (iii) aminolysis and (iv) alcoholysis is 1:1 or in the range of from 1:2 to 1:4;

(63) a copolymer or a pharmacologically acceptable salt thereof according to any one of (46) to (62), wherein the average degree of polymerization is in the range of from 5 to 200;

(64) a copolymer or a pharmacologically acceptable salt thereof according to (63), wherein the average degree of polymerization is in the range of from 5 to 50;

(65) a copolymer or a pharmacologically acceptable salt thereof according to (64), wherein the average degree of polymerization is in the range of from 5 to 20;

(66) a copolymer or a pharmacologically acceptable salt thereof according to (63), wherein the average degree of polymerization is in the range of from 20 to 30;

(67) a copolymer or a pharmacologically acceptable salt thereof according to (63), wherein the average degree of polymerization is in the range of from 30 to 40;

(68) a copolymer according or a pharmacologically acceptable salt thereof according to (46)

wherein:
  m is an integer of from 3 to 100,
  Alk represents an alkylene group having from 1 to 6 carbon atoms, and
  $R^1$ and $R^2$ are the same or different and each represents a hydrogen atom or an alkyl group having from 1 to 6 carbon atoms;

(69) a copolymer or a pharmacologically acceptable salt thereof according to any one of (46) to (68), which is obtainable by subjecting a carboxylic anhydride moiety of formula (III) in the copolymer to ammonolysis;

(70) a copolymer or a pharmacologically acceptable salt thereof according to (69), which is obtainable by carrying out the ammonolysis with ammonia water;

(71) a copolymer or a pharmacologically acceptable salt thereof according to any one of (46) to (68), which is obtainable by subjecting a carboxylic anhydride moiety of formula (III) in the copolymer to aminolysis;

(72) a copolymer or a pharmacologically acceptable salt thereof according to (71), which is obtainable by carrying out the aminolysis using an aqueous dimethylamine solution;

(73) a copolymer or a pharmacologically acceptable salt thereof according to any one of (46) to (68), which is obtainable by subjecting a carboxylic anhydride moiety of formula (III) in the copolymer to alcoholysis; and

(74) a copolymer or a pharmacologically acceptable salt thereof according to (73), which is obtainable by carrying out the alcoholysis using ethanol.

The present invention also makes use of the copolymers and pharmacologically acceptable salts thereof of the present invention to provide a pharmaceutical composition, a modifier capable of modifying a protein, a complex, a method for prolonging the time that a protein is retained in the bloodstream, a method for the treatment or prophylaxis of diseases and a use of the complex of the invention for the manufacture of a medicament for the treatment or prophylaxis of diseases. Preferred examples of aspects of these inventions include:

(75) a pharmaceutical composition comprising a pharmaceutically acceptable diluent or carrier and at least one copolymer or a pharmacologically acceptable salt thereof of the present invention according to any one of (1) to (74);

(76) a pharmaceutical composition according to (75), wherein said composition further comprises at least one protein or an analogue or variant thereof;

(77) a pharmaceutical composition according to (76), wherein the protein or an analogue or variant thereof is a basic protein;

(78) a pharmaceutical composition according to (77), wherein the basic protein is a basic fibroblast growth factor (bFGF), an epidermal growth factor (EGF), an osteoclastogenesis inhibitory factor (OCIF), a platelet-derived growth factor (PDGF), a brain-derived neurotrophic factor (BDNF), a nerve growth factor (NGF), a human growth hormone (HGH), a hepatocyte growth factor (HGF), or a vascular endothelial growth factor (VEGF), or an analogue or a variant thereof;

(79) a pharmaceutical composition according to (77), wherein the basic protein is an osteoclastogenesis inhibitory factor (OCIF) or an analogue or a variant thereof;

(80) a pharmaceutical composition according to (79), wherein said OCIF or an analogue or variant thereof is natural type or recombinant type OCIF;

(81) a pharmaceutical composition according to (79), wherein said OCIF or an analogue or variant thereof is a monomer or a dimer;

(82) a pharmaceutical composition according to (79), wherein said OCIF is a monomer of human OCIF having a molecular weight as measured by SDS-PAGE under non-reducing conditions of about 60000 or a dimer of human OCIF having a molecular weight of about 120000 as measured by SDS-PAGE under non-reducing conditions;

(83) a pharmaceutical composition according to (79), wherein said OCIF comprises amino acids −21 to +380 of SEQ. ID. NO.1 of the sequence listing;

(84) a pharmaceutical composition according to (79), wherein said OCIF comprises amino acids +1 to +380 of SEQ. ID. NO.1 of the sequence listing;

(85) a modifier capable of modifying a protein or an analogue or variant thereof, said modifier comprising the copolymer or a pharmacologically acceptable salt thereof according to any one of (1) to (74);

(86) a modifier capable of modifying a protein or an analogue or variant thereof according to (85), wherein the protein is a basic protein;

(87) a modifier capable of modifying a protein or an analogue or variant thereof according to (86), wherein the basic protein is a basic fibroblast growth factor (bFGF), an epidermal growth factor (EGF), an osteoclastogenesis inhibitory factor (OCIF), a platelet-derived growth factor (PDGF), a brain-derived neurotrophic factor (BDNF), a nerve growth factor (NGF), a human growth hormone (HGH), a hepatocyte growth factor (HGF), or a vascular endothelial growth factor (VEGF), or an analogue or a variant thereof;

(88) a modifier capable of modifying a protein or an analogue or variant thereof according to (86), wherein the basic protein is an osteoclastogenesis inhibitory factor (OCIF) or an analogue or a variant thereof;

(89) a modifier capable of modifying a protein or an analogue or variant thereof according to (88), wherein said OCIF or an analogue or variant thereof is natural type or recombinant type OCIF;

(90) a modifier capable of modifying a protein or an analogue or variant thereof according to (88), wherein said OCIF or an analogue or variant thereof is a monomer or a dimer;

(91) a modifier capable of modifying a protein or an analogue or variant thereof according to (88), wherein said OCIF is a monomer of human OCIF having a molecular weight as measured by SDS-PAGE under non-reducing conditions of about 60000 or a dimer of human OCIF having a molecular weight of about 120000 as measured by SDS-PAGE under non-reducing conditions;

(92) a modifier capable of modifying a protein or an analogue or variant thereof according to (88), wherein said OCIF comprises amino acids −21 to +380 of SEQ. ID. NO.1 of the sequence listing;

(93) a modifier capable of modifying a protein or an analogue or variant thereof according to (88), wherein said OCIF comprises amino acids +1 to +380 of SEQ. ID. NO.1 of the sequence listing;

(94) a complex comprising at least one protein or an analogue or variant thereof which is bound to at least one copolymer or a pharmacologically acceptable salt thereof according to any one of (1) to (74);

(95) a complex according to (94), wherein the protein is a basic protein;

(96) a complex according to (95), wherein the basic protein is a basic fibroblast growth factor (bFGF), an epidermal growth factor (EGF), an osteoclastogenesis inhibitory factor (OCIF), a platelet-derived growth factor (PDGF), a brain-derived neurotrophic factor (BDNF), a nerve growth factor (NGF), a human growth hormone (HGH), a hepatocyte growth factor (HGF), or a vascular endothelial growth factor (VEGF), or an analogue or a variant thereof;

(97) a complex according to (95), wherein the basic protein is an osteoclastogenesis inhibitory factor (OCIF) or an analogue or a variant thereof;

(98) a complex according to (97), wherein said OCIF or an analogue or variant thereof is natural type or recombinant type OCIF;

(99) a complex according to (97), wherein said OCIF or an analogue or variant thereof is a monomer or a dimer;

(100) a complex according to (97), wherein said OCIF is a monomer of human OCIF having a molecular weight as measured by SDS-PAGE under non-reducing conditions of about 60000 or a dimer of human OCIF having a molecular weight of about 120000 as measured by SDS-PAGE under non-reducing conditions;

(101) a complex according to (97), wherein said OCIF comprises amino acids −21 to +380 of SEQ. ID. NO.1 of the sequence listing;

(102) a complex according to (97), wherein said OCIF comprises amino acids +1 to +380 of SEQ. ID. NO. 1 of the sequence listing;

(103) a pharmaceutical composition comprising an effective amount of a pharmacologically active agent together with a carrier or diluent therefor, wherein said pharmacologically active agent is in the form of a complex according to any one of (94) to (102);

(104) a method for prolonging the time that a protein or an analogue or variant thereof is retained in the bloodstream after administration to a patient by complexing said protein or an analogue or variant thereof with at least one copolymer or a pharmacologically acceptable salt thereof according to any one of (1) to (74);

(105) a method according to (104), wherein the protein is a basic protein;

(106) a method according to (105), wherein the basic protein is a basic fibroblast growth factor (bFGF), an epidermal growth factor (EGF), an osteoclastogenesis inhibitory factor (OCIF), a platelet-derived growth factor (PDGF), a brain-derived neurotrophic factor (BDNF), a nerve growth factor (NGF), a human growth hormone (HGH), a hepatocyte growth factor (HGF), or a vascular endothelial growth factor (VEGF), or an analogue or a variant thereof;

(107) a method according to (105), wherein the basic protein is an osteoclastogenesis inhibitory factor (OCIF) or an analogue or a variant thereof;

(108) a method according to (107), wherein said OCIF or an analogue or variant thereof is natural type or recombinant type OCIF;

(109) a method according to (107), wherein said OCIF or an analogue or variant thereof is a monomer or a dimer;

(110) a method according to (107), wherein said OCIF is a monomer of human OCIF having a molecular weight as measured by SDS-PAGE under non-reducing conditions of about 60000 or a dimer of human OCIF having a molecular weight of about 120000 as measured by SDS-PAGE under non-reducing conditions;

(111) a method according to (107), wherein said OCIF comprises amino acids −21 to +380 of SEQ. ID. NO.1 of the sequence listing;

(112) a method according to (107), wherein said OCIF comprises amino acids +1 to +380 of SEQ. ID. NO.1 of the sequence listing;

(113) a method for the treatment or prophylaxis of a disease in a patient that is susceptible to a protein or an analogue or variant thereof comprising administering to said patient an effective amount of a complex comprising said protein or an analogue or variant thereof which is bound to at least one copolymer or a pharmacologically acceptable salt thereof according to any one of (1) to (74);

(114) a method according to (113), wherein the protein is a basic protein;

(115) a method according to (114), wherein the basic protein is a basic fibroblast growth factor (bFGF), an epidermal growth factor (EGF), an osteoclastogenesis inhibitory factor (OCIF), a platelet-derived growth factor (PDGF), a brain-derived neurotrophic factor (BDNF), a nerve growth factor (NGF), a human growth hormone (HGH), a hepatocyte growth factor (HGF), or a vascular endothelial growth factor (VEGF), or an analogue or a variant thereof;

(116) a method according to (114), wherein the basic protein is an osteoclastogenesis inhibitory factor (OCIF) or an analogue or a variant thereof;

(117) a pharmaceutical composition according to (116), wherein said OCIF or an analogue or variant thereof is natural type or recombinant type OCIF;

(118) a method according to (116), wherein said OCIF or an analogue or variant thereof is a monomer or a dimer;

(119) a method according to (116), wherein said OCIF is a monomer of human OCIF having a molecular weight as measured by SDS-PAGE under non-reducing conditions of about 60000 or a dimer of human OCIF having a molecular weight of about 120000 as measured by SDS-PAGE under non-reducing conditions;

(120) a method according to (116), wherein said OCIF comprises amino acids −21 to +380 of SEQ. ID. NO.1 of the sequence listing;

(121) a method according to (116), wherein said OCIF comprises amino acids +1 to +380 of SEQ. ID. NO.1 of the sequence listing;

(122) a method according to any one of (116) to (121), wherein said disease is a bone metabolic disease;

(123) use of complex comprising a protein or an analogue or variant thereof which is bound to at least one copolymer or a pharmacologically acceptable salt thereof according to any one of (1) to (74) in the manufacture of a medicament for the prophylaxis or treatment of a disease susceptible to said protein or an analogue or variant thereof;

(124) use according to (122), wherein the protein is a basic protein;

(125) use according to (123), wherein the basic protein is a basic fibroblast growth factor (bFGF), an epidermal growth factor (EGF), an osteoclastogenesis inhibitory factor (OCIF), a platelet-derived growth factor (PDGF), a brain-derived neurotrophic factor (BDNF), a nerve growth factor (NGF), a human growth hormone (HGH), a hepatocyte growth factor (HGF), or a vascular endothelial growth factor (VEGF), or an analogue or a variant thereof;

(126) use according to (123), wherein the basic protein is an osteoclastogenesis inhibitory factor (OCIF) or an analogue or a variant thereof;

(127) use according to (126), wherein said OCIF or an analogue or variant thereof is natural type or recombinant type OCIF;

(128) use according to (126), wherein said OCIF or an analogue or variant thereof is a monomer or a dimer;

(129) use according to (126), wherein said OCIF is a monomer of human OCIF having a molecular weight as measured by SDS-PAGE under non-reducing conditions of about 60000 or a dimer of human OCIF having a molecular weight of about 120000 as measured by SDS-PAGE under non-reducing conditions;

(130) use according to (126), wherein said OCIF comprises amino acids −21 to +380 of SEQ. ID. NO.1 of the sequence listing;

(131) use according to (126), wherein said OCIF comprises amino acids +1 to +380 of SEQ. ID. NO.1 of the sequence listing; and (132) use according to any one of (126) to (131), wherein said disease is a bone metabolic disease.

The "alkylene group having from 1 to 6 carbon atoms" in the definition of substituent Alk in formula (I) above is a straight- or branched-chain alkylene group having from 1 to 6 carbon atoms such as a methylene, methylmethylene, ethylene, propylene, trimethylene, tetramethylene, 1-methyltrimethylene, 2-methyltrimethylene, 3-methyltrimethylene, pentamethylene or hexamethylene group. Among these alkylene groups, straight- or branched-chain alkylene groups having 1 to 4 carbon atoms are preferred, ethylene or trimethylene groups are more preferred and an ethylene group is most preferred.

The alkyl group in the "alkyl group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below" in the definition of substituents $R^1$, $R^2$, $R^4$, $R^5$ and Substituents A in formulae (I) and (II) above is a straight- or branched-chain alkyl group having from 1 to 6 carbon atoms such as a methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group. Among these alkyl groups, straight- or branched-chain alkyl groups having 1 to 4 carbon atoms are preferred, methyl and ethyl groups are more preferred and a methyl group is most preferred.

The alkoxy group in the "alkoxy group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below" in the definition of substituent $R^3$ and Substituents A in formulae (I) and (II) above is a substituent in which the above-mentioned alkyl group having from 1 to 6 carbon atoms is bound to an oxygen atom. Examples of such an alkoxy group include straight- or branched-chain alkoxy groups having 1 to 6 carbon atoms such as a methoxy, ethoxy, n-propoxy, isopropoxy, n-butoxy, isobutoxy, s-butoxy, tert-butoxy, n-pentyloxy, isopentyloxy, 2-methylbutoxy, neopentyloxy, n-hexyloxy, 4-methylpentyloxy, 3-methylpentyloxy, 2-methylpentyloxy, 3,3-dimethylbutoxy, 2,2-dimethylbutoxy, 1,1-dimethylbutoxy, 1,2-dimethylbutoxy, 1,3-dimethylbutoxy, and 2,3-dimethylbutoxy groups. Among these alkoxy groups, straight- or branched-chain alkoxy groups having from 1 to 4 carbon atoms are more preferred and an ethoxy group is most preferred.

The "halogen atom" that is one of the "Substituents A" above, is an optional substituent on the "alkyl group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below" in the definition of substituents $R^1$, $R^2$, $R^4$ and $R^5$ in formulae (I) and (II) above and is an optional substituent on the "alkoxy group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below" in the definition of substituent $R^3$ in formula (II) above is a fluorine atom, a chlorine atom, a bromine atom or an iodine atom; and preferably it is a fluorine atom or a chlorine atom.

The "aryl group having from 6 to 14 carbon atoms" that is an optional substituent on the "alkyl group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below" in the definition of substituents $R^1$, $R^2$, $R^4$ and $R^5$ and an optional substituent on the "alkoxy group having from 1 to 6 carbon atoms that may optionally be substituted with at least one substituent selected from the group consisting of hydroxy groups, halogen atoms and aryl groups having from 6 to 14 carbon atoms" in the definition of substituent $R^3$ in formula (II) above is an aromatic hydrocarbon group having from 6 to 14 carbon atoms and may be, for example, a phenyl, indenyl, naphthyl, phenanthryl or anthryl group. Preferably it is a phenyl group.

The "aryloxy group having from 6 to 14 carbon atoms that may optionally be substituted with from 1 to 5 substituents selected from Substituents A" in the definition of substituent $R^3$ in formula (II) above is an aryl group as defined above that is bonded to an oxygen atom and may be, for example, a phenoxy, indenyloxy, naphthyloxy, phenanthryloxy or anthryloxy group. Preferably it is a phenoxy group.

The "alkyl group having from 1 to 6 carbon atoms that is optionally substituted with at least one halogen atom" in the definition of substituents $R^1$, $R^2$, $R^4$ and $R^5$ in formulae (I) and (II) above is an alkyl group having from 1 to 6 carbon atoms as described above that is substituted with at least one halogen atom as described above and may be, for example, a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, a 2-bromoethyl group, a 2-chloroethyl group, a 2-fluoroethyl group, a 2-iodoethyl group, a 3-chloropropyl group, a 4-fluorobutyl group, a 6-iodohexyl group, a 2,2-dibromoethyl group or a pentafluoroethyl group. Preferably it is a trifluoromethyl group, a trichloromethyl group, a difluoromethyl group or a pentafluoroethyl group; and most preferably it is a trifluoromethyl group.

Examples of the "alkyl group having from 1 to 6 carbon atoms that is optionally substituted with at least one hydroxy group" in the definition of substituents $R^1$, $R^4$ and $R^5$ in formulae (I) and (II) above include a hydroxymethyl group, a 1-hydroxyethyl group, a 1-hydroxypropyl group and a 2-hydroxypropyl group.

The "alkoxy group having from 1 to 6 carbon atoms that is optionally substituted with at least one halogen atom" in the definitions of substituent $R^3$ in formula (II) above is an alkoxy group having from 1 to 6 carbon atoms as described above that is substituted with at least one halogen atom as described above and may be, for example, a trifluoromethoxy group, a trichloromethoxy group, a difluoromethoxy group, a dichloromethoxy group, a dibromomethoxy group, a fluoromethoxy group, a 2,2,2-trifluoroethoxy group, a 2,2,2-trichloroethoxy group, a 2-bromoethoxy group, a 2-chloroethoxy group, a 2-fluoroethoxy group, a 2-iodoethoxy group, a 3-chloropropoxy group, a 4-fluorobutoxy group, a 6-iodohexyloxy group, a 2,2-dibromoethoxy group or a pentafluoroethoxy group; preferably it is a $C_1$-$C_4$ alkoxy group substituted with fluorine or chlorine atoms such as a trifluoromethoxy group, a trichloromethoxy group, a difluoromethoxy group or a pentafluoroethoxy group. More preferably it is a trifluoromethoxy group.

Examples of the "alkoxy group having from 1 to 6 carbon atoms that is optionally substituted with at least one hydroxy group" in the definition of substituent $R^3$ in formula (II) above include a hydroxymethoxy group, a 1-hydroxyethoxy group, a 1-hydroxypropoxy group and a 2-hydroxypropoxy group.

The "alkyl group having from 1 to 6 carbon atoms that is optionally substituted with at least one aryl group having from 6 to 14 carbon atoms that may optionally be substituted with from 1 to 5 substituents selected from Substituents A" in the definition of substituents $R^1$, $R^2$, $R^4$ and $R^5$ in formulae (I) and (II) above may be, for example, a benzyl group, an 1-naphthylmethyl group, a 2-naphthylmethyl group, an indenylmethyl group, a 1-phenethyl group, a 2-phenethyl group, a 1-naphthylethyl group, a 2-naphthylethyl group, a 1-phenylpropyl group, a 2-phenylpropyl group, a 3-phenylpropyl group, a 1-naphthylpropyl group, a 2-naphthylpropyl group, a 3-naphthylpropyl group, a 1-phenylbutyl group, a 2-phenylbutyl group, a 3-phenylbutyl group, a 4-phenylbutyl group, a 1-naphthylbutyl group, a 2-naphthylbutyl group, a 3-naphthylbutyl group, a 4-naphthylbutyl group, a 1-phenylpentyl group, a 2-phenylpentyl group, a 3-phenylpentyl group, a 4-phenylpentyl group, a 5-phenylpentyl group, a 1-phenylhexyl group, a 2-phenylhexyl group, a 3-phenylhexyl group, a 4-phenylhexyl group, a 5-phenylhexyl group or a 6-phenylhexyl group; preferably it is an alkyl group substituted with an aryl group having from 6 to 10 carbon atoms such as a benzyl group, an 1-naphthylmethyl group, a 2-naphthylmethyl group, a 1-phenethyl group, a 2-phenethyl group, a 1-naphthylethyl group, a 2-naphthylethyl group, a 1-phenylpropyl group, a 2-phenylpropyl group, a 3-phenylpropyl group or a 1-naphthylpropyl group; and more preferably it is a benzyl group.

The "alkoxy group having from 1 to 6 carbon atoms that is optionally substituted with at least one aryl group having from 6 to 14 carbon atoms that may optionally be substituted with from 1 to 5 substituents selected from Substituents A" in the definition of substituent $R^3$ in formulae (II) above may be, for example, a benzoxy group, a 1-naphthylmethoxy group, a 2-naphthylmethoxy group, an indenylmethoxy group, a 1-phenethoxy group, a 2-phenethoxy group, a 1-naphthylethoxy group, a 2-naphthylethoxy group, a 1-phenylpropoxy group, a 2-phenylpropoxy group, a 3-phenylpropoxy group, a 1-naphthylpropoxy group, a 2-naphthylpropoxy group, a 3-naphthylpropoxy group, a 1-phenylbutoxy group, a 2-phenylbutoxy group, a 3-phenylbutoxy group, a 4-phenylbutoxy group, a 1-naphthylbutoxy group, a 2-naphthylbutoxy group, a 3-naphthylbutoxy group, a 4-naphthylbutoxy group, a 1-phenylpentoxy group, a 2-phenylpentoxy group, a 3-phenylpentoxy group, a 4-phenylpentoxy group, a 5-phenylpentoxy group, a 1-phenylhexyloxy group, a 2-phenylhexyloxy group, a 3-phenylhexyloxy group, a 4-phenylhexyloxy group, a 5-phenylhexyloxy group or a 6-phenylhexyloxy group; preferably it is an alkyl group substituted with an aryl group having from 6 to 10 carbon atoms such as a benzoxy group, an 1-naphthylmethoxy group, a 2-naphthylmethoxy group, a 1-phenethoxy group, a 2-phenethoxy group, a 1-naphthylethoxy group, a 2-naphthylethoxy group, a 1-phenylpropoxy group, a 2-phenylpropoxy group, a 3-phenylpropoxy group or a 1-naphthylpropoxy group; and more preferably it is a benzoxy group.

Where $R^3$ is an "aryloxy group having from 6 to 14 carbon atoms that may optionally be substituted with from 1 to 5 substituents selected from Substituents A", it is preferably an aryloxy group having from 6 to 10 carbon atoms that is optionally substituted with from 1 to 3 substituents selected from Substituent Group A; more preferably, it is a phenoxy group that is optionally substituted with from 1 to 3 substituents selected from Substituent Group A; still more preferably, it is a phenoxy group optionally substituted with from 1 to 3 halogen atoms, alkyl groups having from 1 to 6 carbon atoms, hydroxy groups or nitro groups; and, most preferably, it is a phenoxy group or a p-nitrophenoxy group.

Where the copolymer of the present invention has a basic group, the compound can be converted to a pharmacologically acceptable salt thereof by reacting some or all of these basic groups with an acid. Furthermore, the copolymers of the present invention have acidic carboxyl groups and the copolymer can be converted to a pharmacologically acceptable salt thereof by reacting some or all of these carboxyl groups with a base.

Preferred examples of the pharmacologically acceptable salts formed with a basic group present in the copolymers of the present invention include inorganic acid salts such as hydrohalogenated acid salts (e.g. hydrochlorides, hydrobromides and hydroiodides), nitrates, perchlorates, sulfates and phosphates; organic acid salts such as lower alkanesulfonates in which the lower alkyl moiety thereof is as defined above (e.g. methanesulfonates, trifluoromethanesulfonates and ethanesulfonates), arylsulfonates in which the aryl moiety thereof is as defined above (e.g. benzenesulfonate or p-toluenesulfonate), acetates, malates, fumarates, succinates, citrates, ascorbates, tartrates, oxalates and maleates; and amino acid salts such as glycine salts, lysine salts, arginine salts, ornithine salts, glutamates and aspartates. Hydrohalogenated acid salts are particularly preferred.

Preferred examples of the pharmacologically acceptable salts formed with an acidic carboxyl group present in the copolymers of the present invention include metal salts such as alkali metal salts (e.g. sodium salts, potassium salts and lithium salts), alkali earth metal salts (e.g. calcium salts and magnesium salts), metal salts such as aluminium salts, iron salts zinc salts, copper salts, nickel salts and cobalt salts; amine salts such as inorganic amine salts (e.g. ammonium salts) and organic amine salts (e.g. t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts and tris(hydroxymethyl)aminomethane salts; and amino acid salts such as glycine salts, lysine salts, arginine salts, ornithine salts, glutamates and aspartates. Alkali metal salts and alkali earth metal salts are particularly preferred.

In the present invention, the "structural unit" is defined as a minimum constitutional unit of the copolymer of the invention and is depicted in the definition of the copolymer above as a unit of formula (I) or a unit of formula (II). The "structural unit" is not the structure of a monomer starting material used in a polymerization reaction in the synthesis of a copolymer of the present invention; rather, it is the unit that is derived from said monomer starting material and is present in said copolymer of the present invention.

In the present invention, the phrase "head-to-head sequence" means that the structural units represented by the formulae (I) and (II) are arranged as shown by the following formula:

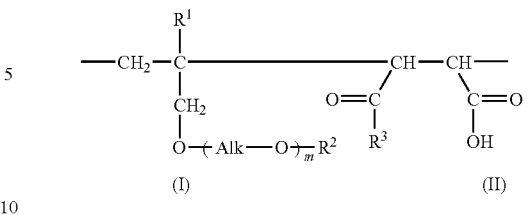

In the present invention, the phrase "head-to-tail sequence" means that the structural units represented by the formulae (I) and (II) are arranged as shown by the following formula:

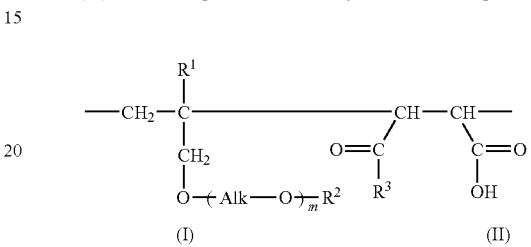

In the present invention, the copolymers and pharmacologically acceptable salts thereof may be alternating copolymers or random copolymers. Alternating copolymers are those in which the ratio of the structural units of formula (I) to the structural units of formula (II) is 1:1 and the structural units represented by the formula (I) and the structural units represented by the formula (II) are arranged in an alternating head-to-head sequence, an alternating head-to-tail sequence or an alternating mixed sequence of head-to-head and head-to-tail. Random copolymers are those in which the structural units represented by the formula (I) and the structural units represented by the formula (II) are arranged in a random sequence.

In the present invention, the "composition ratio" is the average ratio of the number of structural units represented by formula (I) to the number of structural units represented by formula (II) in a copolymer of the present invention. When a copolymer is substantially an alternating copolymer, the composition ratio will be 1:1. When a copolymer is a random copolymer, however, said ratio can be varied. In the copolymers of the present invention, said ratio is not particularly limited, and typically it might be in a range of from 10:1 to 1:10; preferably from 3:1 to 1:8, more preferably from 2:1 to 1:2 or 1:2 to 1:6, and most preferably it is either 1:1 or from 1:2 to 1:4. It should be noted that the composition ratio values inevitably vary somewhat depending on slight changes in starting materials, polymerisation conditions and the like. As a result, the composition ratios given are approximate values; variations of up to +30% on the values for the composition ratios given above are still considered to be within the scope of said ratios.

The composition ratio of the copolymers of the present invention can be determined by using known analytical techniques. By determining the carboxyl group content of the copolymer (mmol/g) by conductometric titration [the determination requiring the preparation of the corresponding completely hydrolysed copolymer (i.e. $R^3$ is OH), either by hydrolysing the copolymer being analysed or by synthesising the corresponding hydrolysed copolymer separately] and from a knowledge of the formula weights of each of the structural units of said copolymer, it is possible to determine the composition ratio using the following formula:

$$Rii/Ri = (C \times FWi)/(2000 - C \times FWii)$$

wherein $R^1$ is the average number of structural units (I), Rii is the average number of structural units (II), C is the carboxyl group content of the copolymer (mmol/g), FWi is the formula weight of the structural unit (I) and FWii is the formula weight of the structural unit (II).

Generally, the molecular weight of a polymer is determined as a relative molecular weight against that of a standard compound which contains a similar structure to that of said polymer and has a known absolute molecular weight value. Such an evaluation method is often used in the determination of the molecular weight of novel copolymers such as those of present invention.

The average molecular weight of the copolymer of present invention is the value measured by gel filtration chromatography using a polymer having known absolute molecular weight as a standard compound. The nature of the gel, the elution conditions and the polymer of known absolute molecular weight used as the comparison can be appropriately chosen by the person of ordinary skill using known techniques and general knowledge, e.g. see "Comprehensive Polymer Science", pub. Pergamon Press (Oxford) 1989. The standard compound used for comparison purposes is preferably a polymer having a similar structure and properties. For the copolymers of the present invention, the side chain portion is considered to be a characteristic structure. Therefore, the standard compound used for comparison is preferably a polymer containing a similar structure to that of the side chain portion of the copolymer of the present invention whose average molecular weight is to be measured. More preferably the standard compound used is a poly(ethylene glycol).

In the present invention, the "average degree of polymerization" is an average value of the degree of polymerization of the structural units in the copolymer of the present invention, i.e. it is the average number of structural units in said copolymer. It is determined on the basis of the average molecular weight of the copolymer, the formula weights of each of the structural units of said copolymer and the composition ratio of the structural units of said copolymer. The "average degree of polymerisation" of a copolymer of the present invention having structural units I and II can be calculated using the following formula:

$$\text{Average degree of polymerisation} = Mc/(FWi \times Ri + FWii \times Rii)$$

wherein Mc is the average molecular weight of the copolymer, Fwi and Fwii are the formula weights for each of the structural units I and II respectively and $R^1$ and Rii represent the proportions of structural units I and II in the copolymer calculated from the composition ratio (composition ratio=Ri: Rii; Ri+Rii=1).

In the above formula for determining the average degree of polymerisation of a copolymer of the present invention, the value of the composition ratio of the structural units, the average molecular weight of the copolymer and the formula weights of the structural units can all be determined as discussed above. In order to do so, it is necessary to prepare the corresponding completely hydrolysed, ammonolysed, aminolysed or alcoholysed copolymer (preferably the corresponding completely hydrolysed copolymer). Alternatively, if the starting copolymer used in the preparation of the copolymer of the present invention is of known composition, these values can be determined without the need for analysis.

The average degree of polymerization in the copolymers of the present invention is not particularly limited. Typically, it is in a range of from 5 to 200; preferably it is from 5 to 50; more preferably from 5 to 20 or 20 to 30 or 30 to 40.

In the copolymers of the present invention, the structural units of formula (II) can comprise at least one structural unit of formula (II) wherein $R^3$ is an optionally substituted alkoxy group having from 1 to 6 carbon atoms, an optionally substituted aryloxy group or a group represented by the formula $-NR^4R^5$ and optionally at least one structural unit represented by the formula (II) in which $R^3$ is a hydroxyl group. The ratio between the structural units represented by the formula (II) in which $R^3$ is a hydroxy group and the structural units represented by the formula (II) in which $R^3$ is an optionally substituted alkoxy group, an optionally substituted aryloxy group or a group represented by the formula $-NR^4R^5$ is referred to as the hydrolysis ratio. By determining the carboxyl group content of the copolymer (mmol/g) by conductometric titration and from a knowledge of the formula weights of each of the structural units of said copolymer and the composition ratio (see above), it is possible to determine the hydrolysis ratio H:A using the following formula:

$$A = \frac{2000 \times (Rii/Ri) - C \times [FWi + FWii \times (Rii/Ri)]}{(Rii/Ri) \times [C \times (FW(A)ii - FWii) + 1000]} H + A$$

wherein H:A is the hydrolysis ratio, Ri:Rii is the composition ratio, C is the carboxyl group content of the copolymer (mmol/g), FWi is the formula weight of the structural unit (I), FWii is the formula weight of the structural unit (II) wherein $R^3$ is OH and FW(A)ii is the formula weight of the structural unit (II) wherein R is an optionally substituted alkoxy group, an optionally substituted aryloxy group or a group represented by the formula $-NR^4R^5$.

Preferred ranges for the hydrolysis ratio are 5:5 to 0:10, 4:6 to 0:10, 3:7 to 0:10, 2:8 to 0:10 and 1:9 to 0:10. It should be noted that the hydrolysis ratio values inevitably vary somewhat depending on slight changes in starting materials, reaction conditions and the like. As a result, the hydrolysis ratios stated in the present application are approximate values; variations of up to ±30% on the values for the hydrolysis ratios stated in the present application are still considered to be within the scope of said ratios.

The molecular size of the copolymers of the invention can be measured using known analytical techniques such as size exclusion chromatography using proteins of known molecular size as standards (Examples 15 and 16 below provide examples of the use of such a technique). Using size exclusion chromatography, the molecular size of a copolymer is given as its Stokes radius. In the present invention, the molecular size of the copolymers is not particularly limited. Typically, the Stokes radius of the copolymers of the present invention is 9.3 nm or less, preferably it is 7.3 nm or less, more preferably it is 6.2 nm or less, 4.7 nm or less or 3.1 nm or less, or it is in a range of from 3.1 to 6.2 nm or 1.5 to 4.7 nm.

The copolymers and pharmacologically acceptable salts thereof of the present invention can be obtained by a suitable copolymerization reaction known to those skilled in the art [see, for example, "Comprehensive Polymer Science" published by Pergamon Press (Oxford) in 1989] using starting monomers represented by the following formulae (IV) and (V):

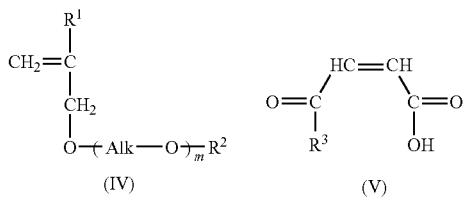

(wherein m, Alk, and $R^1$, $R^2$ and $R^3$ are as defined above). In order to obtain a copolymer having a particular desired average degree of polymerization or molecular weight, the obtained copolymer may be fractionated using gel filtration chromatography.

The monomers are known in the art or can easily be obtained according to a method well known to those skilled in the art [see, for example, J. M. Harris, "Laboratory synthesis of polyethylene glycol derivatives", Rev. Macromol. Chem. Phys. C25, 326-373 (1985) and Japanese Patent No. 2621308]. Monomers represented by the formula (V) can be easily obtained by subjecting maleic anhydride to one or more reactions selected from the group consisting of (a) hydrolysis, (b) ammonolysis, (c) aminolysis and (d) alcoholysis.

Alternatively, a copolymer or a pharmacologically acceptable salt thereof can be obtained by subjecting one or more carboxylic anhydride moieties of formula (III) in a copolymer which contains, as constitutional units, (a) one or more structural units which may be the same or different from each other and which are represented by the formula (I) below:

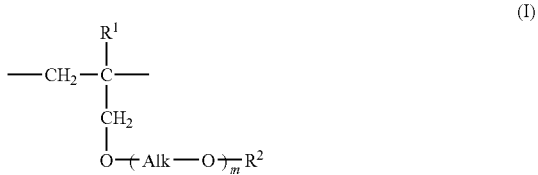

wherein:
m, Alk, $R^1$ and $R^2$ are as defined above, and (b) said structural unit comprising a carboxylic anhydride moiety of formula (III):

to one or more reactions selected from the group consisting of (i) hydrolysis, (ii) ammonolysis, (iii) aminolysis and (iv) alcoholysis. The starting copolymers having units of formulae (I) and (III) are either well known in the art (for example, copolymers such as AM-0530K and AM-1510K can be purchased from NOF Corporation) or can be easily prepared according to a method well known to those skilled in the art [see, for example, Yoshimoto et al., "Polyethylene glycol derivative-modified cholesterol oxidase soluble and active in benzene", Biochem. Biophys. Res. Comm. 148, 876-882 (1987), Japanse Patent No 2621308, Japanese Patent Application Publication No. 2003-105040 and Japanese Patent Application Publication No. 2003-105003].

To obtain a copolymer having a desired average degree of polymerazation or desired molecular weight, the obtained copolymer may be fractionated by gel filtration chromatography.

In the present invention, copolymers of the present invention can be obtained by subjecting one or more carboxylic anhydride moieties of formula (III) to one or more reactions selected from the group consisting of (i) hydrolysis, (ii) ammonolysis, (iii) aminolysis and (iv) alcoholysis.

In the present invention, "hydrolysis" means a ring opening reaction of a carboxylic anhydride moiety of formula (III) with water to give a structural unit of formula (II) wherein $R^3$ is a hydroxy group. The nature of the actual hydrolysis reaction is not particularly limited as long as it is a method commonly employed by those skilled in the art.

Examples of a suitable solvent to be used in the hydrolysis reaction include: water; ethers such as diethyl ether, diisopropyl ether, tetrahydrofuran, dioxane, dimethoxyethane, and diethylene glycol dimethyl ether; and amides such as formamide, N,N-dimethylformamide, N,N-dimethylacetamide, N-methyl-2-pyrrolidone, N-methylpyrrolidinone, and hexamethylphosphorotriamide. Of these solvents, water or dioxane are preferred.

The reagent to be used is suitably water. If water is used as the solvent, then there is no necessity to add extra water. Additionally, a base may be added for the purpose of accelerating the reaction. Examples of such a base include: inorganic bases such as alkali metal carbonates (e.g., sodium carbonate, potassium carbonate and lithium carbonate), alkali metal hydrogencarbonates (e.g., sodium hydrogencarbonate, potassium hydrogencarbonate and lithium hydrogencarbonate), alkali metal hydrides (e.g., lithium hydride, sodium hydride and potassium hydride), alkali metal hydroxides (e.g., sodium hydroxide, potassium hydroxide, barium hydroxide and lithium hydroxide), alkali metal fluorides (e.g., sodium fluoride and potassium fluoride); and organic bases such as alkali metal alkoxides (e.g., sodium methoxide, sodium ethoxide, potassium methoxide, potassium ethoxide, potassium t-butoxide and lithium methoxide), N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). Of these bases, organic bases are preferred and pyridine is most preferred. In this regard, it is to be noted that where the hydrolysis reaction proceeds satisfactorily in the absence of a base, there is no necessity to add a base.

The reaction temperature varies depending on the starting compound and the reagent, but is usually in the range of from 0 to 100° C. and preferably in the range of from 20 to 60° C.

The reaction time varies depending on the reaction temperature, the starting compound, the reagent and the kind of solvent used, but is usually in the range of from 10 minutes to 3 days and preferably in the range of from 6 hours to 24 hours.

After completion of the reaction, the desired compound of the hydrolysis reaction can be isolated from the reaction mixture by a conventional method known to the person skilled in the art. For example, the resultant reaction mixture can be condensed using an ultrafiltration membrane and then freeze-dried to obtain the target compound of the reaction.

Alternatively, the desired compound can be used as a solution without isolation thereof where it is to be used for modification of proteins.

The desired compound thus obtained, if necessary, can be further purified by a conventional technique such as, for example, gel filtration chromatography. To obtain a compound having a particular desired average degree of polymerization or desired molecular weight, the purified compound may be further fractionated using gel filtration chromatography.

In the present invention, "ammonolysis" means a ring opening reaction of a carboxylic anhydride moiety of formula (III) with ammonia to give a moiety of formula (II) wherein $R^3$ is an amino group. The nature of the actual ammonolysis reaction is not particularly limited as long as it is a method commonly employed by those skilled in the art.

Examples of a suitable solvent to be used include: water; ethers such as diethyl ether, diisopropyl ether, tetrahydrofuran, dioxane, dimethoxyethane, and diethylene glycol dimethyl ether; and amides such as formamide, N,N-dimethylformamide, N,N-dimethylacetamide, N-methyl-2-pyrrolidone, N-methylpyrrolidinone and hexamethylphosphorotriamide. Of these solvents, water or dioxane are preferred. It is to be noted that the reagent to be used may also be used as the solvent.

Examples of suitable reagents to be used include ammonia gas and ammonia water, and ammonia is preferred.

The reaction temperature varies depending on the starting material and the reagent, but is usually in the range of from 0 to 100° C. and preferably in the range of from 10 to 40° C.

The reaction time varies depending on the reaction temperature, the starting compound, the reagent and the kind of solvent used, but is usually in the range of from 10 minutes to 3 days and preferably in the range of from 6 hours to 24 hours.

After completion of the reaction, the desired compound of the ammonolysis reaction can be isolated from the reaction mixture by a conventional method known to the person skilled in the art. The resultant reaction mixture can be, for example, worked up as follows to isolate the target compound: (1) dialysis through a semi-permeable membrane by the use of an acid such as an aqueous acetic acid solution to remove excess ammonia (the dialysis is carried out under such conditions that the reaction mixture solution does not become acidic, adding water as necessary), followed by condensation using an ultrafiltration membrane and then freeze-drying of the condensate thus obtained; or (2) addition of an aqueous sodium hydroxide solution and an immiscible organic solvent such as diethyl ether, shaking the resulting mixture (shaking may be carried out two or more times, as necessary) and then the separated aqueous layer containing the target compound is freeze-dried to obtain the target compound. Alternatively, the desired compound can be used as a solution without isolation thereof where it is to be used for modification of proteins.

The desired compound thus obtained, if necessary, can be further purified by a conventional technique such as, for example, gel filtration chromatography. To obtain a compound having a particular desired average degree of polymerization or desired molecular weight, the purified compound may be further fractionated using gel filtration chromatography.

It should be noted that the target compound of the ammonolysis reaction can contain structural units of formula (II) wherein $R^3$ is a hydroxy group as a result of the hydrolysis of some units of formula (III) in the starting material by water present in the solvent or the reagent. It should also be noted that a base may be added to the target compound for improved storage.

In the present invention, "aminolysis" means a ring opening reaction of a carboxylic anhydride moiety of formula (III) with an amine to give a moiety of formula (II) wherein $R^3$ is a group of formula —$NR^4R^5$, wherein $R^4$ and $R^5$ are as defined above. The nature of the actual aminolysis reaction is not particularly limited as long as it is a method commonly employed by those skilled in the art.

Examples of a suitable solvent to be used include: water; ethers such as diethyl ether, diisopropyl ether, tetrahydrofuran, dioxane, dimethoxyethane, and diethylene glycol dimethyl ether; and amides such as formamide, N,N-dimethylformamide, N,N-dimethylacetamide, N-methyl-2-pyrrolidone, N-methylpyrrolidinone and hexamethylphosphorotriamide. Of these solvents, water or dioxane are preferred. It is to be noted that the reagent to be used may also be used as the solvent.

The reagent to be used obviously depends upon the nature of the target group of formula —$NR^4R^5$. Amines typically used include methylamine, dimethylamine, ethylamine, diethylamine, 2-hydroxyethylamine, di-2-hydroxyethylamine, n-propylamine, di-n-propylamine, isopropylamine, diisopropylamine, 1-amino-2-propanol and 2-hydroxyisopropylamine, and aqueous solutions thereof. Of these reagents, preferred reagents include an aqueous dimethylamine solution and 1-amino-2-propanol; an aqueous dimethylamine solution is most preferred.

The reaction temperature varies depending on the starting compound and the reagent but is usually in the range of from 0 to 100° C. and preferably in the range of from 10 to 40° C.

The reaction time varies depending on the reaction temperature, the starting compound, the reagent, and the kind of solvent used, but is usually in the range of from 10 minutes to 3 days and preferably in the range of from 6 hours to 36 hours.

After completion of the reaction, the desired compound of the aminolysis reaction can be isolated from the reaction mixture by a conventional method known to the person skilled in the art. The resultant reaction mixture can be, for example, worked up as follows to isolate the target compound: (1) dialysis through a semi-permeable membrane by the use of an acid such as an aqueous acetic acid solution to remove excess ammonia (the dialysis is carried out under such conditions that the reaction mixture solution does not become acidic, adding water as necessary), followed by condensation using an ultrafiltration membrane and then freeze-drying of the condensate thus obtained; or (2) addition of an aqueous sodium hydroxide solution and an immiscible organic solvent such as diethyl ether, shaking the resulting mixture (shaking may be carried out two or more times, as necessary) and then the separated aqueous layer containing the target compound is freeze-dried to obtain the target compound. Alternatively, the desired compound can be used as a solution without isolation thereof where it is to be used for modification of proteins.

The desired compound thus obtained, if necessary, can be further purified by a conventional technique such as, for example, a gel filtration column. To obtain a compound having a particular desired average degree of polymerization or desired molecular weight, the purified compound may be further fractionated using gel filtration chromatography.

It should be noted that the target compound of the aminolysis reaction can contain structural units of formula (II) wherein $R^3$ is a hydroxy group as a result of the hydrolysis of some units of formula (III) in the starting material by water present in the solvent or the reagent. It should also be noted that a base may be added to the target compound for improved storage.

In the present invention, "alcoholysis" means a ring opening reaction of a carboxylic anhydride moiety of formula (III) with an alcohol or an aryl alcohol to give a moiety of formula (II) wherein $R^3$ is an alkoxy or aryloxy group as defined above. The nature of the actual alcoholysis reaction is not particularly limited as long as it is a method commonly employed by those skilled in the art.

Examples of the solvent to be used in the alcoholysis reaction include water; and amides such as formamide, N,N-dimethylformamide, N,N-dimethylacetamide, N-methyl-2-pyrrolidone, N-methylpyrrolidinone and hexamethylphosphorotriamide. Of these solvents, water is preferred. It is to be noted that the reagent to be used may also be used as the solvent.

The reagent to be used obviously depends upon the nature of the target alkoxy or aryloxy group. Typical examples of the alcohol used to obtain the desired alkoxy group include methanol, ethanol, ethylene glycol, n-propanol, propylene glycol, 2-hydroxy-n-propanol and iso-propanol, and aqueous solutions thereof while typical examples of the alcohol used to obtain the desired aryloxy group include phenol and p-nitrophenol. Of these reagents, ethanol is preferred.

The reaction temperature varies depending on the starting compound and the reagent but is usually in the range of from 0 to 100° C. and preferably in the range of from 10 to 40° C.

The reaction time varies depending on the reaction temperature, the starting compound, the reagent and the kind of solvent used but is usually in the range of from 10 minutes to 3 days and preferably in the range of from 6 hours to 36 hours.

After completion of the reaction, the desired compound of the alcoholysis reaction can be isolated from the reaction mixture by a conventional method known to the person skilled in the art. For example, the reaction mixture can be condensed using an ultrafiltration membrane, water added and then the mixture further condensed two or more additional times using an ultrafiltration membrane to remove excess alcohol, and then the obtained condensate is freeze-dried to obtain the target compound. Alternatively, the desired compound can be used as a solution without isolation thereof where it is to be used for modification of proteins.

The desired compound thus obtained, if necessary, can be further purified by a conventional technique such as, for example, a gel filtration column. To obtain a compound having a particular desired average degree of polymerization or desired molecular weight, the purified compound may be further fractionated using gel filtration chromatography.

It should be noted that the target compound of the alcoholysis reaction can contain structural units of formula (II) wherein $R^3$ is a hydroxy group as a result of the hydrolysis of some units of formula (III) in the starting material by water present in the solvent or the reagent. It should also be noted that a base may be added to the target compound for improved storage.

Where the desired copolymer of the present invention is a pharmacologically acceptable salt, the method for preparing said salt is not particularly limited as long as it is a method commonly employed in the field. For example, a pharmacologically acceptable salt can be obtained by dissolving a copolymer of the invention in an organic solvent, adding a base to the solution thus obtained and then collecting the resultant salt that is precipitated.

A variety of tactics can be employed to control the average molecular weight, the extent of the alternating arrangement and the composition ratio of the copolymers of the present invention.

It is well known that maleic anhydride monomers tend to polymerize alternately with co-monomers including polyoxyethylene allyl methyl diether [e.g. see Comprehensive Polymer Scence Vol. 4, Chain polymerization Part II, Ed. by G. C. Eastmond et al., pp. 377-422, Pergamon Press (1989); T. Yoshimoto et al., Biochemical Biophysical Research Communication Vol. 148, 876-882 (1987)]. The average molecular weight and arrangement of polymers can be controlled by those skilled in the art (e.g. see T. Ohtsu and M. Kinoshita, Koubunshi Gousei no Jikkenhou pp. 125-154, Kagaku-Dojin 1972). In addition, although maleic anhydride tends to polymerize alternately with co-monomers, the possibility of greater than 50 mol % of the composition ratio being comprised of maleic anhydride units in the co-polymer is well known to those skilled in the art (Japanese Patent No. 2621308, No. 2701295, No. 2803265, No. 3271265, No. 3035675 and No. 3106265, and Japanese Patent Application Publication No. 2003-105003 and No. 2003-105040).

Generally, to obtain polymers with a higher molecular weight and a greater degree of alternating arrangement, the polymerization should be carried out under mild conditions, such as lower temperature and lower initiator concentration. Higher monomer concentration and lower solvent concentration that reduce the relative concentration of initiator also result in a higher molecular weight and a higher degree of alternating arrangement.

Alternatively, to obtain polymers with a lower molecular weight and a lower degree of alternating arrangement, higher temperature, higher initiator concentration, lower monomer concentration and higher solvent concentration are favorable. Also, under such relatively severe polymerization conditions and/or with more than 50 mol % of the total monomers in the monomer mixture being maleic anhydride, the composition ratio of maleic anhydride units in the resulting co-polymer can be more than 50 mol %.

Some examples of polymerization conditions for polyoxyethylene allyl methyl diether and maleic anhydride are described in T. Yoshimoto et al., Biochemical Biophysical Research Communication Vol. 148, 876-882 (1987). According to this paper, polyoxyethylene allyl methyl diether, maleic anhydride, toluene and benzoyl peroxide (initiator) were mixed and polymerization was performed by refluxing at 80° C. for 7 hours. The resulting polymer had a molecular weight of 13 kD, and possessed 8 PEG chains and 8 maleic anhydride units. An alternating arrangement of the co-polymer was suggested from the fact that it has a composition ratio of 1:1 and that maleic anhydride monomers tends to copolymerize alternately with the co-monomers. If a copolymer having a lower molecular weight and lower extent of alternating arrangement are needed, then a higher initiator concentration, lower monomer concentration and/or higher solvent concentration should be applied. For example, when toluene is used as the solvent in polymerisation and the polymerisation is performed at 1 atmosphere, the polymerisation can be performed up to its boiling point of 110° C. Also, a higher temperature with a different solvent whose boiling temperature is higher than toluene is preferred. In such instances, the kind of initiator needs to be suitably selected because each initiator has a different specific decomposition rate constant and some initiators would decompose at these higher temeperatures. Numerous initiators with different decomposition rates are already known in the art [e.g. see Polymer Handbook, Third Edition, pp. II/1-11/65, Ed. by J. Brandrup and E. Immergut, John Wiley & Sons (1989)].

Alternative solvents, inititators and reaction conditions to vary the composition ratio, molecular weight and degree of alternating arrangement in copolymerisation reactions of polyoxyethylene allyl methyl diether and maleic anhydride are also disclosed in other prior art documents such as Japanese Patent Application Publication No. 2003-105003. Xylene, for example has a higher boiling point at 1 atmosphere (140° C.) than toluene. It is also known that the copolymerisation reactions can be performed without any solvent in some instances which removes the solvent boiling point limitation on the polymerisation temperature. Various alternative initiators such as benzoyl peroxide, di-tert-butylperoxide and tert-butylperoxyisobutyrate and azo initiators such as azobisisobutyronitrile are also disclosed. It is also possible to decrease the average molecular weight of the copolymer by the use of chain transfer reagents.

If a composition ratio of maleic anhydride units to the total monomer units in the co-polymer of greater than 50% is required, an increased percentage of maleic anhydride monomers in the monomer mixture with or without such relatively severe polymerization conditions should be applied.

Where a pharmaceutically active ingredient is being prepared using a copolymer of the present invention or a pharmacologically acceptable salt thereof and a protein or an analogue or variant thereof, the ratio of the copolymer to the protein or an analogue or variant thereof is not specifically limited as long as the resulting complex has the desired pharmaceutical activity. Typically, the weight ratio of the copolymer of the present invention or a pharmacologically acceptable salt thereof to the protein or an analogue or variant thereof is from 0.01 to 100:1; preferably it is from 0.1 to 50:1; yet more preferably it is from 1 to 10:1; and most preferably it is from 1 to 1.5:1.

In practical use, a pharmaceutically active ingredient comprising the copolymer of the present invention or a pharmacologically acceptable salt thereof and a protein or an analogue or variant thereof is typically prepared in the form of a protein solution containing the copolymer or a freeze-dried one containing the copolymer of the present invention or a pharmacologically acceptable salt thereof and the protein or an analogue or variant thereof. In the latter case, the freeze-dried form of the active ingredient is dissolved just before it is to be used. Alternatively, the pharmaceutically active ingredient may be prepared in the form of a kit. In this case, the copolymer of the present invention or a pharmacologically acceptable salt thereof and a protein or an analogue or variant thereof are stored in different containers and then mixed to prepare the desired pharmaceutically active ingredient just before use. Of these different forms, the freeze-dried form is most preferred.

Where the copolymer of the present invention or a pharmacologically acceptable salt thereof is used as a protein modifier, the ratio of the copolymer or pharmacologically acceptable salt thereof with respect to the protein or an analogue or variant thereof is not particularly limited to any specific value as long as the desired protein modification is achieved. Typically, the weight ratio of the copolymer of the present invention or a pharmacologically acceptable salt thereof to the protein or an analogue or variant thereof is 0.01 to 100:1; preferably it is from 0.1 to 50:1; yet more preferably it is from 1 to 10:1; and most preferably it is from 1 to 1.5:1.

Where the copolymer of the present invention is used as a protein modifier, the method for modifying the protein is not particularly limited as long as it is a method commonly employed for modifying a protein. For example, a protein or an analogue or variant thereof may be modified as follows.

The solvent to be used in the modification process is an aqueous solution containing an electrolyte which is commonly used for dissolving a protein and the pH thereof is not limited to any specific value as long as it lies in a range where the protein modifier can be negatively charged as a result of the dissociation of at least some of the carboxyl groups in the protein modifier of the present invention and the protein or an analogue or variant thereof can be positively charged. For example, the pH can be set to a value in the range of from 3 to the isoelectric point of the protein or an analogue or variant thereof, and preferably it is set to a value in the range of from 4 to 8. In this regard, it should be noted that the isoelectric point of the protein or an analogue or variant thereof can be determined by electrophoresis.

The protein modifier is dissolved in the above-described solvent and then the thus obtained solution is added to an aqueous solution of said protein or an analogue or variant thereof. The obtained solution may be shaken to facilitate reaction if necessary. The pH of the resulting mixture may be adjusted if desired by the addition of an acid and/or a base. The ratio of the protein modifier of the present invention to be used with respect to said protein or an analogue or variant thereof is not limited to any specific value as long as it gives the desired modification to the protein. Typically, the ratio is in the range of from 0.01 to 100 by weight; preferably in the range of from 0.1 to 50; more preferably in the range of from 1 to 10; and most preferably it is from 1 to 1.5:1.

The reaction temperature for the modification process varies depending on the compound used and the reagent but is usually in the range of from 0 to 100° C., preferably in the range of from 4 to 40° C. and most preferably in the range of from 30 to 40° C.

The reaction time varies depending on the reaction temperature, the compound used, the reagent and the kind of solvent used, but is usually in the range of from 5 minutes to 14 days, preferably in the range of from 1 hour to 12 days, and more preferably in the range of from 5 days to 10 days.

Sometimes, during the protein modification process the conditions used are such that some of the structural units of formula (II) in the copolymer are converted to units of formula (II) having a different identity. For example, where $R^3$ in the structural units of formula (II) is a group other than a hydroxy group, the conditions used for the modification process are such that some of said $R^3$ groups are hydrolysed to give structural units of formula (II) wherein $R^3$ is a hydroxy group.

As noted above, the complexes of the present invention comprise at least one protein or an analogue or variant thereof which is bound to at least one copolymer of the present invention or a pharmacologically acceptable salt thereof. In said complex, the protein or an analogue or variant thereof and copolymer or a pharmacologically acceptable salt thereof are bound to each other by a chemical bond such as a covalent bond (e.g. Schiff base formation, amide bond formation and ester bond formation), an ionic bond or a coordinate bond, or by a non-chemical bond such as a hydrophobic interaction, a hydrogen bond, an electrostatic interaction or affinity binding.

Preferably, the complexes of the present invention are not detected in dissociated form to any significant extent when subjected to size exclusion chromatography or SDS-PAGE under non-reducing conditions. More preferably, the complexes of the present invention are not detected in dissociated form to any significant extent when subjected to size exclusion chromatography and SDS-PAGE under non-reducing conditions. Yet more preferably, additionally the rate of failure to detect the protein of the complex by ELISA of the complexes of the present invention as a result of modification of the protein structure by the copolymers and pharmacologically acceptable salts thereof is very low (preferably, the rate of failure is 20% or less, more preferably 15% or less and most preferably 10% or less).

In the present invention, a protein analogue is defined as a protein encoded by cDNA cloned from a cDNA library derived from animal cells, body fluids or tissues by hybridization using cDNA of the protein under stringent conditions (60 to 70° C., 6×SSC).

In the present invention, a protein variant is defined as a protein which is obtained by substituting, deleting, adding or inserting one or more amino acids in the original protein and still has at least a part of the activity of the original protein at a detectable level.

Preferably, the protein or an analogue or variant thereof is a basic protein. More preferably, the basic protein is a basic fibroblast growth factor (bFGF), an epidermal growth factor (EGF), an osteoclastogenesis inhibitory factor (OCIF), a platelet-derived growth factor (PDGF), a brain-derived neurotrophic factor (BDNF), a nerve growth factor (NGF), a human growth hormone (HGH), a hepatocyte growth factor (HGF), or a vascular endothelial growth factor (VEGF), or an analogue or a variant thereof. Most preferably, the basic protein is an osteoclastogenesis inhibitory factor (OCIF) or an analogue or a variant thereof OCIF, an analogue thereof or a variant thereof used in the present invention can be natural type or it can be recombinant type and its origin is not particularly limited. Natural type OCIF means OCIF that is obtained as a naturally produced protein by extraction, purification and/or isolation from an organ, a body fluid, a cell culture, or a culture medium derived from a human or a non-human animal. Recombinant type OCIF, an analogue thereof or a variant thereof is a recombinant protein obtained by extraction, purification and/or isolation of said protein from a host conventionally used in such techniques such as a prokaryotic host cell (e.g. *Escherichia coli*) or a eukaryotic cell such as a human or a non-human cell line which has been transformed with a vector comprising a polynucleotide which encodes an OCIF, an analogue thereof or a variant thereof [e.g. see the recombinant methods disclosed in EP-A-0816380 (WO-A-96/26217) and WO-A-97/23614].

The origin of the OCIF, analogues thereof and variants thereof used in the present invention is not particularly limited and they can be derived from a human or a non-human animal. Preferably, they can be derived from a mammal such as a human, rat, mouse, rabbit, dog, cat, cow, swine, sheep or goat; or an avian such as a fowl, goose, chicken or turkey. More preferably, they are derived from mammals and most preferably they are derived from a human.

The OCIF or analogue thereof used in the present invention can be a monomer-type OCIF (e.g. in humans a monomer having a molecular weight as measured by SDS-PAGE under non-reducing conditions of about 60000) or a dimer type (e.g. in humans a dimer having a molecular weight of about 120000 as measured by SDS-PAGE under non-reducing conditions) [see EP-A-0816380 (WO-A-96/26217)]. It is preferably a monomer of human OCIF having a molecular weight of about 60,000 as measured by SDS-PAGE under non-reducing conditions or a dimer of human OCIF having a molecular weight of about 120,000 as measured by SDS-PAGE under non-reducing conditions, and is more preferably a dimer of human OCIF having a molecular weight of about 120,000 as measured by SDS-PAGE under non-reducing conditions.

It is known that OCIF is translated in cells as a polypeptide containing a signal peptide at the amino terminus thereof and that it is then matured by processing involving the removal of said signal peptide [e.g. see the recombinant methods disclosed in EP-A-0816380 (WO-A-96/26217) and WO-A-97/23614]. The OCIF, analogue thereof or variant thereof used in the present invention includes both the polypeptide containing a signal peptide and the matured form thereof. Preferred examples include the human OCIF with the signal peptide having amino acids −21 to +380 of SEQ. ID. NO.1 of the sequence listing and the mature human OCIF without the signal peptide having amino acids +1 to +380 of SEQ. ID. NO.1 of the sequence listing. Of these, the mature human OCIF is particularly preferred.

It is also known that methionine can be added to such a matured form of OCIF, an analogue thereof or a variant thereof, when it is expressed as a recombinant protein in a host cell, especially in a prokaryotic host cell such as *Escherichia coli*. This is achieved by adding a nucleotide triplet having the sequence ATG (AUG) to the 5'-end of a polynucleotide encoding a matured form of OCIF, an analogue thereof or a variant thereof, and inserting the resultant polynucleotide into a suitable expression vector. The desired matured protein having methionine at the amino terminus thereof can be then expressed by a suitable host cell which has been transformed by said recombinant expression vector. Additionally, one or more than one amino acid can be added to said protein at a position next to the amino terminal methionine by the addition of further nucleotide triplets next to the ATG triplet added at the 5'-end of the polynucleotide encoding a matured form of OCIF, an analogue thereof or a variant thereof. The target matured form of OCIF, an analogue thereof, or a variant thereof having methionine at the amino terminus can be purified and isolated from a culture of the transformed host cell according to a conventional method. In addition, one or more amino acids may be inserted into the matured form of OCIF having methionine at the amino terminus, an analogue thereof or a variant thereof at a position adjacent to the methionine and closer to the carboxy terminus than the methionine.

In the present invention, an OCIF analogue means a protein encoded by a polynucleotide which exists naturally in the cells, body fluid, and/or organs of a human or non-human animal such as those exemplified above. Specific preferred examples of such analogues include OCIF2, OCIF3, OCIF4 and OCIF5 [see EP-A-0816380 (WO96/26217)]. Such OCIF analogues or active fragments thereof can be obtained by a method such as the following: RNA is extracted from a cell, organ, tissue or body fluid of a human or non-human animal; a first strand of cDNA which is complementary to said RNA is synthesized using a reverse transcriptase, and then a second strand of said cDNA is synthesized using the first as a template using a DNA polymerase; the double-stranded cDNA thus-obtained is inserted into a suitable, conventionally-used expression vector; a suitable, conventionally-used host cell is then transformed by the vector thus-obtained; the host producing the desired peptide is then screened for using a hybridization technique such as plaque hybridization or phage hybridization using OCIF cDNA or a fragment thereof as a probe under stringent conditions [see EP-A-0816380 (WO-A-96/26217)]; and then finally the desired OCIF analogue is expressed by a conventional technique by the thus-obtained host cell.

In the present invention, an OCIF variant means a protein which has an amino acid sequence wherein one or more than one amino acid residues have been substituted in, deleted from, added to or inserted in the amino acid sequence of an OCIF or an analogue thereof, and still has at least some OCIF activity. Such OCIF variants can be obtained by, for example, the following method: substituting, deleting, adding and/or inserting one nucleotide or more than one nucleotides in a nucleotide sequence encoding OCIF or an analogue thereof using a polymerase chain reaction method (referred to hereinafter as PCR), a genetic recombination method or a nuclease digestion method using an exonuclease or endonuclease such as a restriction enzyme; transforming a eukaryotic host cell such as an animal cell or a prokaryotic host cell such as Escherichia coli with an expression vector wherein the obtained nucleotide encoding the desired OCIF variant has been inserted; and then extracting, purifying and/or isolating the desired pepetide from the protein-containing fraction produced by a cell culture of said transformed host according to a method well-known to the person skilled in the art.

Truncated forms of OCIF wherein a considerable part of the amino acid sequence has been deleted from the carboxy terminus of an OCIF polypepetide are also known to keep at least some OCIF activity [e.g. see EP-A-0816380 (WO-A-96/26217) and WO-A-97/23614]. Such truncated types of OCIF retaining at least some of the activity of the complete OCIF polypeptide are also included in the OCIF variants of the present invention.

Furthermore, OCIF or a truncated form thereof that is fused with the an immunoglobulin domain such as the Fc domain (e.g. a fusion polypeptide in which the Fc domain of human IgG is attached to the carboxy terminus of OCIF) and which retains at least some of the activity of the complete OCIF polypeptide is known (see WO-A-97/23614), and such fusion proteins are also included in the OCIF variants of the present invention.

Any naturally-produced OCIF or an analogue thereof or recombinant OCIF or analogue or variant thereof can contain a sugar chain which is attached to the OCIF or analogue or variant thereof post-translationally. Naturally-produced OCIF or an analogue thereof containing a sugar chain can be obtained from cell cultures, tissues, organs, body fluids or cell lines derived from human or non-human animals using conventional techniques. Recombinant OCIF or an analogue or variant thereof containing a sugar chain can be obtained from a culture of a eukaryotic host cell transformed using a vector comprising a nucleotide sequence encoding any OCIF or an analogue or variant thereof such as those described and exemplified above. Examples of suitable host cells that can be used which are capable of the post-translational modification of OCIF or an analogue or variant thereof so as to attach a sugar chain include chinese hamster ovary cells and COS cells [Yasuda, H. et al, Endocrinology, 139, 1329-1337 (1998)]. OCIF or an analogue or variant thereof containing such a sugar chain is suitable for use in the formation of the complexes of the present invention. The sugar chain in OCIF or an analogue or variant thereof containing a sugar chain can be artificially modified (in particular, enzymatically) with polymers, polysaccharides or modified polysaccharides.

The pharmaceutical composition of the present invention which contains a copolymer of the present invention or a pharmacologically acceptable salt thereof and a protein or an analogue thereof may be a solution prepared according to a method described above or one obtained by freeze-drying the solution. Alternatively, such a pharmaceutical composition may be formulated according to an alternative method or it may in the form of a kit. In the latter case, the copolymer of the present invention or a pharmacologically acceptable salt thereof and a protein or an analogue or variant thereof are stored in different containers and then mixed to prepare the desired pharmaceutical composition just before use.

The pharmaceutical compositions of the present invention may optionally further comprise a base. The base is not limited to any specific base as long as it is a base commonly used in pharmaceutical compositions. Examples of such a base include: inorganic bases such as alkali metal carbonates (e.g. sodium carbonate, potassium carbonate and lithium carbonate), alkali metal hydrogencarbonates (e.g. sodium hydrogencarbonate, potassium hydrogencarbonate and lithium hydrogencarbonate), alkali metal hydrides (e.g. lithium hydride, sodium hydride, and potassium hydride), alkali metal hydroxides (e.g. sodium hydroxide, potassium hydroxide, barium hydroxide and lithium hydroxide), alkali metal fluorides (e.g. sodium fluoride and potassium fluoride); and organic bases such as alkali metal alkoxides (e.g. sodium methoxide, sodium ethoxide, potassium methoxide, potassium ethoxide, potassium t-butoxide and lithium methoxide), alkali metal mercaptans (e.g. sodium methyl mercaptan and sodium ethyl mercaptan), N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU). Of these bases, alkali metal hydroxides are preferred and sodium hydroxide is particularly preferred. In this regard, it is to be noted that a part or all of the bases may form salts with the copolymer of the present invention.

Examples of the pharmaceutical composition according to the present invention comprise a complex of at least one substance selected from a copolymer of the present invention or a pharmacologically acceptable salt thereof and a protein or an analogue or variant thereof selected from bFGF (used for the treatment or prevention of ischemic arteriopathic disease and intractable skin ulcers), EGF (used for the treatment or prevention of ulcerous diseases such as ulcerative colitis and prolonged corneal epithelial disorder), PDGF (used for the treatment of wounds), BDNF and NGF (used for the treatment or prevention of diseases of the central nervous system such as Parkinson's Disease and Alzheimer's Disease), HGH (used for the treatment or prevention of growth hormone deficiency, growth hormone hyposecretion syndrome, Turner's syndrome and cartilage dystrophy), HGF (used for the treatment or prevention of diabetes mellitus, arteriosclerosis such as brain infarction and hepatitis fibrosis) and VEGF (ischemic arteriopathic disease and peripheral arterial occlusive disease).

One particularly preferred example of the pharmaceutical composition according to the present invention comprises a complex of at least one substance selected from OCIF, an analogue and a variant thereof and at least one substance selected from a copolymer of the present invention or a pharmacologically acceptable salt thereof. Such a pharmaceutical composition is particularly suitable for the prevention or treatment of bone metabolic diseases. In the present invention, such bone metabolic diseases include any diseases which are characterized by substantial bone mass reduction in the patient suffering therefrom and in which it is necessary to suppress bone resorption or the rate of bone resorption in order to prevent or treat said diseases.

Bone metabolic diseases which can be treated or prevented using the pharmaceutical composition of the present invention include: primary osteoporosis (senile osteoporosis, postmenopausal osteoporosis, and idiopathic juvenile osteoporosis); endocrine osteoporosis (hyperthyroidism, hyperparathyroidism, Cushing's syndrome, and acromegaly); osteoporosis accompanying hypogonadism (hypopituitarism, Klinefelter syndrome, and Turner syndrome); hereditary and congenital osteoporosis (osteogenesis imperfecta, homocystinuria, Menkes syndrome, and Riley-Day syndrome); osteopenia due to gravity load mitigation or fixation and immobilization of limbs; Paget's disease; osteomyelitis; infectious focus due to loss of bone; hypercalcemia resulting from solid carcinoma (breast carcinoma, lung cancer, kidney cancer, and prostatic cancer); hematological malignant diseases (multiple myeloma, lymphoma, and leukemia); idiopathic hypercalcemia; hypercalcemia accompanying hyperthyroidism or kidney malfunction; osteopenia resulting from steroid medication; osteopenia resulting from administration of other medicines (e.g., immunosuppressive agents such as methotrexate and cyclosporine A, heparin, and antiepileptics); osteopenia accompanying kidney malfunction; osteopenia accompanying a surgical operation or digestive organ diseases (e.g., small intestine hindrance, large intestine hindrance, chronic hepatitis, gastrectomy, primary biliary liver cirrhosis, and liver cirrhosis); osteopenia due to various types of rheumatism such as rheumatoid arthritis; osteoclasis and joint destruction due to various types of rheumatism such as rheumatoid arthritis; mutilans type rheumatoid arthritis; osteoarthritis; loss of periodontal bone; cancer metastasis to bone (osteolysis metastasis); osteonecrosis or osteocyte death accompanying traumatic iunjury, Gaucher's disease, sickle-cell anemia, systemic lupus erythematosus, or nontraumatic injury; osteodystrophy such as renal osteodystrophy; osteopenia accompanying hypophosphatasia or diabetes; osteopenia accompanying nutritional disorder or eating disorder; and other osteopenia. Further, in the present invention, cachexia due to the above-mentioned solid carcinoma, cancer metastasis to bone (osteolysis metastasis) or hematological malignant diseases is also included in bone metabolic diseases (see Japanese Patent Application (Kokai) No. 2000-178200).

The pharmaceutical composition according to the present invention as described above can be safely administered orally or non-orally to a human or animals other than a human. The dosage form of the pharmaceutical composition may be appropriately selected depending on the kind of disease, the level of the disease and the condition, age, sex and weight of the patient. For example, the pharmaceutical composition may be orally administered in the form of tablets, capsules, powders, granules or syrups; injected in the form of an injection intravenously alone or in combination with a common adjunct such as glucose, amino acids or the like, or injected intramuscularly, subcutaneously, intracutaneously or intraperitoneally alone; administered transdermally in the form of cataplasm; administered transnasally in the form of nasal drops; administered transmucosally or to the oral cavity in the form of a transmucosal preparation; or administered intrarectally in the form of a suppository. These preparations can be formulated in a conventional manner using well-known auxiliary agents which are generally used in the field of medicine such as excipients, binding agents, disintegrants, lubricants, flavoring agents, solubilizers, suspending agents, colorants, pH regulators, antiseptics, gelling agents, surfactants and coating agents.

Where the pharmaceutical composition is prepared in the form of a tablet, various carriers known in the art can be used. Examples of such carriers include: excipients such as lactose, sucrose, sodium chloride, glucose, urea, starch, calcium carbonate, kaolin, crystalline cellulose and silicic acid; binding agents such as water, ethanol, propanol, simple syrup, glucose solution, starch solution, gelatin solution, carboxymethyl cellulose, shellac, methyl cellulose, potassium phosphate and polyvinyl pyrrolidone; disintegrants such as dry starch, sodium alginate, agar powder, laminaran powder, sodium hydrogencarbonate, calcium carbonate, polyoxyethylene sorbitan fatty acid esters, sodium lauryl sulfate, stearic acid monoglyceride, starch and lactose; disintegration inhibitors such as sucrose, stearin, cacao butter and hydrogenated oil; absorption accelerators such as quaternary ammonium bases and sodium lauryl sulfate; moisturizers such as glycerin and starch; absorbents such as starch, lactose, kaolin, bentonite and colloidal silicic acid; and lubricants such as purified talc, stearates, boric acid powder and polyethylene glycol. In addition, such a tablet may be covered with a conventional coating, if necessary. Examples of such a coated tablet include a sugar-coated tablet, a gelatin-coated tablet, an enteric coated tablet, a film-coated tablet, a double-layered tablet and a multi-layered tablet.

Where the pharmaceutical composition is prepared in the form of a pill, various carriers known in the art can be used. Examples of such carriers include: excipients such as glucose, lactose, cacao butter, starch, hydrogenated vegetable oil, kaolin and talc; binding agents such as gum Arabic powder, traganth powder, gelatin and ethanol; and disintegrants such as laminaran agar.

Where the pharmaceutical composition is prepared in the form of a suppository, various carriers known in the art can be used. Examples of such carriers include polyethylene glycol, cacao butter, higher alcohols, esters of higher alcohols, gelatin and semi-synthetic glycerides.

Where the pharmaceutical composition is prepared in the form of an injection, it is preferred that the composition in the form of a solution or a suspension is sterilized and is made isotonic with blood. When such a composition in the form of a solution, an emulsion, a suspension or a substantially homogenous aqueous solution is prepared, various diluents known in the art can be used. Examples of such diluents include water, ethanol, propylene glycol, ethoxylated isostearyl alcohol, polyoxylated isostearyl alcohol and polyoxyethylene sorbitan fatty acid esters. In this case, the pharmaceutical composition may further contain common salt, glucose or glycerin in an amount sufficient to maintain isotonicity with blood. Further, the pharmaceutical composition may also contain conventional solubilizers, buffering agents, smoothing agents, pH regulators, stabilizers or solubilizing agents. Such an injection may be freeze-dried.

Additionally, the pharmaceutical composition of the present invention may also contain colorants, preservatives, perfumes, flavoring agents, sweeteners or other medicine if required.

The amount of the complex of OCIF or an analogue or variant thereof and copolymer or a pharmacologically acceptable salt thereof contained in the pharmaceutical composition of the present invention is not limited to any specific value, but it is usually in the range of from 0.1 to 70 wt %, and preferably in the range of from 1 to 30 wt %.

In the present invention, the dose of the complex of OCIF or an analogue or variant thereof and copolymer or a pharmacologically acceptable salt thereof contained in the pharmaceutical composition of the present invention depends on various factors including the condition and age of the patient, the route of administration and the form of the drug. In general, the amount administered to an adult human per administration is in a range between the upper limit of 1 to 50 mg/kg and a lower limit of 0.001 to 0.1 mg/kg, wherein the range of from 0.01 to 1 mg/kg is preferable, and the range of from 0.1 to 1 mg/kg is more preferable.

The pharmaceutical composition according to the present invention should be administered once per several months, once per month, once per several days, once per day or several times per day depending on the kind of ingredient contained in the pharmaceutical composition, the route of administration and the form of the drug. When the composition comprises a complex of OCIF or an analogue or variant thereof and a copolymer or a pharmacologically acceptable salt thereof for use as an agent for the treatment or prevention of bone metabolic diseases according to the present invention it should be administered once per several months, once per month, once per several days, once per day or several times per day depending on the kind of active ingredient contained in the agent for the treatment or prevention of bone metabolic diseases, the route of administration and the form of the drug.

The copolymer of the present invention and pharmacologically acceptable salts thereof are useful as a polymeric modifier capable of providing a complex having uniform properties, especially reduced production of disorganised cross-linked structures with the protein, better maintenance of protein activity and excellent retention of the protein in the blood after administration of said complex. This makes it particularly useful as a modifier for modifying the pharmaceutical properties of proteins having useful pharmaceutical activity.

EXAMPLES

The following examples, reference examples and test examples are intended to further illustrate the present invention and are not intended to limit the scope of the invention in any way. In the following examples, m and $R^3$ are as defined above for formulae (I) and (II), "comp. ratio" is the composition ratio [i.e. the ratio of the structural units (I) and (II)], "av. deg. pol." is the average degree of polymerisation of the copolymer prepared and "hyd. ratio" is the hydrolysis ratio of the copolymer prepared [i.e. the average ratio of the structural units wherein $R^3$ is —OH to the structural units wherein $R^3$ is other than —OH].

Example 1

Preparation of poly($PEG_{500}$-MA) hydrolysate [poly($PEG_{500}$-MA)h)] wherein m=6-16, $R^3$=OH, comp. ratio=about 1:1, av. deg. pol.=30-40 and hyd. ratio=about 10:0 (Compound No. 1)

A copolymer of polyoxyethylene allyl methyl diether (m=6-16, Alk =ethylene, $R^1$=hydrogen and $R^2$=methyl) and maleic anhydride, in which the polyoxyethylene side chain has an average molecular weight of about 500 and the average degree of polymerization of the main chain is in the range of from 30 to 40, [AM-0530K, manufactured by NOF Corporation (hereinafter referred to as "poly($PEG_{500}$-MA)"] was used as the starting material. 50 ml of distilled water were added to 3 g of poly($PEG_{500}$-MA) to dissolve said starting material, and the solution thus obtained was stirred at 40° C. for 15 hours. The resulting solution was condensed using an ultrafiltration membrane made of polyethersulfone (having a molecular weight cut-off of 10,000, manufactured by Millipore Corporation, model number PBGC07610), and the resulting condensate was freeze-dried to obtain 1.3 g of the title compound poly($PEG_{500}$-MA)h (Compound No. 1) as an oily compound.

Poly($PEG_{500}$-MA)h (Compound No. 1) was purified using gel filtration as follows. 100 mg of poly($PEG_{500}$-MA)h (Compound No. 1) were dissolved in 4 ml of 0.001 N sodium hydroxide solution. The solution was divided into four batches and each 1 ml batch was applied to a gel filtration column (PD-10, manufactured by Amersham-Pharmacia). The first 1 ml of eluant was discarded. 1.5 ml of 0.001 N sodium hydroxide solution were then applied to each column and a further 1.5 ml were eluted from the column and discarded. 2.5 ml of 0.001 N sodium hydroxide solution were then applied to each column and a further 2.5 ml were eluted from the column and it is this fraction that contained the purified poly($PEG_{500}$-MA)h (Compound No. 1). The purified fractions from the four columns were combined to give 10 ml of a purified solution of the title compound. The yield after the purification step (determined spectophotometrically by measuring the absorbance of poly($PEG_{500}$-MA)h at 210 nm before and after purification) was determined to be 80% (80 mg of polymer) and the concentration in the purified solution was determined to be 8 mg/ml.

The carboxyl group content of the title compound was determined by conductometric titration as follows. 7.5 ml of the solution of the purified title compound obtained above (containing 60 mg of the title compound) were made up to a volume of 50 ml with distilled water and the solution thus obtained was adjusted to pH 12 with 1M aqueous sodium hydroxide solution. 0.1M hydrochloric acid was added to the solution in increments of 0.1 ml, the pH and conductivity of the solution being measured after each addition of hydrochloric acid. The carboxyl group content of the copolymer was then calculated from the amount of 0.1M hydrochloric acid added in the conductivity buffering region (i.e. the region of the plot of conductivity against amount of hydrochloric acid added in which the carboxyl groups of the copolymer of the title compound act as a buffer, said region corresponding to a pH range of about 10.5 to 3); the molar amount of hydrochloric acid used in the conductivity buffering region is equal to the molar amount of carboxyl groups on the copolymer of the title compound. As a result, the carboxyl group content per 1 g of title compound was determined to be 3.22 mmols. From this, the composition ratio was calculated to be 1:1.07. This figure was applied for the following Examples where the same starting material was used.

Example 2

Preparation of poly($PEG_{500}$-MA) hydrolysate [poly($PEG_{1500}$-MA)h)] wherein m=28-38, $R^3$=OH, comp. ratio=about 1:1, av. deg. pol.=10-15 and hyd. ratio=about 10:0 (Compound No. 2)

A copolymer of polyoxyethylene allyl methyl diether (m=28-38, Alk =ethylene, $R^1$=hydrogen and $R^2$=methyl) and maleic anhydride, in which the polyoxyethylene has an average molecular weight of about 1500 and the average degree of polymerization of the main chain is in the range from 10-15, (AM-1510K, manufactured by NOF Corporation) [hereinafter referred to as "poly($PEG_{1500}$-MA)"] was used as the starting material. 25 ml of distilled water were added to 1.5 g of poly($PEG_{1500}$-MA) to dissolve said starting material, and the solution thus obtained was stirred at room temperature for 20 hours. At the end of this time, the solution was condensed in the same manner as described in Example 1 above using an ultrafiltration membrane made of polyethersulfone (having a molecular weight cut-off of 10,000, manufactured by Millipore Corporation, model number PBGC07610), and the resulting condensate was freeze-dried to obtain 0.8 g of the title compound poly(PEG$_{1500}$-MA)h (Compound No. 2) as an oily compound.

The carboxyl group content of the title compound poly(PEG$_{1500}$-MA)h (Compound No. 2) was measured in the same manner as described in Example 1 above and, as a result, the carboxyl group content per 1 g of the title compound was determined to be 1.63 mmols. From this, the composition ratio was calculated to be 1:1.4. This figure was applied for the following Examples where the same starting material was used.

Example 3

Preparation of product of ammonolysis of poly(PEG$_{500}$-MA) [poly(PEG$_{500}$-MA)a)] wherein m=6-16, $R^3$=NH$_2$, comp. ratio=about 1:1, av. deg. pol.=30-40 and hyd. ratio=about 0:10 (Compound No. 3)

9.5 g of ammonia water (ammonia concentration: 28 wt %) were added to 1 g of poly(PEG$_{500}$-MA) (AM-0530K, manufactured by NOF Corporation) to dissolve said starting material, and the solution thus obtained was stirred at room temperature for 16 hours. At the end of this time, the solution thus obtained was subjected to dialysis through a regenerated cellulose membrane (having a molecular weight cut-off of 12,000 to 14,000, manufactured by Sanko Junyaku Co., Ltd., Model No. UC36-32-100) against 1 liter of a 0.1 wt % aqueous acetic acid solution for one day, and was then further subjected to dialysis against 1 liter of water for 1 day. After 1 liter of water was renewed, it was further subjected to dialysis for another one day. By carrying out such dialysis, excess ammonia was eliminated from the product. The solution thus obtained was condensed using an ultrafiltration membrane made of polyethersulfone (having a molecular weight cut-off of 10,000, and manufactured by Millipore Corporation, model number PBGC07610), and the resulting condensate was freeze-dried to obtain 0.99 g of the title compound poly(PEG$_{500}$-MA)a (Compound No. 3) as an oily compound.

The carboxyl group content in 1 g of poly(PEG$_{500}$-MA)a (Compound No. 3) was determined by conductometric titration in the same manner as described in Example 1 above and, as a result, the carboxyl group content per 1 g of the title compound was determined to be 1.55 mmols.

Under the reaction conditions used, it is possible that the maleic anhydride residue could be subjected not only to a ring-opening reaction due to ammonolysis but also hydrolysis by water present in the reaction system. The ratio of the maleic anhydride residues subjected to ammonolysis to the maleic anhydride residues subjected to hydrolysis was calculated as follows.

In Example 1, the carboxyl group content in 1 g of poly(PEG$_{500}$-MA)h (Compound No. 1) was determined. This gives the figure for carboxyl group content when all maleic acid residues are fully hydrolysed (3.22 mmols per 1 g of polymer). From this result, the weight of poly(PEG$_{500}$-MA)h (Compound No. 1) per mol of carboxyl group (1/3.22×10$^{-3}$ g) and the weight of poly(PEG$_{500}$-MA)h (Compound No. 1) per mol of ring-opened maleic acid residue [2× the weight of poly(PEG$_{500}$-MA)h (Compound No. 1) per mol of ring-opened maleic acid residue, since there are 2 carboxyl groups per fully hydrolysed maleic acid residue] were determined by calculation, giving the results 311 g and 621 g, respectively. From these values, the weight of poly(PEG$_{500}$-MA) (that is, the weight of the copolymer before hydrolysis) per gram of functional group, and the weight of poly(PEG$_{500}$-MA)a (Compound No. 3) obtained by adding ammonia to poly(PEG$_{500}$-MA) per gram of functional group were determined. Specifically, the weight of poly(PEG$_{500}$-MA) (that is, the weight of the copolymer before hydrolysis) per mol of maleic anhydride residue was obtained by subtracting the molecular weight of a molecule of water (18 g) from the weight of the fully hydrolysed copolymer, giving a figure of 603 g. The weight of poly(PEG$_{500}$-MA)a (Compound No. 3) per mol of carboxyl group was obtained by adding the molecular weight of a molecule of ammonia (17 g) to the weight of poly(PEG$_{500}$-MA), giving a figure of 620 g. From this value, the theoretical carboxyl group content per 1 g of poly(PEG$_{500}$-MA)a (Compound No. 3) where all maleic anhydride residues have been subjected to ammonolysis (i.e. no hydrolysis) was determined by calculation (1 g/620), and was found to be 1.61 mmols. From the carboxyl group content per 1 g of poly(PEG$_{500}$-MA)h (Compound No. 1), where all maleic anhydride residues were subjected to hydrolysis, the theoretical carboxyl group content per 1 g of poly(PEG$_{500}$-MA)a (Compound No. 3) where all maleic anhydride residues have been subjected to ammonolysis, and the actual carboxyl group content per 1 g of poly(PEG$_{500}$-MA)a (Compound No. 3) measured above (i.e. 1.55 mmols), the ratio of maleic anhydride residues subjected to ammonolysis in the title compound to the total number of maleic anhydride residues in the starting material was calculated, and was determined to be 1.0. Thus, it was confirmed that substantially all maleic anhydride residues had been subjected to ammonolysis and that virtually no hydrolysis had taken place.

Example 4

Preparation of reaction product of dimethylamine and poly(PEG$_{500}$-MA) [poly(PEG$_{500}$-MA)dma)] wherein m=6-16, $R^3$=NMe$_2$, comp. ratio=about 1:1, av. deg. pol.=30-40 and hyd. ratio=about 0:10 (Compound No. 4)

71 g of an aqueous dimethylamine solution (dimethylamine concentration: 50 wt %) were added to 10 g of poly(PEG$_{500}$-MA) (AM-0530K, manufactured by NOF Corporation) to dissolve it, and the solution thus obtained was stirred at room temperature for 20 hours. At the end of this time, the solution thus obtained was subjected to dialysis through a regenerated cellulose membrane (having a molecular weight cut-off of 12,000 to 14,000, and manufactured by Sanko Junyaku Co., Ltd., Model No. UC36-32-100) against 10 liter of a 0.1 wt % aqueous acetic acid solution for one day, and was then further subjected to dialysis against 10 liter of water for 1 day. After 10 liter of water was renewed, it was further subjected to dialysis for another one day. By carrying out such dialysis, excess dimethylamine was eliminated from the product. The solution thus obtained was condensed using an ultrafiltration membrane made of polyethersulfone (having a molecular weight cut-off of 10,000, and manufactured by Millipore Corporation, model number PBGC07610), and the resulting condensate was freeze-dried to obtain 6.3 g of the title compound poly(PEG$_{500}$-MA)dma (Compound No. 4) as an oily compound.

The carboxyl group content in 1 g of poly(PEG$_{500}$-MA)dma (Compound No. 4) was determined in the same manner as described in Example 1 above, and was determined to be 1.53 mmols. Using a calculation similar to that in Example 3 for the ammonolysis product, the theoretical carboxyl group content in 1 g of poly(PEG$_{500}$-MA)dma (Compound No. 4) where all maleic anhydride residues have been subjected to aminolysis was determined by calculation, and was determined to be 1.54 mmols. From these results, the ratio of maleic anhydride residues subjected to aminolysis in the title compound to the total number of maleic anhydride residues in the starting material was calculated, and was determined to be 1.0. Thus, it was confirmed that substantially all maleic anhydride residues had been subjected to aminolysis by dimethylamine and that virtually no hydrolysis had taken place.

Example 5

Preparation of reaction product of 1-amino-2-propanol and poly($PEG_{500}$-MA) [poly($PEG_{500}$-MA)ipa)] wherein m=6-16, $R^3$=NH(CH$_2$CH(OH)CH$_3$), comp. ratio=about 1:1, av. deg. pol.=30-40 and hyd. ratio=about 0:10 (Compound No. 5)

14 g of 1-amino-2-propanol were added to 1.5 g of poly($PEG_{500}$-MA) (AM-0530K, manufactured by NOF Corporation) to dissolve it, and the solution thus obtained was stirred at room temperature for 16 hours. At the end of this time, 300 ml of distilled water were added to the solution, and glacial acetic acid was further added to neutralize the solution. The solution thus obtained was condensed using an ultrafiltration membrane made of polyethersulfone (having a molecular weight cut-off of 10,000, and manufactured by Millipore Corporation, model number PBGC07610) to obtain 50 ml of condensate. 300 ml of distilled water were added to the condensate, and the resulting solution was again condensed in the same manner. This cycle of diluting the condensate with distilled water followed by re-condensation was repeated five times to eliminate excess 1-amino-2-propanol. The resulting condensate was freeze-dried to obtain 1.3 g of the title compound poly($PEG_{500}$-MA)ipa (Compound No. 5) as an oily compound.

The carboxyl group content in 1 g of poly($PEG_{500}$-MA)ipa (Compound No. 5) was determined in the same manner as described in Example 1 above, and was determined to be 1.55 mmols. Using a calculation similar to that in Example 3 for the ammonolysis product, the theoretical carboxyl group content in 1 g of poly($PEG_{500}$-MA)ipa (Compound No. 5) where all maleic anhydride residues have been subjected to aminolysis was determined by calculation, and was determined to be 1.47 mmols. From these results, the ratio of maleic anhydride residues subjected to aminolysis in the title compound to the total number of maleic anhydride residues in the starting material was calculated, and was determined to be 1.0. Thus, it was confirmed that substantially all maleic anhydride residues in the starting material had been subjected to aminolysis by 1-amino-2-propanol and that virtually no hydrolysis had taken place.

Example 6

Product of alcoholysis reaction between ethanol and poly($PEG_{500}$-MA) [poly($PEG_{500}$-MA)ea)] wherein m=6-16, $R^3$=OCH$_2$CH$_3$, comp. ratio=about 1:1, av. deg. pol.=30-40 and hyd. ratio=about 4:6 (Compound No. 6)

25 g of absolute ethanol were added to 1.5 g of poly($PEG_{500}$-MA) (AM-0530K, manufactured by NOF Corporation) to dissolve it, and the solution thus obtained was stirred at room temperature for 16 hours. At the end of this time, 300 ml of water were added, and the resulting solution was condensed using an ultrafiltration membrane made of polyethersulfone (having a molecular weight cut-off of 10,000 and manufactured by Millipore Corporation, model number PBGC07610) to obtain 50 ml of condensate. 300 ml of distilled water were added to the condensate, and the resulting solution was again condensed in the same manner. This cycle of diluting the condensate with distilled water followed by re-condensation was repeated five times to eliminate excess ethanol. The resulting condensate was freeze-dried to obtain 0.8 g of the title compound poly($PEG_{500}$-MA)ea (Compound No. 6) as an oily compound.

The carboxyl group content in 1 g of poly($PEG_{500}$-MA)ea (Compound No. 6) was determined in the same manner as described in Example 1 above, and was determined to be 2.16 mmols. Using a calculation similar to that in Example 3 for the ammonolysis product, the theoretical carboxyl group content in 1 g of poly($PEG_{500}$-MA)ea (Compound No. 6) where all maleic anhydride residues have been subjected to alcoholysis was determined by calculation, and was determined to be 1.47 mmols. From the result, the ratio of maleic anhydride residues in the title compound subjected to alcoholysis to the total number of maleic anhydride residues in the starting material was calculated, and was determined to be 0.6. Thus, it can be seen that 60% of maleic anhydride residues in the starting material were subjected to alcoholysis, and the remaining 40% of maleic anhydride residues were subjected to hydrolysis.

Example 7

Preparation of product of ammonolysis of poly($PEG_{1500}$-MA) [poly($PEG_{1500}$-MA)a)] wherein m=28-38, $R^3$=NH$_2$, comp. ratio=about 1:1, av. deg. pol.=10-15 and hyd. ratio=about 4:6 (Compound No. 7)

14.5 g of ammonia water (ammonia concentration: 28 wt %) were added to 1.5 g of poly($PEG_{1500}$-MA) (AM-1510K, manufactured by NOF Corporation) to dissolve it, and the solution thus obtained was stirred at room temperature for 20 hours. At the end of this time, 300 ml of distilled water were added to the solution, and glacial acetic acid was further added to neutralize said solution. The resulting solution was condensed using an ultrafiltration membrane made of polyethersulfone (having a molecular weight cut-off of 10,000 and manufactured by Millipore Corporation, model number PBGC07610) to obtain 50 ml of condensate. 300 ml of distilled water were added to the condensate, and the resulting solution was again condensed in the same manner. This cycle of diluting the condensate with distilled water followed by re-condensation was repeated five times to eliminate excess ammonia. The resulting condensate was freeze-dried to obtain 0.7 g of the title compound poly($PEG_{1500}$-MA)a (Compound No. 7) as an oily compound.

The carboxyl group content in 1 g of poly($PEG_{1500}$-MA)a was determined in the same manner as in Example 1, and was found to be 1.12 mmols. As with the ammonolysis of poly($PEG_{500}$-MA)a of Example 3, there is a possibility that the maleic anhydride residues in the poly($PEG_{1500}$-MA) starting material could be subjected to both ammonolysis and hydrolysis. Therefore the ratio of maleic anhydride residues subjected to ammonolysis to the ratio of maleic anhydride residue subjected to hydrolysis was calculated as follows.

In Example 2, the carboxyl group content in 1 g of poly($PEG_{1500}$-MA)h (Compound No. 2) was determined. This gives the figure for carboxyl group content when all maleic acid residues are fully hydrolysed (1.63 mmols per 1 g of polymer). From this result, the weight of poly($PEG_{1500}$-MA)h (Compound No. 2) per mol of carboxyl group (1/1.63× $10^{-3}$ g) and the weight of poly($PEG_{1500}$-MA)h (Compound No. 2) per mol of ring-opened maleic acid residue [2×the weight of poly($PEG_{1500}$-MA)h (Compound No. 2) per mol of ring-opened maleic acid residue, since there are 2 carboxyl groups per fully hydrolysed maleic acid residue] were calculated, giving the results 613 g and 1,227 g, respectively. From the thus-obtained weight of poly($PEG_{1500}$-MA)h, and using an approach similar to that in Example 3 above, the theoretical carboxyl group content per 1 g of poly($PEG_{1500}$-MA)a (Compound No. 7) where all maleic anhydride residues have been subjected to ammonolysis, was calculated, and was determined to be 0.82 mmols. From these values and the actual carboxyl group content of poly($PEG_{1500}$-MA)a (Compound No. 7) measured above (1.12 mmols), the ratio of maleic anhydride residues in the title compound subjected to ammonolysis to the total number of maleic anhydride residues in the starting material was determined by calculation, and was found to be 0.6. Thus, it was confirmed that 60% of the maleic anhydride residues in the poly($PEG_{1500}$-MA) starting material were subjected to ammonolysis, and the remaining 40% of maleic anhydride residues were subjected to hydrolysis.

Example 8

Preparation of reaction product of dimethylamine and poly($PEG_{1500}$-MA) [poly($PEG_{1500}$-MA)dma)] wherein m=28-38, $R^3$=$NMe_2$, comp. ratio=about 1:1, av. deg. pol.=10-15 and hyd. ratio=about 0:10 (Compound No. 8)

11 g of an aqueous dimethylamine solution (having a concentration of 50 wt %) were added to 1 g of poly($PEG_{1500}$-MA) (AM-1510K, manufactured by NOF Corporation) to dissolve it, and the solution thus obtained was stirred at room temperature for 20 hours. At the end of this time, 300 ml of distilled water were added to the solution, and glacial acetic acid was further added to neutralize the solution. The resulting solution was condensed using an ultrafiltration membrane made of polyethersulfone (having a molecular weight cut-off of 10,000 and manufactured by Millipore Corporation, model number PBGC07610) to obtain 50 ml of condensate. 300 ml of distilled water were added to the condensate, and the resulting solution was again condensed in the same manner. This cycle of diluting the condensate with distilled water followed by re-condensation was repeated five times to eliminate excess dimethylamine. The resulting condensate was freeze-dried to obtain the title compound poly($PEG_{1500}$-MA)dma (Compound No. 8) as an oily compound.

The carboxyl group content in 1 g of poly($PEG_{1500}$-MA)dma (Compound No. 8) was determined in the same manner as in Example 1, and was calculated to be 0.82 mmols. Using a similar approach to that used in Example 3, the theoretical carboxyl group content in 1 g of poly($PEG_{1500}$-MA)dma where all maleic anhydride residues have been subjected to aminolysis was determined by calculation to be 0.80 mmol. From these results, the ratio of maleic anhydride residues in the title compound subjected to aminolysis to the total number of maleic anhydride residues in the starting material was determined by calculation, and was found to be 1.0. Thus, it was confirmed that substantially all maleic anhydride residues had been subjected to aminolysis by dimethylamine.

Example 9

Preparation of Complexes of Polymeric Modifiers of Examples 1 to 8 with OCIF

Each of the polymeric modifiers prepared in Examples 1 to 8 was dissolved in phosphate buffer saline (PBS) pH 6.0 (which is solution obtained by mixing a solution containing 10 mM disodium hydrogen phosphate and 150 mM sodium chloride and a solution containing 10 mM sodium dihydrogen phosphate and 150 mM sodium chloride at a suitable ratio to give a buffer having a pH of 6.0) to prepare solutions having a modifier concentration of from 1 to 20 mg/ml. For each solution of each modifier in turn, 0.625 ml of the prepared polymeric modifier solution and 0.625 ml of a solution containing purified human mature OCIF (OCIF prepared as described in WO 96/26217 and EP 816380) [protein concentration: 2 mg/ml, medium: PBS (pH 6.0)] were mixed, and the mixture thus obtained was allowed to stand at 4° C. to 37° C. for at least one hour, to give a series of solutions [medium: PBS (pH 6.0)] containing OCIF modified with the polymeric modifiers of Examples 1 to 8 in which the ratio of modifier to OCIF in each solution is determined by the concentration of the modifier solution added and the reaction conditions. The weight ratios of modifier/OCIF for some of the complexes prepared (and the conditions under which they were prepared) are shown in Table 6 in Test Example 2 below. The molecular size of each of the resulting complexes was measured as explained in Test Example 11 below. The detection rate of OCIF by ELISA in the complexes was measured as described in Test Example 3 below.

Additionally, for each of the polymeric modifiers, a solution of OCIF modified with the polymeric modifier was prepared in the same manner except that PBS with a pH of 7.4 was used as the medium.

Example 10

Preparation of sodium salt of product of ammonolysis of poly($PEG_{500}$-MA) [poly($PEG_{500}$-MA)a)-Na] wherein m=6-16, $R^3$=$NH_2$, comp. ratio=about 1:1, av. deg. pol.=30-40 and hyd. ratio=about 3.1:6.9 (Compound No. 9)

A copolymer of polyoxyethylene allyl methyl diether (m=6-16, Alk =ethylene, $R^1$=hydrogen and $R^2$=methyl) and maleic anhydride, in which the polyoxyethylene side chain has an average molecular weight of about 500 and the average degree of polymerization of the main chain is in the range of from 30 to 40 (AM-0530K, manufactured by NOF Corporation, having a lot number of M34529) [hereinafter referred to as "poly($PEG_{500}$-MA)"] was used as the starting material. 61 ml of a 0.5M ammonia/1,4-dioxane solution were added to 10.1 g of said poly($PEG_{500}$-MA) starting material, and the resulting solution was stirred at 25° C. for 20 hours. At the end of this time, 200 ml of diethyl ether and 100 ml of a 0.2M sodium hydroxide aqueous solution were added to the solution, and the mixture vigorously shaken for about 3 minutes. After allowing phase separation of the organic and aqueous layers, the lower layer was collected. 200 ml of diethyl ether and 60 ml of 1,4-dioxane were added to the collected layer, and the solution thus obtained was again vigorously shaken. After phase separation, the resulting lower layer was collected and then freeze-dried to obtain 10.1 g of the title compound poly($PEG_{500}$-MA)a sodium salt (Compound No. 9) as a yellow solid.

The carboxyl group content and hydrolysis ratio for the title polymer was determined as described in Test Example 1 below.

Example 11

Preparation of product of ammonolysis of poly ($PEG_{500}$-MA) [poly($PEG_{500}$-MA)a)] wherein m=6-16, $R^3$=$NH_2$, comp. ratio=about 1:1, av. deg. pol.=30-40 and hyd. ratio=about 1.4:8.6 (Compound No. 10)

9.5 g of 28 w/w % ammonia water were added to 1 g of poly($PEG_{500}$-MA) (AM-0530K, manufactured by NOF Corporation, having a lot number of M34529) to dissolve it, and the solution thus obtained was stirred at 25° C. for 4 hours. At the end of this time, 250 ml of 0.28% ammonia water were added, and the resulting solution was condensed using an ultrafiltration membrane made of polyethersulfone (having a molecular weight cut-off of 10,000 and manufactured by Millipore Corporation, model number PBGC07610), and the condensate thus obtained was freeze-dried to obtain 0.8 g of the title compound poly($PEG_{500}$-MA)a (Compound No. 10) as an oily compound.

The carboxyl group content and hydrolysis ratio for the title polymer was determined as described in Test Example 1 below.

Example 12

Preparation of reaction product of dimethylamine and poly($PEG_{500}$-MA) [poly($PEG_{500}$-MA)dma)-Na salt] wherein m=6-16, $R^3$=$NMe_2$, comp. ratio=about 1:1, av. deg. pol.=30-40 and hyd. ratio=about 2.9:7.1 (Compound No. 11)

35 g of a 50 w/w % aqueous dimethylamine solution were added to 5 g of poly($PEG_{500}$-MA) (AM-0530K, lot number: M34529 obtained from NOF Corporation) to dissolve it, and the resulting solution was stirred at 25° C. for 3 hours, then further stirred at 4° C. for 16 hours. At the end of this time, 100 ml of a 0.1M sodium hydroxide aqueous solution were added, and the solution thus obtained was freeze-dried to obtain 5.4 g of the title compound poly($PEG_{500}$-MA)dma-Na salt (Compound No. 11) as a yellow solid.

The carboxyl group content and hydrolysis ratio for the title polymer was determined as described in Test Example 1 below.

Example 13

Preparation of poly($PEG_{500}$-MA) hydrolysate [poly ($PEG_{500}$-MA)h)] wherein m=6-16, $R^3$=OH, comp. ratio=about 1:1, av. deg. pol.=30-40 and hyd. ratio=about 10:0 (Compound No. 12)

17 ml of distilled water were added to 1 g of poly($PEG_{500}$-MA) (AM-0530K, manufactured by NOF Corporation, having a lot number of M34529) to dissolve it, and the resulting solution was stirred at 40° C. for 4 hours. At the end of this time, 250 ml of 0.28 w/w % ammonia water were added thereto, and the solution thus obtained was condensed using an ultrafiltration membrane made of polyethersulfone (having a molecular weight cut-off of 10,000, and manufactured by Millipore Corporation, model number PBGC07610). The condensate thus obtained was freeze-dried to obtain 0.7 g of the title compound poly($PEG_{500}$-MA)h (Compound No. 12) as an oily compound.

The carboxyl group content and hydrolysis ratio for the title polymer was determined as described in Test Example 1 below.

Example 14

Preparation of Complexes of Polymeric Modifiers of Examples 10 to 13 with OCIF

Each of the polymeric modifiers prepared in Examples 10 to 13 was dissolved in phosphate buffer saline (PBS) pH 7.0 (which is a solution obtained by mixing a solution containing 10 mM disodium hydrogen phosphate and 150 mM sodium chloride and a solution containing 10 mM sodium dihydrogen phosphate and 150 mM sodium chloride at a suitable ratio to give a buffer having a pH of 7.0) to prepare solutions having a range of modifier concentrations in the range of from 1.25 to 105 mg/ml. For each polymeric modifier in turn, the polymeric modifier solutions thus obtained and a solution containing purified human mature OCIF (OCIF prepared as described in WO 96/26217 and EP 816380) [protein concentration: 0.25 to 14 mg/ml, medium: PBS (pH 6.0)] were mixed at a 1:1 ratio by volume to give solutions having different weight ratios between the modifier and OCIF. The solutions thus obtained were adjusted to pH 5.0, 5.5, 6.0, 6.5, 7.0 or 7.4 using 1 M hydrochloric acid solution or 1 M aqueous sodium hydroxide. Each of the solutions thus obtained was allowed to stand at 25° C. for between 12 hours and one week to obtain a solution of a complex of the polymeric modifier of the present invention and OCIF. The prepared solutions were stored at 4° C. The molecular size of the resulting complexes was measured as explained in Test Examples 6 and 11 below. The detection rate of OCIF by ELISA in the complexes was measured as described in Test Example 8 below.

Example 15

Preparation of sodium salt of the product of ammonolysis of poly($PEG_{500}$-MA) [poly($PEG_{500}$-MA)$_a$-Na salt] having controlled molecular size wherein m=6-16, $R^3$=$NH_2$, comp. ratio=about 1:1, av. deg. pol as shown below and hydrolysis ratio=about 1.4:8.6 (Compound Nos. 13-19)

100 mg of the sodium salt of poly($PEG_{500}$-MA)a (Compound No. 9) obtained in Example 10 were dissolved in 1 ml of a phosphate buffer saline solution (PBS having a pH of 7.4 obtained by mixing an aqueous solution containing 10 mM of disodium hydrogenphosphate and 150 mM of sodium chloride with an aqueous solution containing 10 mM of sodium dihydrogenphosphate and 150 mM of sodium chloride at a suitable ratio). The solution thus obtained was fractionated by gel filtration chromatography. Two different gel filtration conditions were used, as follows:

(1) Fractionation method using Superose 6 (herinafter referred to as the SRF method)

Column: Superose 6 HR 10/30 Amersham Bioscience

Column temperature: 8° C.

Mobile phase: PBS (pH 7.4)

Wavelength for detection: 280 nm
Flow rate: 0.3 ml/min
Amount injected on to column: 100 μl (2) Fractionation method using Superdex 200 (herinafter referred to as the SDF method)
Column: Superdex 200 HR 16/60 Amersham Biosciences
Column temperature: room temperature
Mobile phase: PBS (pH 7.4)
Wavelength for detection: 280 nm
Flow rate: 2 m/min
Amount injected on to column: 5 ml Polymeric modifiers that were eluted by these two fractionation methods in an elution time of x to y minutes were defined as poly(PEG$_{500}$-MA)$_a$-Na(SRF$_{x-y}$) and poly (PEG$_{500}$-MA)$_a$-Na(SDF$_{x-y}$) respectively.

The concentration of the polymeric modifier in each fraction (aqueous solution) was determined by high performance liquid chromatography. The conditions used in the high performance liquid chromatography are as follows:
Column: Shodex OHpak SB-806M HQ (available from SHOWA DENKO K.K.)
Guard column: Shodex OHpak SB-G (available from SHOWA DENKO K.K.)
Column temperature: 40° C.
Mobile phase: aqueous solution of 50 mM disodium hydrogenphosphate adjusted to pH 7.0 with 1M hydrochloric acid
Wavelength for detection: 210 nm
Flow rate: 0.5 ml/min
Amount injected on to column: 50 μl Poly(PEG$_{500}$-MA)$_a$-Na(SRF$_{x-y}$) and poly(PEG$_{500}$-MA)$_a$-Na(SDF$_{x-y}$) respectively obtained by fractionation according to the SRF method and the SDF method were subjected to further gel filtration chromatography (SRF method) using the same elution conditions as described above for the first fractionation according to the SRF method to evaluate the molecular size of each of the samples after fractionation. Proteins each having a known molecular size (available from Amersham Bioscience) were used as standard samples. In this respect, the molecular weight and molecular size of each of the proteins are shown in the relevant catalogue from which they were purchased.

The calculated molecular size of the polymer modifiers obtained by fractionation are shown in Table 1 below.

TABLE 1

|  | Molecular weight | Stokes radius (nm) | Retention time (min) | Cpd. No. |
|---|---|---|---|---|
| Standard protein |  |  |  |  |
| Thyroglobulin | 669 k | 8.50 | 38.48 |  |
| Ferritin | 440 k | 6.10 | 44.85 |  |
| Catalase | 232 k | 5.22 | 48.77 |  |
| Aldolase | 158 k | 4.81 | 50.11 |  |
| Albumin | 67 k | 3.55 | 51.85 |  |
| Ovalbumin | 43 k | 3.05 | 53.95 |  |
| Chymotripsinogen A | 25 k | 2.09 | 59.26 |  |
| Ribonuclease A | 13.7 k | 1.64 | 60.23 |  |
| Modifier of Ex. 15 |  |  |  |  |
| poly(PEG$_{500}$-MA)$_a$-Na (non fractionated) |  | 9.3 or less** | 35-65* | 9 |
| poly(PEG$_{500}$-MA)$_a$-Na (SRF$_{50-55}$) yield 23% |  | 3.1-6.2** | 45-55* | 13 |
| poly(PEG$_{500}$-MA)$_a$-Na (SRF$_{55-60}$) yield 29% |  | 1.5-4.7** | 50-60* | 14 |
| poly(PEG$_{500}$-MA)$_a$-Na (SRF$_{60-65}$) yield 12% |  | 3.1 or less** | 55-65* | 15 |

TABLE 1-continued

|  | Molecular weight | Stokes radius (nm) | Retention time (min) | Cpd. No. |
|---|---|---|---|---|
| poly(PEG$_{500}$-MA)$_a$-Na (SDF$_{46-52}$) yield 22% |  | 7.8 or less** | 40-65* | 16 |
| poly(PEG$_{500}$-MA)$_a$-Na (SDF$_{52-58}$) yield 22% |  | 6.2 or less** | 45-65* | 17 |
| poly(PEG$_{500}$-MA)$_a$-Na (SDF$_{58-64}$) yield 13% |  | 3.1 or less** | 55-65* | 18 |
| poly(PEG$_{500}$-MA)$_a$-Na (SDF$_{60-70}$) yield 13% |  | 3.1 or less** | 55-65* | 19 |

*The presence of a span of the retention time indicates that the sample has a molecular weight distribution.
**This is a value calculated from a calibration curve produced using the molecular size and retention time of each of the standard proteins. In those cases where a lower limit is not shown, that is, where the Stokes radius is shown as "XX or less", it can be said that the sample contains a low molecular weight component which can not evaluated by gel filtration chromatography carried out under the conditions of this example.

Using this approach, various poly(PEG$_{500}$-MA)$_a$-Na polymers having different molecular sizes were prepared (Compound Nos. 13-19). The average degree of polymerization of Compound Nos. 13, 14, 15, 16, 17, 18 and 19 was calculated as in earlier examples and was found to be <30, <<30, <<<30, <30, <<30, <<<30 and <<<30 respectively.

Example 16

Preparation of the product of ammonolysis of poly (PEG$_{1500}$-MA) [poly(PEG$_{1500}$-MA)$_a$] having controlled molecular size wherein m=28-38, R$^3$=NH$_2$, comp. ratio=about 1:1, av. deg. pol. is as given below
(Compound Nos. 20-22)

Starting with [poly(PEG$_{1500}$-MA)$_a$] (Compound No. 7) prepared in Example 7 above as a starting material and using the same approach as used in Example 15 above, Poly (PEG$_{1500}$-MA)$_a$(SRF$_{x-y}$) was prepared in the same manner as in Example 15. The elution conditions for the SRF elutions were the same as in Example 15. The yields of the polymer modifiers obtained by fractionation are shown in Table 2 below.

TABLE 2

| Modifier of Example 16 | Compd. No. |
|---|---|
| poly(PEG$_{1500}$-MA)$_a$ (non fractionated) | 7 |
| poly(PEG$_{1500}$-MA)$_a$ (SRF$_{50-55}$) 12.2% | 20 |
| poly(PEG$_{1500}$-MA)$_a$ (SRF$_{55-60}$) 13.1% | 21 |
| poly(PEG$_{1500}$-MA)$_a$ (SRF$_{60-65}$) 16.4% | 22 |

Using this approach, various poly(PEG$_{1500}$-MA)a polymers having different molecular sizes were prepared (Compound Nos. 20-22). The average degree of polymerisation of Compound Nos. 20, 21 and 22 was calculated as in earlier examples and was found to be <10, <<10 and <<<10 respectively.

Example 17

Preparation of Complexes of Polymeric Modifiers of Examples 15 and 16 with OCIF

Polymer-OCIF complexes of the present invention were prepared as aqueous solutions using essentially the same preparative approach as in Example 14 above using aqueous solutions of Compound Nos. 13 to 22 prepared in Examples 15 and 16 above (medium: PBS having a pH of 7.4) and an aqueous solution of purified human mature OCIF (OCIF prepared as described in WO 96/26217 and EP 816380) (medium: PBS having a pH of 6.0) as the starting materials. More specifically, for each of the modifiers a 0.5 mg/ml solution thereof in PBS (pH 7.4) (prepared as described in Example 9 above) was mixed with a solution of 0.5 mg/ml OCIF in PBS (pH 6.0) at a volume ratio of 1:1. The resulting reaction mixtures were allowed to stand at 25° C. for 7 days. The molecular size of the resulting complexes was measured as explained in Test Example 11 below.

Example 18

Preparation of the product of ammonolysis of poly (PEG$_{500}$-MA) [poly(PEG$_{500}$-MA)$_a$-Na salt] having controlled molecular size: (a) m=6-16, R$^3$=NH$_2$, comp. ratio=about 1:2 and av. deg. pol.=20-30 (Comp. No. 27) and (b) m=6-16, R$^3$=NH$_2$, comp. ratio=about 1:1 and av. deg. pol.=about 15 (Comp. No. 28)

Two polymers of the present invention poly(PEG$_{500}$-MA)$_a$ (Compound No. 27) and poly(PEG$_{500}$-MA)$_a$ (Compound No. 28) were prepared as follows. The starting material for the former is poly(PEG$_{500}$-MA) (AM-0510K manufactured using a procedure similar to that disclosed in Japanese Patent No. 2621308 and Japanese Patent Application Publication Nos. 2003-105040 and 2003-104003), a copolymer of polyoxyethylene allyl methyl diether (m=6-16, Alk=ethylene, R$^1$=hydrogen and R$^2$=methyl) and maleic anhydride, in which the polyoxyethylene side chain has an average molecular weight of about 500 and the average degree of polymerization of the main chain is in the range of from 20 to 30, the ratio of polyoxyethylene allyl methyl diether units to maleic anhdride units being 1:2 and the average molecular weight being about 6,000 [number-average molecular weight is about 6,000 and the molecular weight distribution index (Mw/Mn) is about 1.25]. The starting material for the latter is poly(PEG$_{500}$-MA) (AM-0515K manufactured using a procedure similar to that disclosed in Japanese Patent No. 2621308 and Japanese Patent Application Publication Nos. 2003-105040 and 2003-104003), a copolymer of polyoxyethylene allyl methyl diether (m=6-16, Alk=ethylene, R$^1$=hydrogen and R$^2$=methyl) and maleic anhydride, in which the polyoxyethylene side chain has an average molecular weight of about 500, the average degree of polymerization of the main chain is about 15 and the average molecular weight is about 10,000. The starting materials were both subjected to ammonolysis using conditions essentially identical to those used in Example 10 to give the title compounds poly(PEG$_{500}$-MA)$_a$-Na salt (Compound No. 27) and poly(PEG$_{500}$-MA)$_a$-Na salt (Compound No. 28). The carboxyl group content for the title polymer was determined as described in Test Example 1 below and found to be 2.73 mmol/g for Compound No. 27 and 2.05 mmol/g for Compound No. 28.

Example 19

Preparation of Complexes of the Polymeric Modifiers of Example 18 with OCIF

Polymer-OCIF complexes of the present invention were prepared as aqueous solutions using essentially the same preparative approach as in Example 14 above using aqueous solutions of Compound Nos. 27 and 28 prepared in Example 18 above as the starting materials. More specifically, for each of the modifiers a 5 mg/ml solution thereof in PBS (pH 7.4) was mixed with a solution of 5 mg/ml human mature OCIF in PBS (pH 6.0) at a volume ratio of 1:1. The pH of the resulting mixture was adjusted to 5.5 with 1M hydrochloric acid and then the reaction mixture was allowed to stand at 25° C. for 7 days. The molecular size of the resulting complexes was measured as explained in Test Example 11 below.

Example 20

Evaluation of composition of poly(PEG$_{500}$-MA) and preparation and evaluation of poly(PEG$_{500}$-MA)a (Compound Nos. 29-53) under various conditions 20(1) Determination of composition ratio of poly(PEG$_{500}$-MA)

A number of copolymers of polyoxyethylene allyl methyl diether and maleic anhydride, poly(PEG$_{500}$-MA), of differing composition were tested to determine the ratio of PEG allyl methyl diether and maleic anhydride units (the composition ratio) therein (different lots of AM-050K manufactured using a procedure similar to that disclosed in Japanese Patent No. 2621308 and Japanese Patent Application Publication Nos. 2003-105040 and 2003-104003), a random copolymer of polyoxyethylene allyl methyl diether (m=6-16, Alk=ethylene, R$^1$=hydrogen and R$^2$=methyl) and maleic anhydride, in which the polyoxyethylene side chain has an average molecular weight of about 500 and the average degree of polymerization of the main chain is in the range of from 20 to 30. The number-average molecular weight (M$_n$) and molecular weight distribution index (M$_w$/M$_n$, where M$_w$ is weight-average molecular weight) of each lot of the copolymers tested is shown below. The molecular weight (MW) of each lot of poly(PEG$_{500}$-MA) was determined by gel filtration chromatography using poly(ethylene glycol) with a predetermined MW as a standard. Consequently, the MW of poly(PEG$_{500}$-MA) shown below is not the absolute MW, but the relative MW measured using PEG as a standard.

M3O538 M$_n$=6431; M$_w$/M$_n$=1.27
M3N549 M$_n$=6360; M$_w$/M$_n$=1.23
M3N550 M$_n$=5891; M$_w$/M$_n$=1.28
M3N569 M$_n$=5897; M$_w$/M$_n$=1.25

In order to determine the composition ratio of each of the copolymers, it was necessary to convert them to the corresponding sodium salts of the hydrolysed copolymers, i.e. poly(PEG$_{500}$-MA)h sodium salt. The hydrolysis conditions used are as follows.

25 ml of 1,4-dioxane, 100 ml of ether and 42 ml of 0.1 N NaOH aqueous solution were added to 1 g of poly(PEG$_{500}$-MA) (lot M30538). The resulting mixture was then vigorously shaken and, after allowing it to settle, the aqueous layer thus obtained was collected. The aqueous layer thus obtained was stirred at 40° C. for 2 h after filtering through filter paper (704×40 m/m obtained from Nihon Rikagaku-kiki Corporation). At the end of this time, the resulting solution was freeze-dried. The sodium salt of the hydrolyzed product of the starting material, namely poly(PEG$_{500}$-MA)h (lot M30538) sodium salt, was obtained as a yellow solid (100% yield).

12 ml of 1,4-dioxane and 9 ml of 1 N NaOH aqueous solution were added to 1 g of poly(PEG$_{500}$-MA) (lot M3N549). The resulting mixture was then stirred at room temperature for 24 h. At the end of this time, 1 ml of 1 N NaOH aqueous solution was added and the resulting mixture was freeze-dried. The sodium salt of the hydrolyzed product of the starting material, namely poly(PEG$_{500}$-MA)h (M3N549) sodium salt was obtained as a yellow solid (100% yield).

5 ml of 1,4-dioxane and 9 ml of 1 N NaOH aqueous solution were added to 2 g of poly(PEG$_{500}$-MA) (lot M3N550). The resulting mixture was then stirred at 40° C. for 23 h. At the end of this time, the reaction mixture was freeze-dried. The sodium salt of the hydrolyzed product of the starting material, namely poly(PEG$_{500}$-MA)h (lot M3N550) sodium salt was obtained as a yellow solid (100% yield).

5 ml of 1,4-dioxane and 9 ml of 1 N NaOH aqueous solution were added to 2 g of poly(PEG$_{500}$-MA) (lot M3N569). The resulting mixture was then stirred at 40° C. for 23 h. At the end of this time, the reaction mixture was freeze-dried. The sodium salt of the hydrolyzed product of the starting material, namely poly(PEG$_{500}$-MA)h was obtained as a yellow solid (100% yield).

The carboxyl group content of each of the poly(PEG$_{500}$-MA)h sodium salts thus prepared was measured by conductometric titration as described above. The results are shown in Table 3 below.

Poly(PEG$_{500}$-MA)h sodium salt comprises the following two monomer units:

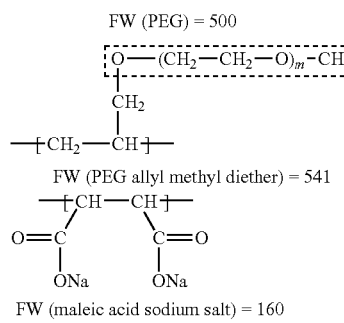

If the number of maleic acid sodium salt monomer units per 1 unit of PEG allyl methyl diether is defined as "a", and the theoretical minimum repeating unit comprises one unit of PEG allyl methyl diether and "a" units of sodium maleate, then the formula weight (FW) of the minimum repeating unit is given by equation 1:

$$FW = [(PEG \text{ allyl methyl diether})_1 + \text{(maleic acid sodium salt)}_a] \quad \text{(Eq. 1)}$$
$$= FW(PEG \text{ allyl methyl diether}) + a[FW\text{(maleic acid sodium salt)}]$$
$$= 541 + 160a$$

The number of carboxyl groups on the minimum repeating unit of poly(PEG$_{500}$-MA)h sodium salt is 2a. Consequently, the carboxyl group content (C, mmol/g) on the minimum repeating unit of poly(PEG$_{500}$-MA)h sodium salt is given by equation 2:

$$C = 2a/(541+160a)*1000 \quad \text{(Eq. 2)}$$

The ratio of the number of maleic acid sodium salt units to the number of PEG allyl methyl diether units in the actual poly(PEG$_{500}$-MA)h sodium salts is the same as the ratio in the minimum repeating units. Consequently, the value of C is also the same in the minimum repeating unit and in the actual poly(PEG$_{500}$-MA)h sodium salts, the carboxyl group contents of which were determined by conductometric titration (see above). Thus, by measuring the carboxyl group content and using Equation 2, the value of the composition ratio "a", namely the number of maleic acid sodium salt units per 1 unit of PEG allyl methyl diether [which is the monomer composition of poly(PEG$_{500}$-MA)] can be obtained. The results are shown in Table 3 below.

TABLE 3

| | poly(PEG500-MA) bt | Amount of carboxyl groups (mmol/g) | MA/PEG allylmethyl diether |
|---|---|---|---|
| poly(PEG500-MA)h sodium salt | #1 M 3O 538 | 4.66 | 2.01 |
| | #2 M 3N 549 | 5.21 | 2.42 |
| | #3 M 3N 550 | 5.98 | 3.10 |
| | #4 M 3N 569 | 6.14 | 3.26 |

The composition ratio of the poly(PEG$_{500}$-MA)h sodium salts was in the range of from 1:2 to 1:3.3. Obviously, the composition ratio is the same in poly(PEG$_{500}$-MA) and poly(PEG$_{500}$-MA)h sodium salt, such that monomer composition ratios of the different starting copolymers poly(PEG$_{500}$-MA) were confirmed to be in the range of from 1:2 to 1:3:3.

20(2) Ammonolysis of poly(PEG$_{500}$-MA) under different conditions to give poly(PEG$_{500}$-MA)a (Compound Nos. 29-53) and determination of hydrolysis ratios in said compounds By using the composition ratio (a) and the carboxyl group content of the poly(PEG$_{500}$-MA)h sodium salts, the hydrolysis ratio (i.e. the ratio of maleic acid anhydride units in the starting polymer subjected to ammonolysis to those subjected to hydrolysis) can be calculated as follows. The formula of the sodium salt of amidated maleic acid (maleamic acid, sodium salt) unit is shown below:

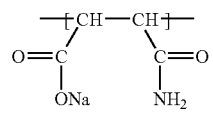

FW (maleamic acid sodium salt) = 137

In the same manner as the case of the poly(PEG$_{500}$-MA)h sodium salts above, it can be assumed that the minimum unit of poly(PEG$_{500}$-MA)a sodium salt comprises one PEG allyl methyl diether unit, ax units of maleamic acid sodium salt and a(1-x) units of maleic acid sodium salt. The formula weight of the minimum unit of poly(PEG$_{500}$-MA)a sodium salt is given by the following Equation 3:

$$FW[(PEG \text{ allyl methyl diether})_1 + \text{(maleamic acid sodium salt)}_{ax} + \text{(maleic acid sodium salt)}_{a(1-x)}] \quad \text{(Eq. 3)}$$
$$= FW(PEG \text{ allyl methyl diether}) + ax[FW\text{(maleamic acid sodium salt)}] + a(1-x)[FW\text{(maleic acid sodium salt)}]$$
$$= 541 + 137ax + 160a(1-x)$$
$$= 541 + 160a - 23ax$$

Since the carboxyl group content in the minimum unit of poly(PEG$_{500}$-MA)a sodium salt is $ax+2a(1-x)=2a-ax$, the carboxyl group content (C, mmol/g) in the minimum unit of poly(PEG$_{500}$-MA)a sodium salt can be derived from Equation 4:

$$C = 1000 \times (2a - ax)/(541 + 160a - 23ax) \quad \text{(Eq. 4)}$$

The hydrolysis ratio $(1-x):x$ can thus be determined from Equation 4 by using the carboxyl group content (C, mmol/g) that can be obtained by conductometric titration of poly(PEG$_{500}$-MA)a sodium salt and the value of "a" that was obtained above.

Several examples of the preparation of poly(PEG$_{500}$-MA)a, and the calculated hydrolysis ratio in the product poly(PEG$_{500}$-MA)a are shown below.

(a) 0.5 M ammonia/1,4-dioxane solution (amounts as given in Table 4 below) was added to 100 mg of poly(PEG$_{500}$-MA), and the obtained solution was stirred at the temperatures and times given in Table 4 below. At the end of the reaction time, about 0.4 ml (ranging from 0.3 to 0.5 ml) of 1N NaOH aqueous solution was added to the reaction mixture. The resulting solution was freeze-dried to obtain the sodium salt of poly(PEG$_{500}$-MA)a as a solid material.

The "reaction rate of amine component" of each of the poly(PEG$_{500}$-MA)a sodium salts [i.e. the percentage of maleic acid anhydride units in the starting polymer subjected to ammonolysis (100*x)] prepared under these various reaction conditions is shown in Table 4 below.

As shown in Table 4, the reaction products poly(PEG$_{500}$-MA)a (Compound Nos. 29-52) all had very high "reaction rates of the amine component", indicating that very nearly 100% conversion to the amino group was obtained using the various reaction conditions described above.

Several further examples of alternative preparation methods of poly(PEG$_{500}$-MA)a are described below:

(b) 0.44 g of poly(PEG$_{500}$-MA) was dissolved in 9 ml of dimethylformamide. Ammonia gas was then bubbled into the solution at −50° C. The final ammonia amount in the reaction mixture was 0.67 g. The reaction mixture thus obtained was sealed in a glass ampoule under a nitrogen atmosphere, and then stirred at room temperature for 24 h. At the end of this time, ammonia gas was evaporated under reduced pressure after the glass ampoule was opened. The reaction mixture was then added dropwise to 90 ml of diethyl ether. The precipitate thus obtained was collected and dried under reduced pressure. 0.28 g of poly(PEG$_{500}$-MA)a ammonium salt (Compound No. 53) (referred to as #41 in Table 4 above) was obtained as a yellow powder. The polymer is random and m=6-16, $R^3$=NH$_2$, composition ratio=1:3.10 and average degree of polymerisation=20-30.

(c) Poly(PEG$_{500}$-MA)a ammonium salt was obtained in the same way as (b) using toluene instead of dimethylformamide.

(4) Poly(PEG$_{500}$-MA)a ammonium salt was obtained in the same way as (b) using 1,4-dioxane instead of dimethylformamide.

TABLE 4

| | | poly(PEG-MA) bt | 0.5 M NH3 added | Reaction Temp. | Reaction Time | Amount of carboxyl groups (mmol/g polymer) | Reaction rate of amine component (%) |
|---|---|---|---|---|---|---|---|
| poly(PEG 500-MA)a sodium salt | #8 | M 3N 549 | 38 mL/g | 25° C. | 20 h | 2.79 | 99.5 |
| | #9 | M 3N 549 | 17.5 mL/g | 25° C. | 20 h | 2.87 | 96.4 |
| | #10 | M 3N 549 | 6 mL/g | 25° C. | 24 h | 3.26 | 80.9 |
| | #11 | M 3N 549 | 10 mL/g | 25° C. | 24 h | 3.01 | 90.9 |
| | #12 | M 3N 549 | 15 mL/g | 25° C. | 24 h | 2.91 | 94.6 |
| | #13 | M 3N 549 | 20 mL/g | 25° C. | 24 h | 3.11 | 86.9 |
| | #14 | M 3N 549 | 11 mL/g | 25° C. | 24 h | 3.26 | 81.1 |
| | #15 | M 3N 549 | 12 mL/g | 25° C. | 24 h | 3.02 | 90.3 |
| | #16 | M 3N 549 | 13 mL/g | 25° C. | 24 h | 2.98 | 92.1 |
| | #17 | M 3N 549 | 7 mL/g | 25° C. | 24 h | 3.94 | 53.8 |
| | #18 | M 3N 549 | 8 mL/g | 25° C. | 24 h | 3.08 | 88.1 |
| | #19 | M 3N 549 | 9 mL/g | 25° C. | 24 h | 3.29 | 80.0 |
| | #25 | M 3N 549 | 9 mL/g | 15° C. | 24 h | 3.05 | 89.4 |
| | #27 | M 3N 549 | 9 mL/g | 25° C. | 24 h | 3.40 | 75.6 |
| | #28 | M 3N 549 | 9 mL/g | 30° C. | 24 h | 3.02 | 90.6 |
| | #29 | M 3N 549 | 9 mL/g | 37° C. | 24 h | 3.16 | 85.0 |
| | #30 | M 3N 549 | 9 mL/g | 25° C. | 16 h | 3.00 | 91.3 |
| | #31 | M 3N 549 | 9 mL/g | 25° C. | 1 h | 2.95 | 93.2 |
| | #32 | M 3N 549 | 9 mL/g | 25° C. | 5 h | 3.25 | 81.3 |
| | #33 | M 3N 549 | 9 mL/g | 25° C. | 4 day | 3.92 | 54.8 |
| | #34 | M 3N 549 | 9 mL/g | 25° C. | 21 h | 3.13 | 86.2 |
| | #35 | M 3N 549 | 9 mL/g | 25° C. | 21 h | 2.95 | 93.3 |
| | #36 | M 3N 549 | 9 mL/g | 25° C. | 21 h | 2.98 | 91.9 |
| | #37 | M 3N 549 | 9 mL/g | 25° C. | 21 h | 3.15 | 85.5 |
| ammonium salt | #41 | M 3N 550 | ammonia gas | medium: DMF* | | 3.43 | 92.7 |

*DMF: N,N-dimethylformamide

8-19, 25 and 27-37 are the title polymers poly(PEG$_{500}$-MA)a (Compound Nos. 29-52). Each of these polymers is random and m = 6-16, $R^3$ = NH$_2$, composition ratio = 1:2.4 and average degree of polymerisation = 20-30.

Example 21

Preparation of the product of alcholysis reaction between ethanol and poly(PEG$_{500}$-MA) [poly (PEG$_{500}$-MA)ea-Na] wherein, m=6-16, R$_3$=OCH$_2$CH$_3$, comp. ratio=about 1:3, av. deg. pol.=20-30, hyd. ratio=about 3.1:6.9 (Compound No. 54)

Poly(PEG$_{500}$-MA) (AM-0510K, lot M3N550 manufactured using a procedure similar to that disclosed in Japanese Patent No. 2621308 and Japanese Patent Application Publication Nos. 2003-105040 and 2003-104003), a copolymer of polyoxyethylene allyl methyl diether (m=6-16, Alk=ethylene, R$_1$=hydrogen and R$_2$=methyl) and maleic anhydride in which the polyoxyethylene side chain has an average molecular weight of about 500, the average degree of polymerization of the main chain is in the range of from 20 to 30, the ratio of polyoxyethylene allyl methyl diether units to maleic anhydride units is about 1:3, the number average molecular weight (Mn) is 5891 and the molecular weight distribution index (Mn/Mw) is 1.28 (see Example 20 above), was used as the starting material. 1 ml of ethanol was added to 100 mg of said starting compound and the resulting reaction mixture was allowed to stand for 16 hours at 40° C. At the end of this time, 52 µl of a 2.5 N solution of sodium hydroxide in ethanol were added. The mixture thus obtained was concentrated at 35° C. by evaporation, and then dried under vacuum to obtain poly(PEG$_{500}$-MA)ea sodium salt (Compound No. 54) as an oily material. The hydrolysis ratio was calculated using the method described in Examples 3 and 6 above. Namely, by determining the carboxyl group contents of the poly(PEG$_{500}$-MA)ea sodium salt (Compound No. 54) and the corresponding poly(PEG$_{500}$-MA)h sodium salt, the ratio of maleic anhydride residues in the title compound subjected to alcoholysis to the total number of maleic anhydride residues in the starting material was calculated, and was determined to be 0.69. Thus, it can be seen that 69% of maleic anhydride residues in the starting material were subjected to alcoholysis, and the remaining 31% of maleic anhydride residues were subjected to hydrolysis.

Example 22

Preparation of Complexes of the Polymeric Modifier of Example 21 with OCIF

Polymer-OCIF complexes of the present invention were prepared as aqueous solutions using essentially the same preparative approach as in Example 14 above using an aqueous solution of Compound No. 54 prepared in Example 21 above [Concentration of Compound No. 54, 17.2 mg/ml; medium, PBS pH 7.4 (which is a solution obtained by mixing an aqueous solution containing 10 mM of disodium hydrogenphosphate and 150 mM of sodium chloride with an aqueous solution containing 10 mM of sodium dihydrogenphosphate and 150 mM of sodium chloride at a suitable ratio to give a buffer having a pH of 7.4)] and an aqueous solution of purified human mature OCIF (OCIF prepared as described in WO 96/26217 and EP 816380) (OCIF concentration, 4 mg/ml; medium, buffer containing 10 mM phosphate ion and 150 mM NaCl, pH 6.0). More specifically, 0.472 ml of a 17.2 mg/ml solution of Compound No. 54 were added to 1.328 ml of said 4 mg/ml OCIF solution to give a solution containing 4.5 mg/ml of Compound No. 54 and 3 mg/ml of OCIF. The resulting reaction mixture was allowed to stand for 3 days at 4, 10 or 25° C. to obtain aqueous solutions of the desired complexes of the present invention. The complex sizes were measured in Test Example 13 below.

Example 23

Preparation of the product of alcholysis reaction between ethanol and poly(PEG$_{500}$-MA) [poly (PEG$_{500}$-MA)ea] wherein, m=6-16, R$_3$=OCH$_2$CH$_3$, comp. ratio=about 1:3, av. deg. pol.=20-30 (Compound No. 55)

Poly(PEG$_{500}$-MA) (AM-0510K, lot M3N550 manufactured using a procedure similar to that disclosed in Japanese Patent No. 2621308 and Japanese Patent Application Publication Nos. 2003-105040 and 2003-104003), a random copolymer of polyoxyethylene allyl methyl diether (m=6-16, Alk=ethylene, R$_1$=hydrogen and R$_2$=methyl) and maleic anhydride in which the polyoxyethylene side chain has an average molecular weight of about 500, the average degree of polymerization of the main chain is in the range of from 20 to 30, the ratio of polyoxyethylene allyl methyl diether units to maleic anhydride units is about 1:3, the number average molecular weight (Mn) is 5891 and the molecular weight distribution index (Mn/Mw) is 1.28 (see Example 20 above), was used as the starting material. 0.5 ml of absolute ethanol were added to 50 mg of said starting compound and the resulting reaction mixture was allowed to stand at 37° C. for 24 hours. The title compound poly(PEG$_{500}$-MA)ea (Compound No. 55) was obtained as an ethanolic solution [poly (PEG$_{500}$-MA)ea conc.: 100 mg/ml].

Example 24

Preparation of Complexes of the Polymeric Modifier of Example 23 with OCIF

Polymer-OCIF complexes of the present invention were prepared as aqueous solutions using essentially the same preparative approach as in Example 14 above using the ethanolic solution of Compound No. 55 prepared in Example 23 above and an aqueous solution of purified human mature OCIF (OCIF prepared as described in WO 96/26217 and EP 816380) (OCIF concentration, 5 mg/ml; medium, buffer containing 10 mM phosphate ion and 150 mM NaCl, pH 6.0). More specifically, 37.5 µl of the ethanolic solution of Compound No. 55 were added to 0.5 ml of said 5 mg/ml OCIF solution and the resulting reaction mixture was allowed to stand for 3 days at 25° C. to give solutions of the desired complexes of the present invention. The complex sizes were measured in Test Example 13 below.

Comparative Example 1

Preparation of monomethoxypolyethylene glycol-methyl vinyl ether-maleic acid copolymer (PEG-PMVMA)

The graft copolymer monomethoxypolyethylene glycol-methyl vinyl ether-maleic acid copolymer (PEG-PMVMA)

was prepared according to the method disclosed in Example 2 of Japanese Patent Application (Kokai) No. Hei 11-302199.

Comparative Example 2

Preparation of a complex comprising monomethoxypolyethylene glycol-methyl vinyl ether-maleic acid copolymer (PEG-PMVMA) and OCIF protein Purified human OCIF (OCIF prepared as described in WO 96/26217 and EP 816380) modified with PEG-PMVA prepared as described in Comparative Example 1 above was prepared as a solution [medium: PBS (pH 6.0)] in essentially the same manner as in Example 9. More specifically, 1 ml of OCIF solution [OCIF concentration 2 mg/ml; medium PBS (pH 6.0)] and 1 ml of PEG-PMVA solution [PEG-PMVA concentration 2 or 20 mg/ml; medium PBS (pH 6.0)] were mixed and the mixture allowed to stand for 24 hours at 25° C. to give the title complex.

Comparative Example 3

Preparation of a complex comprising a polymeric modifier and OCIF protein using poly($PEG_{500}$-MA) as the polymeric modifier 2.2 µl of a dimethylsulfoxide solution containing poly($PEG_{500}$-MA) [AM-0530K, manufactured by NOF Corporation (hereinafter referred to as "poly($PEG_{500}$-MA)"] (polymer concentration: 35 to 350 mg/ml) were added to 28.4 µl of an aqueous solution of purified human OCIF (OCIF prepared as described in WO 96/26217 and EP 816380) (protein concentration: 3.5 mg/ml, medium: 0.5M $NaH_2PO_4$ aqueous solution, the pH of which was adjusted to 7.6 with 5M NaOH aqueous solution), and the solution thus obtained (OCIF concentration: 3.2 mg/ml, poly($PEG_{500}$-MA) concentration: 2.5 mg/ml or 6.3 mg/ml) was shaken at 25° C. for 40 hours. At the end of this time, the solution was diluted with PBS (pH 7.0) to obtain a solution of OCIF modified with the polymeric modifier having an OCIF concentration of 0.25 mg/ml. The solution thus prepared was stored at 4° C.

Test Example 1

Measurement of Carboxyl Group Content of the Polymers of Examples 10 to 13 by Conductometric Titration The carboxyl group content of each of the polymers [poly($PEG_{500}$-MA)a (Compound Nos. 9 and 10), poly($PEG_{500}$-MA)dma (Compound No. 11) and poly($PEG_{500}$-MA)h (Compound No. 12)] prepared in Examples 10 to 13 was determined by conductometric titration method as follows.

First, each of the polymers was purified using gel filtration as follows. For each polymer, 100 mg of the polymer were dissolved in 4 ml of 0.001 N sodium hydroxide solution. The solution was divided into four batches and each 1 ml batch was applied to a gel filtration column (PD-10, manufactured by Amersham-Pharmacia). The first 1 ml of eluant was discarded. 1.5 ml of 0.001 N sodium hydroxide solution were then applied to each column and a further 1.5 ml were eluted from the column and discarded. 2.5 ml of 0.001 N sodium hydroxide solution were then applied to each column and a further 2.5 ml were eluted from the column and it is this fraction that contained the purified compound. The purified fractions from the four columns were combined to give a purified solution of the title compounds. The yield after the purification step (determined spectophotometrically by measuring the absorbance of poly($PEG_{500}$-MA)h at 210 nm before and after purification) was determined to be 80% and the concentration in the purified solution was determined to be 8 mg/ml.

For each of the solutions of purified polymer, an aliquot (2.5 to 7.5 ml) was made up to 50 ml with distilled water or 0.001M aqueous sodium hydroxide solution, and then a 1M aqueous sodium hydroxide solution was added to the resulting solution to adjust the pH to 12. 0.1M hydrochloric acid was then added to the solution either in increments of 0.1 ml or continuously at a rate of 0.1 ml/min. In the former, the pH and conductivity were measured after each addition, and in the latter they were measured every 15 seconds. The carboxyl group content of the polymer was then calculated from the amount of 0.1M hydrochloric acid added in the conductivity buffering region (corresponding to a pH range of about 10 to 5.5). The results are shown in Table 5 below.

TABLE 5

| Example Number | Kind of polymer (and Cmpd. No.) | Carboxyl group content (mmol/g polymer) | Ammonolysis/ aminolysis rate (%) | Hydrolysis Ratio |
| --- | --- | --- | --- | --- |
| 10 | poly($PEG_{500}$-MA)a (9) | 2.10 | 69 | 3.1:6.9 |
| 11 | Poly($PEG_{500}$-MA)a (10) | 1.83 | 86 | 1.4:8.6 |
| 12 | Poly($PEG_{500}$-MA)dma (11) | 2.02 | 71 | 2.9:7.1 |
| 13 | Poly($PEG_{500}$-MA)h (12) | 3.21 | — | 10:0 |

For the polymers of Examples 10 to 12, the ratio of maleic anhydride residues in the starting material subjected to ammonolysis or aminolysis to maleic anhydride residues subjected to hydrolysis for each was determined by calculation as follows. As shown in Table 5 above, the carboxyl group content per 1 g of poly($PEG_{500}$-MA)h (Compound No. 12) is 3.21 mmols. From these values, the weight of poly($PEG_{500}$-MA) (that is, the weight of the copolymer before hydrolysis) per gram of functional group, and the weight of poly($PEG_{500}$-MA)a (Compound Nos. 9 and 10) obtained by adding ammonia to poly($PEG_{500}$-MA) per gram of functional group were determined. Specifically, the weight of poly($PEG_{500}$-MA) (that is, the weight of the copolymer before hydrolysis) per mol of maleic anhydride residue was obtained by subtracting the molecular weight of a molecule of water (18 g) from the weight of the fully hydrolysed copolymer, giving a figure of 605 g. The weight of poly($PEG_{500}$-MA)a (Compound Nos. 9 and 10) per mol of carboxyl group was obtained by adding the molecular weight of a molecule of ammonia (17 g) to the weight of poly($PEG_{500}$-MA), giving a figure of 622 g. From this value, the theoretical carboxyl group content per 1 g of poly($PEG_{500}$-MA)a (Compound Nos. 9 and 10) where all maleic anhydride residues have been subjected to ammonolysis (i.e. no hydrolysis) was determined by calculation (1 g/622), and was found to be 1.61 mmols. In the same manner, the weight of poly(PEG$_{500}$-MA)dma (Compound No. 11) obtained by adding dimethylamine to poly(PEG$_{500}$-MA) per mol of carboxyl group was determined by adding the molecular weight of a molecule of dimethylamine to the weight of poly(PEG$_{500}$-MA), giving a figure of 650 g. From this value, the theoretical carboxyl group content per 1 g of poly (PEG$_{500}$-MA)dma where all maleic anhydride residues have been subjected to aminolysis by dimethylamine was determined by calculation, and was found to be 1.54 mmols.

For each of the polymers of Examples 10 to 12, the hydrolysis ratio (the percentage of the starting material subjected to hydrolysis compared to ammonolysis or aminolysis) and the ammonolysis or aminolysis reaction rate (%) was determined from the carboxyl group content per 1 g of poly (PEG$_{500}$-MA)h (Compound No. 11) where all maleic anhydride residues have been subjected to hydrolysis, the theoretical carboxyl group content per 1 g of poly(PEG$_{500}$-MA)a (Compound Nos. 9 and 10) where all maleic anhydride residues have been subjected to ammonolysis, the theoretical carboxyl group content per 1 g of poly(PEG$_{500}$-MA)dma (Compound No. 11) where all maleic anhydride residues have been subjected to aminolysis by dimethylamine, and the actual measured carboxyl group contents per 1 g of each for each of the polymers of Examples 10 to 12 measured by conductometric titration above. The results are as shown in Table 5 above.

Test Example 2

Evaluation of Retention of OCIF-Modifier Complexes in the Blood Using Rat

Each of the samples prepared as described in Example 9, Comparative Example 2 and non-modified purified human OCIF (OCIF prepared as described in WO 96/26217 and EP 816380) was appropriately diluted with PBS (pH 6.0) so that the OCIF concentration was 0.25 mg/ml. Each of the diluted samples thus obtained was administered to the tail of a five-week old Wistar female rat (having a body weight of about 100 g and which had abstained from food for one day) via a vein so that the OCIF dose was 0.5 mg/kg (2 ml/kg by volume). 6 hours after administration, 200 μl of blood were taken from the heart of the rat, and then the OCIF concentration in blood serum was measured by an ELISA method, the conditions used being as described in Test Example 3 below.

The OCIF concentration in the blood serum measured after the administration of each sample is shown in Table 6 below.

TABLE 6

OCIF concentration in blood serum after intravenous administration of each OCIF sample

| Modifier (and Compound No.) | Modifier/ OCIF (weight ratio) | OCIF concentration in blood serum 6 hours after administration (ng/ml) | Conditions at mixing* |
|---|---|---|---|
| Non-modified OCIF | — | 25 ± 19 | — |
| PEG-PMVMA | 1 | 101 ± 26 | — |
|  | 10 | 361 ± 33 | — |
| poly(PEG$_{1500}$-MA)h (2) | 10 | 502 ± 70 | — |
| poly(PEG$_{1500}$-MA)a (7) | 10 | 1029 ± 30 | — |
| poly(PEG$_{1500}$-MA)dma (8) | 1 | 2145 ± 721 | — |
| poly(PEG$_{500}$-MA)h (1) | 10 | 750 ± 80 | — |
|  | 2.5 | 434 ± 92 | — |
| poly(PEG$_{500}$-MA)a (3) | 10 | 3416 ± 440 | — |
|  | 10 | 2445 ± 195 | 37° C. |
|  | 2.5 | 3428 ± 27 | — |
|  | 2.5 | 484 ± 92 | 1 hour |
|  | 1 | 3004 ± 158 | — |
|  | 1 | 2275 ± 130 | pH 7.4 |
|  | 1 | 3786 ± 461 | 40 hours |
|  | 1 | 777 ± 153 | 4° C. |
|  | 0.5 | 2951 ± 512 | — |
| poly(PEG$_{500}$-MA)dma (4) | 1 | 1014 ± 331 | — |

*Basic conditions at mixing were OCIF concentration of 1 mg/ml, pH 6.0, 16 hours, and 25° C. Only the conditions different from these are given in Table 6.

It will be readily appreciated from Table 6 above that each of the complexes of polymeric modifier and protein of the present invention significantly improved the retention of the protein in the blood when compared to the retention of protein when administered alone. It can also be seen by comparison of the prior art complex of PEG-PMVMA and protein (disclosed in Japanese Patent Laid-open No. Hei 11-302199 and prepared in Comparative Example 2 above) and the complexes of the present invention having the same weight ratio between the modifier and protein (1 or 10), that the complexes of modifier and protein of the present invention gave considerably improved retention of the protein in the blood compared to the prior art complex of PEG-PMVMA and protein.

Test Example 3

Evaluation of Detection Rate of OCIF by ELISA

One of the problems encountered with prior art protein modifiers is that binding of the modifiers to the protein causes modification of the protein structure and/or shielding of the protein due to the formation of bulky complexes. In order to test the OCIF-modifier complexes of the present invention, the detection rate of each of the complexes prepared as described in Example 9 and Comparative Example 2 was determined on the basis of non-modified purified human OCIF (OCIF prepared as described in WO 96/26217 and EP 816380) by ELISA. ELISA was carried out as follows.

Anti-human OCIF monoclonal antibody OI-19 (prepared according to the method disclosed in EP0974671) was dissolved in a 0.1M sodium acid carbonate solution (pH 9.6) to obtain a solution having an OI-19 concentration of 10 μg/ml. 100 μl of the OI-19 solution thus prepared were placed in each well of a 96-well immunoplate (manufactured by Nunc), and the plates were allowed to stand at 4° C. overnight. At the end of this time, 50% Block Ace (purchased from Snow Brand Milk Products Co., Ltd.) was added to each well to block, and then the plates were washed three times with PBS (washing buffer) containing 0.1% Tween 20. Purified human OCIF (OCIF prepared as described in WO 96/26217 and EP 816380) was dissolved in primary reaction buffer (that is, 0.2M tris hydrochloric acid buffer solution (pH 7.4) containing 40% Block Ace, 0.1% Tween 20 and 10 μg/ml of Mouse IgG) to prepare standard solutions with various OCIF concentrations. 100 μl of each of the thus prepared solutions with various OCIF concentrations were added to each well, the plates were shaken at room temperature for 2 hours and then each well was washed six times with the washing buffer. POD-OI-4 (that is, an antibody labeled with peroxidase and recognizing OCIF, prepared as described in EP 0974671) was then diluted 10,000-fold with secondary reaction buffer (that is, 0.1M tris hydrochloric acid buffer solution (pH 7.4) containing 25% Block Ace, 0.1% Tween 20 and 10 μg/ml of Mouse IgG), 100 μl of the resulting solution were added to each well, the plates were shaken at room temperature for 2 hours and then each well was washed six times. Once this had been done, 100 μl of a substrate solution (TMB soluble reagent, available from Scytek) were added to each well, and the plates were shaken at room temperature for 10 to 15 minutes. Thereafter, 100 μl of a reaction stopping reagent (TMB stop buffer, available from Scytek) were added to each well and the plates were gently shaken. At the end of this time, the absorbance at a wavelength of 450 nm for each well was measured by a microplate reader (MEML 001, manufactured by Molecular Device corporation). From these results a calibration curve was produced of OCIF concentration against absorbance. Having produced this calibration curve, the procedure was repeated for each of the tested complexes of OCIF and modifier, 100 μl of each of the solutions containing a test complex being added to each well, reaction with POD-OI-4 being performed in the same manner as above and then absorbance at a wavelength of 450 nm for each well being measured by a microplate reader. Comparison of the absorbances obtained with the calibration curve enabled the OCIF concentration detectable by ELISA in each of the complexes to be measured.

For each of the samples, the rate of failure to detect OCIF by ELISA was calculated and the results are as shown in Table 7 below. The rate of failure to detect OCIF by ELISA is defined by the following equation:

$$\text{Rate} = [1 - (OCIF \text{ concentration measured by } ELISA)/(OCIF \text{ concentration measured by the Lowry method})] \times 100$$

In the above equation, the Lowry method to measure OCIF concentration in the complexes is determined as described in Japanese Patent Application No. 2002-190407. This gives a measure of the total OCIF concentration in the complexes. The rate of failure to detect OCIF by ELISA in the complex is a measure of the change of conformation of the OCIF caused by complexing with the modifier. A low rate of failure is evidence that the OCIF in the complex can be readily bound by both 01-19 and 01-4 anti-OCIF antibodies, thus showing little or no modification of the OCIF structure in the complex.

TABLE 7

Rate of failure to detect OCIF sample by ELISA

| Modifier (and Compound No.) | Modifier/OCIF (weight ratio) | Rate of failure to detect OCIF by ELISA (%) (on the basis of non-modified OCIF) |
|---|---|---|
| OCIF | — | — |
| PEG-PMVMA | 1 | 25 |
|  | 10 | 39 |
| poly(PEG$_{1500}$-MA)h (2) | 10 | 13 |
| poly(PEG$_{1500}$-MA)a (7) | 10 | 15 |
| poly(PEG$_{1500}$-MA)dma (8) | 10 | 0 |
| poly(PEG$_{500}$-MA)h (1) | 10 | 17 |

TABLE 7-continued

Rate of failure to detect OCIF sample by ELISA

| Modifier (and Compound No.) | Modifier/OCIF (weight ratio) | Rate of failure to detect OCIF by ELISA (%) (on the basis of non-modified OCIF) |
|---|---|---|
| poly(PEG$_{500}$-MA)a (3) | 10 | 0 |
|  | 2.5 | 0 |
| Poly(PEG$_{500}$-MA)dma (4) | 1 | 12 |

From the results shown in Table 7 above it can be seen that, for the complexes of polymeric modifier and protein of the present invention, the rate of failure to detect OCIF by ELISA as a result of modification of the protein structure was significantly decreased compared to the high rate that was obtained in the case of the prior art complex of PEG-PMVMA and protein prepared in Test Example 2 above.

From the results of Test Examples 2 and 3, it was thus confirmed that the decrease in protein detection sensitivity caused by excessive modification of the protein for the complexes of polymeric modifier and protein of the present invention is very low and, furthermore, the retention in blood of the protein in said complexes is significantly better than achieved with prior art complexes.

Test Example 4

Measurement of OCIF Concentration in Blood

Each of the samples prepared as described in Example 9 and purified human OCIF (OCIF prepared as described in WO 96/26217 and EP 816380) is appropriately diluted with PBS (having a pH of 6.0 to 7.4) so that the OCIF concentration is 0.1 to 1 mg/ml. Each of the thus prepared diluted samples is then administered to a six- or seven-year-old female cynomolgus monkey (having a body weight of 2 to 4 kg and which had abstained from food for one day) via the saphenous vein or subcutaneously dorsally to administer an OCIF dose of 0.1 to 1 mg/kg (1 ml/kg by volume). At a predetermined period of time in the range of from five minutes to one month after administration, 500 μl of blood is taken from the femoral blood vessel thereof, and the OCIF concentration in the blood serum is measured by the ELISA method described in Test Example 3 above.

Test Example 5

Measurement of Bone Density

Each of the samples prepared as described in Example 9 and purified human OCIF (OCIF prepared as described in WO 96/26217 and EP 816380) is appropriately diluted with PBS (having a pH of 6.0 to 7.4) so that the OCIF concentration is in the range of from 0.7 to 3.5 mg/ml. An adjuvant is then prepared using killed cells of *Mycobacterium butyricum* and liquid paraffin, and is injected in the skin of the root of the tail of a 5- to 10-week-old female Lewis rat to give rise to arthritis in said rat. Two weeks after injection of the adjuvant, each of the prepared samples is administered to the rat via the tail vein or subcutaneously dorsally so that the OCIF dose is 1.4 to 7 mg/kg (2 ml/kg by volume). Three weeks after injection of the adjuvant, the rat was dissected to extract the right-and-left thighbone, and the bone density thereof was measured.

Test Example 6

Evaluation of Molecular Size by SDS Polyacrylamide Gel Electrophoresis Under Non-Reducing Conditions The molecular size of each of the complexes of polymeric modifier and OCIF prepared as described in Example 14 and Comparative Example 3 and purified human OCIF (OCIF prepared as described in WO 96/26217 and EP 816380) was evaluated by SDS-PAGE under non-reducing conditions as follows.

5 µl of NuPAGE (trade mark) LDS Sample Buffer (4×) (obtained from Invitrogen Life Technology) and 5 µl of purified water were added to 10 µl of each of the tested samples [which were diluted if necessary with phosphate buffer saline (PBS (pH 7.0), which is a buffer solution obtained by mixing a solution containing 10 mM disodium hydrogenphosphate and 150 mM sodium chloride and a solution containing 10 mM sodium dihydrogenphosphate and 150 mM sodium chloride at an appropriate volume ratio to give a buffer pH of 7.0) so that the protein concentration was 250 µg/ml] and each of the resulting solutions was heated at 95° C. for 7 minutes. At the end of this time, the full amount of the reaction mixture was added to a SDS-polyacrylamide electrophoresis gel (3 to 8% Tris-Acetate gel having a thickness of 1 mm and manufactured by NOVEX), and a voltage of 150 V was applied to the gel using a power supply device (PhoreStar Pro, manufactured by Anatech). After completion of electrophoresis, protein on the gel was stained with Coomassie blue according to a method well known to those skilled in the art.

Figure 1:
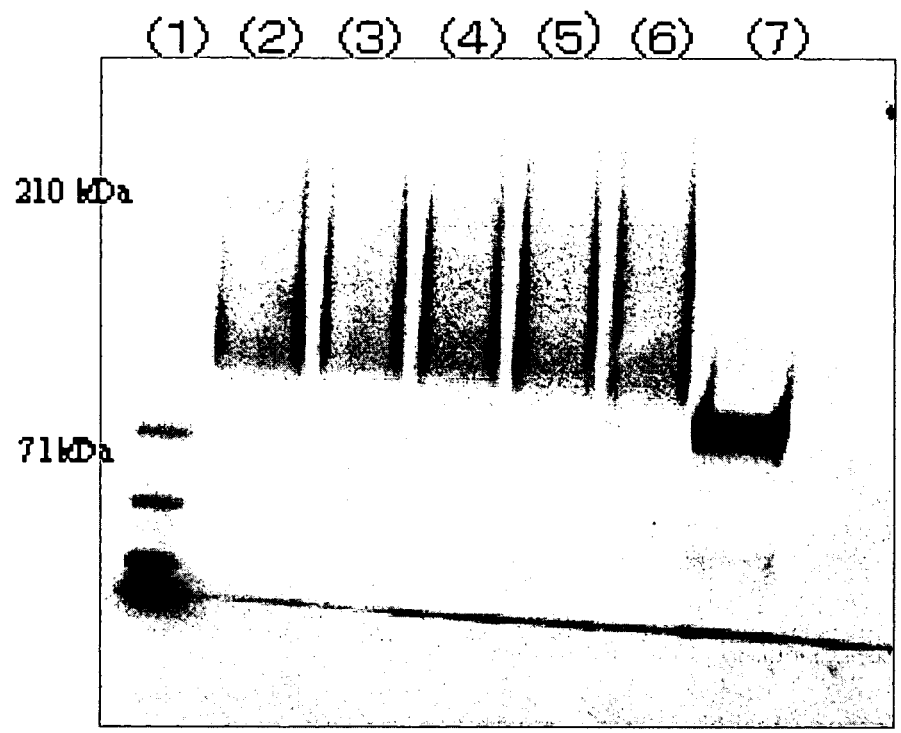
FIG. 1 shows results of SDS polyacrylamide gel electrophoresis on complexes of the present invention of poly(PEG$_{500}$-MA)a-OCIF under non-reducing conditions as performed in Test Example 6 below.

As can be seen from in FIGS. 1 and 2, OCIF modified with the polymeric modifier of the present invention was stably detected as a substance having a molecular weight higher than that of non-modified OCIF (120 kD) at all mixing ratios (a primary band of 130 to 150 kD and a secondary band of 180 to 200 kD were detected on the basis of the molecular weight markers), and furthermore no complex having a molecular weight exceeding 210 kD was detected. Similar results (not shown) were also obtained for other polymeric modifiers of the present invention which were the products of aminolysis and alcoholysis. On the other hand, as can be seen in FIG. 3, in the case of OCIF modified with the conventional polymeric modifier poly($PEG_{500}$-MA) prepared in Comparative Example 3, the amount of bulky complex obtained is markedly increased as the ratio of the modifier is increased.

This result shows that by using the polymeric modifier of the present invention, it is possible to markedly suppress the formation of bulky complexes which are not pharmaceutically preferable and to prepare a complex of polymeric modifier and protein which has stable properties irrespective of the mixing ratio, when compared with the structurally quite similar polymeric modifier poly($PEG_{500}$-MA) of the prior art.

Test Example 7

Evaluation of Covalent Bond Formation Activity of poly($PEG_{500}$-MA)a

The reactivity of each of the polymeric modifiers poly($PEG_{500}$-MA)a (Compound No. 9) and poly($PEG_{500}$-MA)h (Compound No. 12) to tetramethylrhodamine cadaverine, which is a fluorescent substance having an anino group and a molecular weight of 514.62 (available from Molecular Probes, Inc.) (hereinafter referred to as "Rho-$NH_2$") was determined, and the covalent bond formation activity of the modifiers was evaluated by comparing the reactivity of the two polymeric modifiers as follows.

3.8 µl of solutions of each of poly($PEG_{500}$-MA)h (Compound No. 12) (prepared as described in Example 13 above) and poly($PEG_{500}$-MA)a (Compound No. 9) [polymer concentration: 21 mg/ml, medium: PBS (pH was adjusted with 1M NaOH to 9.5)] (prepared as described in Example 10 above) were added to 18.9 µl of PBS (pH 6.0) containing 1.08 mg/ml Rho-$NH_2$. The solutions thus obtained were allowed to stand at 25° C. for 3 days. At the end of this time, the reaction mixtures were fractionated by gel filtration chromatography (column: PD-10 manufactured by Amersham Biotech, mobile phase: purified water) as follows. 0.5 ml of the reaction mixture were applied to the gel filtration column and 0.5 ml run off the column and discarded. 2 ml of distilled water were added to the column and a further 2 ml were eluted and discarded. A further 2 ml of distilled water were added to the column and a further 2 ml were eluted and this fraction contained the polymer fraction. Rho-$NH_2$ contained in the polymer fractions was quantified by fluorescence spectrometry (excitation wavelength: 544 nm, fluorescent wavelength: 571 nm, medium: purified water adjusted to pH 3), to calculate the ratio of the amount of Rho-$NH_2$ contained in each complex of polymer and Rho-$NH_2$ with respect to the total amount of Rho-$NH_2$ in the reaction mixture, i.e. the binding ratio of Rho-$NH_2$ to the polymer.

The results were as shown in Table 8 below.

TABLE 8

Reactivity of polymeric modifier

|  | Binding ratio of Rho-$NH_2$ to polymer* (%) |
| --- | --- |
| Rho-$NH_2$ + poly($PEG_{500}$-MA)a | 11.5, 12.6 |
| Rho-$NH_2$ + poly($PEG_{500}$-MA)h | 0.8, 1.6 |
| Rho-$NH_2$ alone | 0, 0 |

*This test was carried out twice.

It can be readily seen from Table 8 above that for the reaction mixture of the polymeric modifier poly($PEG_{500}$-MA)a (Compound No. 9) with Rho-$NH_2$, there is quite a high level of Rho-$NH_2$ detected in the polymer fraction. This is in contrast with the reaction mixture of the polymeric modifier poly($PEG_{500}$-MA)h (Compound No. 12) with Rho-$NH_2$, where there is only a low level of Rho-$NH_2$ detected in the polymer fraction. When Rho-$NH_2$ alone was applied to the column, no Rho-$NH_2$ was eluted in the "polymer fraction". These results indicate that the polymeric modifier poly($PEG_{500}$-MA)a (Compound No. 9) of the present invention binds strongly to the amino group of the Rho-$NH_2$. On the other hand, the binding ratio of the polymeric modifier poly($PEG_{500}$-MA)h (Compound No. 12) of the present invention is low suggesting that this polymeric modifier is not strongly bound to the amino group of the Rho-$NH_2$.

Test Example 8

Evaluation of Detection Rate of OCIF by ELISA

The detection rate of each of the complexes of OCIF and polymeric modifier prepared as described in Example 14 and Comparative Example 3 above was determined on the basis of non-modified purified human OCIF (OCIF prepared as described in WO 96/26217 and EP 816380) by ELISA. ELISA was carried out as follows.

Anti-human OCIF monoclonal antibody 01-19 (prepared according to the method disclosed in EP0974671) was dissolved in a 0.1M sodium acid carbonate solution (pH 9.6) to obtain a solution having an OI-19 concentration of 10 µg/ml. 100 µl of the OI-19 solution thus prepared were placed in each well of a 96-well immunoplate (manufactured by Nunc), and the plates were allowed to stand at 4° C. overnight. At the end of this time, 50% Block Ace (purchased from Snow Brand Milk Products Co., Ltd.) was added to each well to block, and then the plates were washed three times with PBS (washing buffer) containing 0.1% Tween 20. Purified human OCIF (OCIF prepared as described in WO 96/26217 and EP 816380) was dissolved in primary reaction buffer (that is, 0.2M tris hydrochloric acid buffer solution (pH 7.4) containing 40% Block Ace, 0.1% Tween 20 and 10 µg/ml of Mouse IgG) to prepare standard solutions with various OCIF concentrations. 100 µl of each of the thus prepared solutions with various OCIF concentrations were added to each well, the plates were shaken at room temperature for 2 hours and then each well was washed six times with the washing buffer. POD-OI-4 (that is, an antibody labeled with peroxidase and recognizing OCIF, prepared as described in EP0974671) was then diluted 10,000-fold with secondary reaction buffer (that is, 0.1M tris hydrochloric acid buffer solution (pH 7.4) containing 25% Block Ace, 0.1% Tween 20 and 10 µg/ml of Mouse IgG), 100 µl of the resulting solution were added to each well, the plates were shaken at room temperature for 2 hours and then each well was washed six times. Once this had been done, 100 µl of a substrate solution (TMB soluble reagent, available from Scytek) were added to each well, and the plates were shaken at room temperature for 10 to 15 minutes. Thereafter, 100 µl of a reaction stopping reagent (TMB stop buffer, available from Scytek) were added to each well and the plates were gently shaken. At the end of this time, the absorbance at a wavelength of 450 nm for each well was measured by a microplate reader (MEML 001, manufactured by Molecular Device corporation). The OCIF concentration of each standard OCIF sample was calculated based on the calibration curve produced using OCIF solutions having a known concentration.

For each of the samples of the tested complex, the absorbances were measured, the OCIF concentrations calculated from the standard curve and the rate of failure to detect OCIF by ELISA was calculated as explained in Test Example 3 above. The results obtained are as shown in Table 9 below.

TABLE 9

Rate of failure to detect OCIF sample by ELISA

| Modifier (and Compound No.) | Modifier/OCIF (weight ratio) | Rate of failure to detect OCIF by ELISA (%) (on the basis of non-modified OCIF) |
|---|---|---|
| OCIF alone | — | — |
| poly(PEG$_{500}$-MA)h (12) | 1 | 8 |
| poly(PEG$_{500}$-MA)a-Na salt (9) | 1 | 0 |
| | 0.75 | 0 |
| | 0.5 | 0 |
| | 0.25 | 0 |
| poly(PEG$_{500}$-MA) | 7.8 | 98 |
| | 1.9 | 89 |
| | 0.78 | 60 |

It can be readily seen from Table 9 above that, for each of the complexes of polymeric modifier and protein of the present invention prepared in Example 14, the rate of failure to detect OCIF by ELISA caused by modification of protein was significantly decreased compared to the prior art complex of polymer and protein prepared in Comparative Example 3, for which the rate of failure to detect OCIF by ELISA was very high.

From these results, it is clear that the complexes of polymeric modifier and protein of the present invention give only a very small decrease in the detection sensitivity by ELISA that can be caused by excess modification of protein and/or formation of a bulky complex.

Test Example 9

Evaluation of Retention in Blood Using Rat

Each of the samples prepared in Example 14 and non-modified purified human OCIF (OCIF prepared as described in WO 96/26217 and EP 816380) was appropriately diluted with PBS (pH 7.0) so that the OCIF concentration was 0.25 or 0.025 mg/ml. Each of the diluted samples thus obtained was administered to a five-week-old Wistar female rat (having a body weight of about 100 g that had abstained from food for one day) via a femoral vein so that the OCIF dose was 0.5 or 0.05 mg/kg (2 ml/kg by volume). 6 hours after administration, 200 µl of blood were taken from the jugular vein of the rat, and then the OCIF concentration in the blood serum was measured by the ELISA method described above.

The OCIF concentration in blood serum measured after the administration of each sample is shown in Table 10 below.

TABLE 10

OCIF concentration in blood serum after intravenous administration of each OCIF sample

| Modifier (and Compound No.) | Modifier/ OCIF (weight ratio) | Dosage (mg/kg) | OCIF concentration in blood serum 6 hours after administration (ng/ml) |
|---|---|---|---|
| OCIF alone | — | 0.5 | 18 |
| poly(PEG$_{500}$-MA)h (12) | 1 | 0.05 | 127 |
| poly(PEG$_{500}$-MA)a-Na salt (9) | 1 | 0.05 | 603 |
| | 1 | 0.5 | 5,549 |
| | 0.75 | 0.5 | 4,770 |
| | 0.5 | 0.5 | 4,292 |
| | 0.25 | 0.5 | 3,020 |

As is apparent from Table 10 above, the complex of polymeric modifier and protein of the present invention significantly improved the retention of said protein in the blood when compared to when the protein alone was administered.

From the results above, it is clear that the complex of polymeric modifier and protein of the present invention can be stably produced under wide-ranging conditions and that said complex significantly improves the retention in blood of the protein of the complex after administration. The complex is therefore likely to be extremely useful in pharmaceutical and biochemical fields.

Test Example 10

Evaluation of Retention in Blood Using Rat

Each of the samples prepared in Example 17 and Example 19 was evaluated in the same manner as in Test Example 9. The OCIF concentration in blood serum measured after administration of each sample is shown in Table 11 below.

TABLE 11

OCIF concentration in blood serum after intravenous administration of each OCIF sample

| Example Number | Modifier (and Compound No.) | Fraction | Modifier/ OCIF (weight ratio) | Dosage (mg/kg) | OCIF concentration in blood serum after 6 hours from administration (ng/ml) |
|---|---|---|---|---|---|
| 17 | poly(PEG$_{500}$-MA)$_a$-Na | | | | |
| | 14 | SRF55-60 | 1 | 0.05 | 437 |
| | 14 | | 2.5 | 0.05 | 460 |
| | 15 | SRF60-65 | 1 | 0.05 | 478 |
| | 19 | SDF60-70 | 1 | 0.5 | 4,255 |
| 17 | poly(PEG$_{1500}$-MA)$_a$ | | | | |
| | 21 | SRF55-60 | 1 | 0.5 | 256 |
| | 21 | | 2.5 | 0.05 | 334 |
| 19 | poly(PEG$_{500}$-MA)$_a$ | | | | |
| | 27 | Non-fractionated | 1 | 0.5 | 6,138 |
| | 28 | Non-fractionated | 1 | 0.5 | 6,713 |

It can be readily seen from Table 11 above that all of the tested polymeric modifiers of the present invention having various molecular sizes significantly increased the retention in the blood of the protein compared to when the protein alone was administered.

Test Example 11

Evaluation of Molecular Size by Size Exclusion Chromatography

The molecular size of each of the complexes of polymeric modifier and OCIF prepared in Example 9, Example 14, Example 17 and Example 19 was evaluated by size exclusion chromatography. Test conditions are as shown in Table 12 below.

TABLE 12

Conditions for size exclusion chromatography

Chromatography apparatus: Explorer 10S (Amersham Biotech)
Column: Superdex 200 HR10/30 (Amersham Biotech)
Mobile phase: phosphate buffer saline
(8 mM Na$_2$HPO$_4$, 15 mM KH$_2$PO$_4$, 145 mM NaCl, 0.5 g/L NaN$_3$)
Analytical temperature: 4° C.
Wavelength for detection: 280 nm
Flow rate of mobile phase: 0.6 mL/min The retention time of the following standard proteins under the above-mentioned conditions are as shown in Table 13 below.

TABLE 13

The retention time of each standard protein

| Kind of protein | Molecular weight (kD) | Stokes radius (nm) | Retention time (min) |
|---|---|---|---|
| Ferritin | 440 | 6.10 | 18.41 |
| Aldose | 158 | 4.81 | 22.48 |
| Ovalbumin | 43 | 3.05 | 25.19 |
| Ribonuclease | 13.7 | 1.64 | 29.56 |

From the results of the size exclusion chromatography, the Stokes radius of non-complexed OCIF was determined to be 5.63 nm, and that of each polymeric modifier—OCIF complex of the invention was as determined as follows:

Complexes Prepared in Example 9:

poly(PEG$_{500}$-MA)h (Compound No. 1)-OCIF complexes (Stokes radii ranging from 6.13 nm to 7.32% nm)

poly(PEG$_{500}$-MA)a (Compound No. 3)-OCIF complexes (from 6.12 nm to 6.54 nm), poly(PEG$_{500}$-MA)dma (Compound No. 4)-OCIF complex (6.39 nm), poly(PEG$_{500}$-MA)ipa (Compound No. 5)-OCIF complex (6.26 nm), poly(PEG$_{500}$-MA)ea (Compound No. 6)-OCIF complex (6.44 nm), poly(PEG$_{1500}$-MA)h (Compound No. 2)-OCIF complex (from 6.44 nm to 6.71 nm), poly(PEG$_{500}$-MA)a (Compound No. 7)-OCIF complex (from 6.40 nm to 6.47 nm), poly(PEG$_{1500}$-MA)dma (Compound No. 8)-OCIF complex (6.55 nm).

From these results it is apparent that each of the complexes of the invention had a Stokes radius that was larger by about 1 nm than that of non-complexed OCIF in phosphate buffer saline used as the mobile phase. Further, for each of the samples, a peak derived from non-modified OCIF was not detected, showing the stability of the complexes.

The Stokes radii of the other complexes were determined under conditions similar to those described above. The results were as follows:

Complexes Prepared in Example 14:

Complexes prepared under the conditions OCIF conc., 5 mg/mL; polymeric modifier conc., ranging from 1.25 mg/ml to 5 mg/ml; pH 7.4; 25° C.; 36 h; medium, phosphate buffered saline (phosphate conc., 10 mM; NaCl conc., 150 mM), were found to have Stokes radii ranging from 6.2 nm to 6.5 nm. Further, for each of the samples, a peak derived from non-modified OCIF was not detected, showing the stability of the complexes.

Complexes Prepared in Example 17:

Complexes prepared with incubation conditions OCIF conc., 0.5 mg/ml; polymeric modifier conc., 0.5 mg/ml; pH 6.0; 25° C.; 168 h; medium, phosphate buffered saline (phosphate conc., 10 mM; NaCl conc., 150 mM), were found to have Stokes radii ranging from 6.1 nm to 6.7 nm. Further, for each of the samples, a peak derived from non-modified OCIF was not detected, showing the stability of the complexes.

Complexes Prepared in Example 19:

Complexes with incubation conditions OCIF conc., 5 mg/ml; polymeric modifier conc., 5 mg/ml; pH 5.5; 25° C.; 168 h; medium, phosphate buffered saline (phosphate conc., 10 mM; NaCl conc., 150 mM), were found to have Stokes radii ranging from 6.3 nm to 6.8 nm. Further, for each of the samples, a peak derived from non-modified OCIF was not detected, showing the stability of the complexes.

The increase in the Stokes radii of the polymeric modifier —OCIF complexes of the present invention when compared to the non-complexed OCIF can be attributed to the modification of OCIF with the polymeric modifiers of present invention.

Test Example 12

Evaluation of Retention in Blood Using Rat and Evaluation of Detection Rate of OCIF by ELISA The retention in blood and the detection rate of OCIF by ELISA were tested for the complex prepared in Example 22 (complex of Compound No. 54 and OCIF) (incubation temperature: 25° C.) in the same manner as described in Test Examples 2 and 3 above. The OCIF-equivalent dose was set to 0.1 mg/kg. The serum concentration of OCIF was found to be 189 ng/ml 6 hours after iv injection of the complex. Thus, it was confirmed that the complexes prepared with poly ($PEG_{500}$-MA)ea sodium salt (Compound No. 54) in Example 22 above showed an excellent level of retention in the blood. Furthermore, the decrease in the OCIF detection sensitivity by ELISA due to excessive modification of the protein by the modifier in the complex was found to be very low.

Test Example 13

Evaluation of Complex Size

The molecular size of the complexes prepared in Examples 22 (complex of Compound No. 54 and OCIF) and 24 (complex of Compound No. 55 and OCIF) were evaluated by gel filtration chromatography as described in Test Example 11 above. It was found that the molecular size of these complexes showed a high level of uniformity. For the complexes of Compound No. 54 and OCIF complexed at 4° C., 10° C. and 25° C. the Stokes radii were found to be 6.0 nm, 6.0 nm and 6.0 nm. For the complexes of Compound No. 55 and OCIF, the Stokes radii were 6.4 nm. Each of the complexes prepared in Example 22 and 24 thus had a larger Stokes radius than non-modified purified human OCIF (Stokes radius: 5.63 nm).

Preparation Example

A solution containing the complex obtained under sterile conditions in the same manner as described in Example 14 above is freeze-dried to obtain a freeze-dried preparation.

The invention claimed is:

1. A copolymer or a pharmacologically acceptable salt thereof, with an average degree of polymerization in the range of from 5 to 200, consisting of, as constitutional units,
(a) one or more structural units which may be the same or different from each other and which are represented by the formula (I) below:

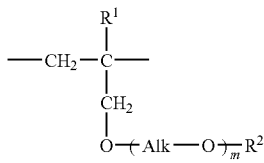

(I)

wherein:
m is an integer of from 3 to 100,
Alk represents an alkylene group having from 1 to 6 carbon atoms, and
$R^1$ and $R^2$ are the same or different and each represents a hydrogen atom or an alkyl group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below, and
(b) one or more structural units which may be the same or different from each other and which are represented by the formula (II):

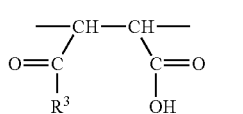

(II)

wherein:
$R^3$ is selected from the group consisting of
an alkoxy group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below,
an aryloxy group having from 6 to 14 carbon atoms that may optionally be substituted with from 1 to 5 substituents selected from Substituents A defined below, and
a group represented by the formula —$NR^4R^5$, wherein $R^4$ and $R^5$ are the same or different from each other and each represents a hydrogen atom or an alkyl group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below, and
a hydroxyl group present in a ratio of 5:5 to 0:10, wherein the ratio represents said hydroxyl group:one of said other groups listed above as a selection for $R^3$ in the structural unit represented by formula (II) in said copolymer molecule, and
Substituents A are selected from alkyl groups having from 1 to 6 carbon atoms, alkoxy groups having from 1 to 6 carbon atoms, halogen atoms, hydroxy groups, nitro groups and carboxy group.

2. A copolymer or a pharmacologically acceptable salt thereof according to claim 1, wherein the structural units represented by the formula (I) and the structural units represented by the formula (II) are arranged in an alternating head-to-head sequence, an alternating head-to-tail sequence or an alternating mixed sequence of head-to-head and head-to-tail.

3. A copolymer or a pharmacologically acceptable salt thereof according to claim 1, wherein the structural units represented by the formula (I) and the structural units represented by the formula (II) are arranged in a random sequence.

4. A copolymer or a pharmacologically acceptable salt thereof according to claim 1, wherein $R^3$ is selected from the group consisting of an alkoxy group having from 1 to 6 carbon atoms and a group represented by the formula —$NR^4R^5$, wherein $R^4$ and $R^5$ are the same or different and each represents a hydrogen atom or an alkyl group having from 1 to 6 carbon atoms.

5. A copolymer or a pharmacologically acceptable salt thereof according to claim 1, comprising at least one structural unit represented by the formula (II) in which $R^3$ is an alkoxy group having from 1 to 6 carbon atoms and optionally at least one structural unit represented by the formula (II) in which $R^3$ is a hydroxyl group, wherein the ratio between the structural units represented by the formula (II) in which $R^3$ is a hydroxy group and the structural units represented by the formula (II) in which $R^3$ is an alkoxy group having from 1 to 6 carbon atoms is in the range of from 4:6 to 0:10.

6. A copolymer or a pharmacologically acceptable salt thereof according to claim 1, wherein $R^3$ is a group represented by the formula —$NR^4R^5$, wherein $R^4$ and $R^5$ are the same or different and each represents a hydrogen atom or an alkyl group having from 1 to 6 carbon atoms.

7. A copolymer or a pharmacologically acceptable salt thereof according to claim 1, wherein the Stokes radius thereof is 9.3 nm or less.

8. A copolymer or a pharmacologically acceptable salt thereof according to claim 1 wherein:
m is an integer of from 3 to 100,
Alk represents an alkylene group having from 1 to 6 carbon atoms,
$R^1$ and $R^2$ are the same or different and each represents a hydrogen atom or an alkyl group having from 1 to 6 carbon atoms, and
$R^3$ is selected from the group consisting of an alkoxy group having from 1 to 6 carbon atoms that may optionally be substituted with one hydroxy group, and a group represented by the formula —$NR^4R^5$, wherein $R^4$ and $R^5$ are the same or different from each other and each represents a hydrogen atom or an alkyl group having from 1 to 6 carbon atoms that may optionally be substituted with one hydroxy group.

9. A copolymer or a pharmacologically acceptable salt thereof, with an average degree of polymerization in the range of from 5 to 200, obtainable by subjecting one or more carboxylic anhydride moieties of formula (III) in a copolymer consisting of, as constitutional units,
(a) one or more structural units which may be the same or different from each other and which are represented by the formula (I) below:

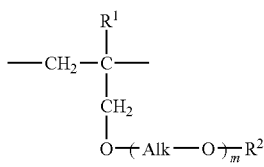

wherein:
m is an integer of from 3 to 100,
Alk represents an alkylene group having from 1 to 6 carbon atoms, and
$R^1$ and $R^2$ are the same or different and each represents a hydrogen atom or an alkyl group having from 1 to 6 carbon atoms that may optionally be substituted with at least one substituent selected from the group consisting of hydroxy groups, halogen atoms and aryl groups having from 6 to 14 carbon atoms that may optionally be substituted with from 1 to 5 substituents selected from Substituents A defined below and
(b) said structural unit comprising a carboxylic anhydride moiety of formula (III):

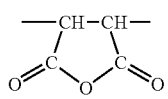

to one or more reactions selected from the group consisting of (i) ammonolysis, (ii) aminolysis, and (iii) alcoholysis, or to a combination reaction of hydrolysis and other reactions listed above, wherein the ratio of hydrolysis: the other reaction is 5:5 to 0:10;
Substituents A are selected from alkyl groups having from 1 to 6 carbon atoms, alkoxy groups having from 1 to 6 carbon atoms, halogen atoms, hydroxy groups, nitro groups and carboxy groups.

10. A copolymer or a pharmacologically acceptable salt thereof according to claim 9, which is obtainable by subjecting a carboxylic anhydride moiety of formula (III) in the copolymer to ammonolysis.

11. A copolymer or a pharmacologically acceptable salt thereof according to claim 1, wherein Alk is an ethylene group.

12. A copolymer or a pharmacologically acceptable salt thereof according to claim 1, wherein m is an integer of from 3 to 50.

13. A copolymer or a pharmacologically acceptable salt thereof according to claim 1, wherein m is an integer of from 3 to 40.

14. A copolymer or a pharmacologically acceptable salt thereof according to claim 1, wherein m is an integer of from 6 to 16.

15. A copolymer or a pharmacologically acceptable salt thereof according to claim 1, wherein $R^1$ is a hydrogen atom.

16. A copolymer or a pharmacologically acceptable salt thereof according to claim 1, wherein $R^2$ is a methyl group.

17. A copolymer or a pharmacologically acceptable salt thereof according to claim 1, wherein $R^3$ is a group represented by the formula —$NR^4R^5$, wherein $R^4$ and $R^5$ are the same or different and each represents a hydrogen atom or an alkyl group having from 1 to 6 carbon atoms and optionally at least one structural unit represented by the formula (II) in which $R^3$ is a hydroxyl group, wherein the ratio between the structural units represented by the formula (II) in which $R^3$ is a hydroxy group and the structural units represented by the formula (II) in which $R^3$ is a group represented by the formula —$NR^4R^5$ is in the range of from 5:5 to 0:10.

18. A copolymer or a pharmacologically acceptable salt thereof according to claim 1, wherein $R^3$ is a group represented by the formula —$NR^4R^5$, wherein $R^4$ and $R^5$ are the same or different and each represents a hydrogen atom or an alkyl group having from 1 to 6 carbon atoms.

19. A copolymer or a pharmacologically acceptable salt thereof according to claim 1, wherein the group represented by the formula —$NR^4R^5$ is an amino group.

20. A copolymer or a pharmacologically acceptable salt thereof according to claim 1, wherein the ratio between the structural unit represented by the formula (I) and the structural unit represented by the formula (II) is in the range of from 3:1 to 1:8.

21. A copolymer or a pharmacologically acceptable salt thereof according to claim 1, wherein the ratio between the structural unit represented by the formula (I) and the structural unit represented by the formula (II) is in the range of from 2:1 to 1:2 or 1:2 to 1:6.

22. A copolymer or a pharmacologically acceptable salt thereof according to claim 1, wherein the ratio between the structural unit represented by the formula (I) and the structural unit represented by the formula (II) is 1:1 or in the range of from 1:2 to 1:4.

23. A copolymer or a pharmacologically acceptable salt thereof according to claim 1, wherein the average degree of polymerization is in the range of from 5 to 50.

24. A copolymer or a pharmacologically acceptable salt thereof according to claim 1, wherein the average degree of polymerization is in the range of from 5 to 20.

25. A copolymer or a pharmacologically acceptable salt thereof according to claim 1, wherein the average degree of polymerization is in the range of from 20 to 30.

26. A copolymer or a pharmacologically acceptable salt thereof according to of claim 1, wherein the average degree of polymerization is in the range of from 30 to 40.

27. A copolymer or a pharmacologically acceptable salt thereof according to claim 1, wherein the Stokes radius thereof is 7.3 nm or less.

28. A copolymer or a pharmacologically acceptable salt thereof according to claim 1, wherein the Stokes radius thereof is 6.2 nm or less.

29. A copolymer or a pharmacologically acceptable salt thereof according to claim 1, wherein the Stokes radius thereof is 4.7 nm or less.

30. A copolymer or a pharmacologically acceptable salt thereof according to claim 1, wherein the Stokes radius thereof is 3.1 nm or less.

31. A copolymer or a pharmacologically acceptable salt thereof according to claim 1, wherein the Stokes radius thereof is in the range of from 1.5 nm to 4.7 nm.

32. A copolymer or a pharmacologically acceptable salt thereof according to claim 1, wherein the Stokes radius thereof is in the range of from 3.1 nm to 6.2 nm.

33. A copolymer or a pharmacologically acceptable salt thereof according to claim 9, wherein the structural unit represented by the formula (I) and the structural unit represented by the formula (III) in the copolymer are arranged in an alternating head-to-head sequence, an alternating head-to-tail sequence or an alternating mixed sequence of head-to-head and head-to-tail.

34. A copolymer or a pharmacologically acceptable salt thereof according to according to claim 9, wherein the structural unit represented by the formula (I) and the structural unit represented by the formula (III) in the copolymer are arranged in random sequence.

35. A copolymer or a pharmacologically acceptable salt thereof according to claim 9, wherein Alk is an ethylene group.

36. A copolymer or a pharmacologically acceptable salt thereof according to claim 9, wherein m is an integer of from 3 to 50.

37. A copolymer or a pharmacologically acceptable salt thereof according to claim 9, wherein m is an integer of from 3 to 40.

38. A copolymer or a pharmacologically acceptable salt thereof according to claim 9, wherein m is an integer of from 6 to 16.

39. A copolymer or a pharmacologically acceptable salt thereof according to claim 9, wherein $R^1$ is a hydrogen atom.

40. A copolymer or a pharmacologically acceptable salt thereof according to claim 9, wherein $R^2$ is a methyl group.

41. A copolymer or a pharmacologically acceptable salt thereof according to claim 9, wherein the ratio between the structural unit represented by the formula (I) and the structural unit obtained by subjecting one or more structural units of formula (III) to one or more reactions selected from the group consisting of (i) hydrolysis, (ii) ammonolysis, (iii) aminolysis and (iv) alcoholysis is in the range of from 10:1 to 1:10.

42. A copolymer or a pharmacologically acceptable salt thereof according to claim 9, wherein the ratio between the structural unit represented by the formula (I) and the structural unit obtained by subjecting one or more structural units of formula (III) to one or more reactions selected from the group consisting of (i) hydrolysis, (ii) ammonolysis, (iii) aminolysis and (iv) alcoholysis is in the range of from 3:1 to 1:8.

43. A copolymer or a pharmacologically acceptable salt thereof according to claim 9, wherein the ratio between the structural unit represented by the formula (I) and the structural unit obtained by subjecting one or more structural units of formula (III) to one or more reactions selected from the group consisting of (i) hydrolysis, (ii) ammonolysis, (iii) aminolysis and (iv) alcoholysis is in the range of from 2:1 to 1:2 or 1:2 to 1:6.

44. A copolymer or a pharmacologically acceptable salt thereof according to claim 9, wherein the ratio between the structural unit represented by the formula (I) and the structural unit obtained by subjecting one or more structural units of formula (III) to one or more reactions selected from the group consisting of (i) hydrolysis, (ii) ammonolysis, (iii) aminolysis and (iv) alcoholysis is 1:1 or in the range of from 1:2 to 1:4.

45. A copolymer or a pharmacologically acceptable salt thereof according to claim 9, wherein the average degree of polymerization is in the range of from 5 to 50.

46. A copolymer or a pharmacologically acceptable salt thereof according to claim 9, wherein the average degree of polymerization is in the range of from 5 to 20.

47. A copolymer or a pharmacologically acceptable salt thereof according to claim 9, wherein the average degree of polymerization is in the range of from 20 to 30.

48. A copolymer or a pharmacologically acceptable salt thereof according to claim 9, wherein the average degree of polymerization is in the range of from 30 to 40.

49. A copolymer or a pharmacologically acceptable salt thereof according to claim 9, which is obtainable by carrying out the ammonolysis with ammonia water.

50. A copolymer or a pharmacologically acceptable salt thereof according to claim 9, which is obtainable by subjecting a carboxylic anhydride moiety of formula (III) in the copolymer to aminolysis.

51. A copolymer or a pharmacologically acceptable salt thereof according to claim 9, which is obtainable by carrying out the aminolysis using an aqueous dimethylamine solution.

52. A copolymer or a pharmacologically acceptable salt thereof according to claim 9, which is obtainable by subjecting a carboxylic anhydride moiety of formula (III) in the copolymer to alcoholysis.

53. A copolymer or a pharmacologically acceptable salt thereof according to claim 9, which is obtainable by carrying out the alcoholysis using ethanol.

\* \* \* \* \*